(12) United States Patent
Wagner

(10) Patent No.: US 10,801,041 B2
(45) Date of Patent: Oct. 13, 2020

(54) T7 ALPHA VIRAL VECTOR SYSTEM

(71) Applicant: ORBIS HEALTH SOLUTIONS, LLC, Greenville, SC (US)

(72) Inventor: Thomas E. Wagner, Greenville, SC (US)

(73) Assignee: Orbis Health Solutions, LLC, Greenville, SC (US)

( * ) Notice: Subject to any disclaimer, the term of this patent is extended or adjusted under 35 U.S.C. 154(b) by 0 days.

(21) Appl. No.: 15/776,855

(22) PCT Filed: Nov. 18, 2016

(86) PCT No.: PCT/US2016/062703
§ 371 (c)(1),
(2) Date: May 17, 2018

(87) PCT Pub. No.: WO2017/087763
PCT Pub. Date: May 26, 2017

(65) Prior Publication Data
US 2018/0371494 A1    Dec. 27, 2018

Related U.S. Application Data

(60) Provisional application No. 62/256,788, filed on Nov. 18, 2015.

(51) Int. Cl.
| | | |
|---|---|---|
| C12N 15/86 | (2006.01) | |
| A61P 37/04 | (2006.01) | |
| A61K 39/12 | (2006.01) | |
| A61K 39/145 | (2006.01) | |
| C07K 14/005 | (2006.01) | |
| C12N 5/074 | (2010.01) | |
| A61K 39/00 | (2006.01) | |

(52) U.S. Cl.
CPC ............. *C12N 15/86* (2013.01); *A61K 39/12* (2013.01); *A61K 39/145* (2013.01); *A61P 37/04* (2018.01); *C07K 14/005* (2013.01); *C12N 5/0696* (2013.01); *A61K 2039/53* (2013.01); *A61K 2039/876* (2018.08); *C12N 2501/20* (2013.01); *C12N 2760/16034* (2013.01); *C12N 2770/36134* (2013.01); *C12N 2770/36143* (2013.01); *C12N 2770/36151* (2013.01); *C12N 2770/36152* (2013.01); *C12N 2795/10222* (2013.01); *C12N 2830/00* (2013.01); *C12N 2840/203* (2013.01)

(58) Field of Classification Search
None
See application file for complete search history.

(56) References Cited

U.S. PATENT DOCUMENTS

| | | |
|---|---|---|
| 4,708,871 A | 11/1987 | Geysen |
| 4,937,190 A | 6/1990 | Palmenberg et al. |
| 4,968,603 A | 11/1990 | Slamon et al. |
| 5,122,457 A | 6/1992 | Reim et al. |
| 5,788,963 A | 8/1998 | Murphy et al. |
| 5,851,756 A | 12/1998 | Steinman et al. |
| 5,962,318 A | 10/1999 | Rooney et al. |
| 6,387,888 B1 | 5/2002 | Mincheff et al. |
| 2002/0155609 A1* | 10/2002 | Wagner .................. A61K 39/00 435/456 |
| 2003/0170871 A1 | 9/2003 | Dubensky, Jr. et al. |
| 2005/0277605 A1 | 12/2005 | Wu et al. |
| 2007/0166820 A1 | 7/2007 | Smith et al. |
| 2008/0152633 A1* | 6/2008 | Suhrbier .............. C07K 14/005 424/93.21 |
| 2009/0117658 A1* | 5/2009 | Wagner .................. A61K 47/61 435/456 |
| 2011/0250692 A1 | 10/2011 | Yamanaka et al. |
| 2012/0156251 A1* | 6/2012 | Brito ...................... A61K 9/107 424/400 |
| 2012/0207744 A1 | 8/2012 | Mendlein et al. |
| 2012/0258126 A1* | 10/2012 | Scholler ................. A61K 39/00 424/186.1 |
| 2013/0078205 A1 | 3/2013 | Dayan et al. |
| 2015/0159143 A1 | 6/2015 | Dowdy et al. |
| 2015/0196630 A1* | 7/2015 | Dodd ...................... A61K 39/12 424/186.1 |

FOREIGN PATENT DOCUMENTS

| | | |
|---|---|---|
| WO | WO 90/05142 A1 | 5/1990 |
| WO | WO 2004/058660 A2 | 10/2004 |
| WO | WO 2004/058660 A3 | 10/2004 |
| WO | WO 2007/069666 A1 | 6/2007 |
| WO | WO 2008/118820 A2 | 10/2008 |
| WO | WO 2012/058072 A1 | 5/2012 |

(Continued)

OTHER PUBLICATIONS

Suckow MA. Cancer vaccines: harnessing the potential of antitumor immunity. Vet J. Oct. 2013;198(1):28-33. doi: 10.1016/j.tvjl.2013.06.005. Epub Jul. 10, 2013.*
Osada T, Morse MA, Hobeika A, Lyerly HK. Novel recombinant alphaviral and adenoviral vectors for cancer immunotherapy. Semin Oncol. Jun. 2012;39(3):305-10.*
Darani HY, Yousefi M. Parasites and cancers: parasite antigens as possible targets for cancer immunotherapy. Future Oncol. Dec. 2012;8(12):1529-35.*
Shin et al., PNAS, 2012, 109(41):16534-16539. (Year: 2012).*
Tinnares et al., PNAS, 1998, 95:13147-13152. (Year: 1998).*
Berhard et al., "Generation of Immunostimulatory Dendritic Cells from Human CD34+ Hematopoietic Progenitor Cells of the Bone Marrow and Peripheral Blood," Cancer Research, 1995, 55:1099-1104.

(Continued)

*Primary Examiner* — Nicole Kinsey White
(74) *Attorney, Agent, or Firm* — Foley & Lardner LLP

(57) ABSTRACT

The present invention relates generally to a gene expression system utilizing an alphavirus replicon and T7 promoter. The system is capable of expressing proteins in the cell cytoplasm without integrating the gene of interest into the genome of a host cell. The invention has a wide range of applications such as producing induced pluripotent cells and vaccines against pathogens and cancers.

20 Claims, 1 Drawing Sheet

Specification includes a Sequence Listing.

(56) References Cited

FOREIGN PATENT DOCUMENTS

WO    WO 2013/177133 A2    11/2013

OTHER PUBLICATIONS

Brichard et al., "The Tyrosinase Gene Codes for an Antigen Recognized by Autologous Cytolytic T Lymphocytes on HLA-A2 Melanomas," J. Exp. Med., Aug. 1993, 178:489-495.
Casales et al., "Development of a new noncytopathic Semliki Forest virus vector providing high expression levels and stability," Virology, Apr. 28, 2008, 376(1):242-251.
Coulie et al., "A New Gene Coding for a Differentiation Antigen Recognized by Autologous Cytolytic T Lymphocytes on HLA-A2 Melanomas," J. Exp. Med., Jul. 1994, 180:35-42.
Frolova et al., "Roles of Nonstructural Protein nsP2 and Alpha/Beta Interferons in Determining the Outcome of Sindbis Virus Infection," J. Virol., Nov. 2002, 76(22):11254-11264.
Frolov et al., "Selection of RNA Replicons Capable of Persistent Noncytopathic Replication in Mammalian Cells," J. Virol., May 1999, 73(5):3854-3865.
Geysen et al., "A Priori Delineation of a Peptide Which Mimics a Discontinuous Antigenic Determinant," Molec. Immunol., 1986, 23(7):709-715.
Geysen et al., "Use of peptide synthesis to probe viral antigens for epitopes to a resolution of a single amino acid," Proc. Natl. Acad. Sci. USA, Jul. 1984, 81:3998-4002.
Hasegawa et al., "Efficient Multicistronic Expression of a Transgene in Human Embryonic Stem Cells," Stem Cells, 2007, 25:1707-1712.
Hsiao et al., "Marking Embryonic Stem Cells with a 2A Self-Cleaving Peptide : A NKX2-5 Emerald GFP BAC Reporter," PLoS ONE, Jul. 2008, 3(7):e2532(1-8).
Huangfu et al., "Induction of pluripotent stem cells by defined factors is greatly improved by small-molecule compounds," Nat. Biotechnol., Jul. 2008, 26 (7):795-797.
Judson et al., "Embryonic stem cell-specific microRNAs promote induced pluripotency," Nat. Biotechnol., May 2009, 27(5):459-461.
Kawakami et al., "Recognition of Tyrosinase by Tumor-infiltrating Lymphocytes from a Patient Responding to Immunotherapy," Cancer Res., Jun. 15, 1994, 54:3124-3126.
Kawakami et al., "Identification of the Immunodominant Peptides of the MART-1 Human Melanoma Antigen Recognized by the Majority of HLA-A2-restricted Tumor Infiltrating Lymphocytes," J. Exp. Med., Jul. 1994, 180:347-352.
Kawakami et al., "Cloning of the gene coding for a shared human melanoma antigen recognized by autologous T cells infiltrating into tumor," Proc. Natl. Acad. Sci. USA, Apr. 1994, 91:3515-3519.
Kubicek et al., "Reversal of H3K9me2 by a Small-Molecule Inhibitor for the G9a Histone Methyltransferase," Mol. Cell, Feb. 9, 2007, 25:473-481.
Larsen et al., "Migration and Maturation of Langerhans Cells in Skin Transplants and Explants," J. Exp. Med., Nov. 1990, 172:1483-1493.
Levine, Arnold J., "The Tumor Suppressor Genes," Ann. Rev. Biochem., 1993, 62:623-651.
Liljestrom et al., "A New Generation of Animal Cell Expression Vectors Based on the Semliki Forest Virus Replicon," Biotechnology, Dec. 1991, 9:1356-1361.
Lundstrom et al., "Efficient in vivo expression of a reporter gene in rat brain after injection of recombinant replication-deficient Semliki Forest virus," Gene Ther. Mol. Biol., Aug. 1999, 3:15-23.
Lundstrom et al., "Novel mutant Semliki Forest virus vectors: gene expression and localization studies in neuronal cells," Histochem. Cell Biol., 2001, 115:83-91.
Lundstrom et al., "Alphavirus vectors for vaccine production and gene therapy," Expert Review of Vaccines, 2003, 2:447-459.
Macatonia et al., "Primary proliferative and cytotoxic T-cell responses to HIF induced in vitro by human dendritic cells," Immunology, 1991, 74:399-406.
Markowicz et al., "Granulocyte-macrophage colony-stimulating factor promotes differentiation and survival of human peripheral blood dendritic cells in vitro," J. Clin. Invest., 1990, 85(3):955-961.
Marson et al., "Wnt Signaling Promotes Reprogramming of Somatic Cells to Pluripotency," Cell Stem Cell, Aug. 7, 2008, 3:132-135.
Martinez-Salas et al., "Functional interactions in internal translation initiation directed by viral and cellular IRES elements," Journal of General Virology, 2001, 82:973-984.
McMahon et al., "The WNT-1 (int-1) Proto-Oncogene is Required for Development of a Large Region of the Mouse Brain," Cell, Sep. 21, 1990, 62:1073-1085.
Nakagawa et al., "Generation of induced pluripotent stem cells without Myc from mouse and human fibroblasts," Nat. Biotechnol., Jan. 2008, 26(1):101-106.
O'Doherty et al., "Dendritic Cells Freshly Isolated from Human Blood Express CD4 and Mature into Typical Immunostimulatory Dendritic Cells after Culture in Monocyte-conditioned Medium," J. Exp. Med., Sep. 1, 1993, 178:1067-1078.
Perri et al., "Replicon Vectors Derived from Sindbis Virus and Semliki Forest Virus That Establish Persistent Replication in Host Cells," J. Virol., Oct. 2000, 74:9802-9807.
Petrakova et al., "Noncytopathic Replication of Venezuelan Equine Encephalitis Virus and Eastern Equine Encephalitis Virus Replicons in Mammalian Cells," J. Virol., Jun. 2005, 79(12):7597-7608.
Pushko et al., "Replicon-Helper Systems from Attenuated Venezuelan Equine Encephalitis Virus: Expression of Heterologous Genes in Vitro and Immunization against Heterologous Pathogens in Vivo," Virology, 1997, 239:389-401.
Richters et al., J. Invest. Dermatol., Jan.-Dec. 1994, Table of Contents.
Romani et al., "Proliferating Dendritic Cell Progenitors in Human Blood," J. Exp. Med., Jul. 1, 1994, 180:83-93.
Rosenberg, Steven A., M.D., Ph.D., "The Innumotherapy of Solid Cancers Based on Cloning the Genes Encoding Tumor-Rejection Antigens," Ann. Rev. Med., 1996, 47:481-941.
Sallusto et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor α," J. Exp. Med., Apr. 1, 1994, 179:1109-1118.
Shi et al., "A Combined Chemical and Genetic Approach for the Generation of Induced Pluripotent Stem Cells," Cell Stem Cell, Jun. 2008, 2:525-528.
Shi et al., "Induction of Pluripotent Stem Cells from Mouse Embryonic Fibroblasts by Oct4 and Klf4 with Small-Molecule Compounds," Cell Stem Cell, Nov. 6, 2008, 3:568-574.
Silva et al., "Promotion of Reprogramming to Ground State Pluripotency by Signal Inhibition," PLoS Biology, Oct. 2008, 6(10):e253, 2237-2247.
Takahashi et al., "Induction of Pluripotent Stem Cells from Adult Human Fibroblasts by Defined Factors," Cell, Nov. 30, 2007, 131:861-872.
Takahashi et al., "Induction of Pluripotent Stem Cells from Mouse Embryonic and Adult Fibroblast Cultures by Defined Factors," Cell, Aug. 25, 2006, 126:663-676.
Van der Bruggen et al., "A Gene Encoding an Antigen Recognized by Cytolytic T Lymphocytes on a Human Melanoma," Science, Dec. 13, 1991, 254:1643-1647.
Van Tendeloo et al., "Nonviral transfection of distinct types of human dendritic cells: high efficiency gene transfer by electroporation into hematopoietic progenitor—but not monocyte-derived dendritic cells," Gene Ther., 1998, 5:700-707.
Wick et al., "Recongition of malignant melanoma by monoclonal antibody HMB-45. An immunohistochemical study of 200 paraffin-embedded cutaneous tumors," J. Cutan. Pathol., 1998, 15:201-207.
Xiong et al., "Sindbis Virus: An Efficient, Broad Host Range Vector for Gene Expression in Animal Cells," Science, Mar. 3, 1989, 243:1188-1191.
Yang et al., "Location of the internal ribosome entry site in the 5' non-coding region of the immunoglobulin heavy-chain binding

(56) References Cited

OTHER PUBLICATIONS protein (BiP) mRNA: evidence for specific RNA-protein interactions," Nucleic Acids Research, 1997, 25(14):2800-2807.
Yu et al., "Induced Pluripotent Stem Cell Lines Derived from Human Somatic Cells," Science, Dec. 21, 2007, 318:1917-1920.
Zhao et al., "Two Supporting Factors Greatly Improve the Efficiency of Human iPSC Generation," Cell Stem Cell, Nov. 6, 2008, 3:475-479.
Di Nicola, M. et al. Boosting T Cell-Mediated Immunity to Tyrosinase by Vaccinia Virus-Induced, CD34+-Derived Dendritic Cell Vaccination: A Phase I Trial in Metastatic Melanoma, Clinical Cancer Research, vol. 10, Aug. 15, 2004, pp. 5381-5390, XP055575673.
Gao, X., et al., Cytoplasmic expression of a reporter gene by co-delivery of T7 RNA polymerase and T7 promoter sequence with cationic liposomes, Nucleic Acids Research, 21(12), pp. 2867-2872, 1993, XP00057618.
Ghaderi, M. et al., Construction of an eGFP expression plasmid under control of T7 promoter and IRES sequence for assay of T7 RNA polymerase activity in mammalian cell lines, Iranian Journal of cancer prevention, 7(3): 137-141 (2014), XP055491850.
Moran, T. P. et al., Alphaviral vector-transduced dendritic cells are successful therapeutic vaccines against neu-overexpressing tumors in wild-type mice, Vaccine 25 (2007), pp. 6604-6612, XP022191550.
Spuul, P. et al., Assembly of alphavirus replication complexes from RNA and protein components in a novel trans-replication system of mammalian cells, Journal of Virology, 85(10): 4739-4751 (2011), XP055273102.
Supplemental European Search Report regarding Application No. EP 16867199, dated Apr. 10, 2019, 11 pages.
Bronte, et al., "Genetic Vaccination With 'Self' Tyrosinase-Related Protein 2 Causes Melanoma Eradication But Not Vitiligo," Cancer Research, vol. 60, pp. 253-258, dated Jan. 15, 2000 (7 pages).
Di Nicola, et al., "Boosting T Cell-Mediated Immunity to Tyrosinase by Vaccinia Virus-Transduced, CD34+-Derived Dendritic Cell Vaccination: A Phase I Trial in Metastatic Melanoma," Clincal Cancer Research, vol. 10, pp. 5381-5390, dated Aug. 15, 2004 (11 pages).
International Preliminary Report on Patentability on PCT Appln. Ser. No. PCT/US2016/062703 dated May 31, 2018 (9 pages).
International Search Report and Written Opinion on PCT Appln. Ser. No. PCT/US2016/062703 dated Mar. 30, 2017 (11 pages).
Office Action on SG Appln. Ser. No. 11201804197R dated Oct. 3, 2019 (10 pages).
Overwijk, et al., "Vaccination With a Recombinant Vaccinia Virus Encoding a 'Self' Antigen Induces Autoimmune Vitiligo and Tumor Cell Destruction in Mice: Requirement for CD4 T Lymphocytes," Proc. Natl. Acad. Sci. USA, vol. 96, pp. 2982-2987, dated Dec. 31, 1998 (6 pages).

* cited by examiner

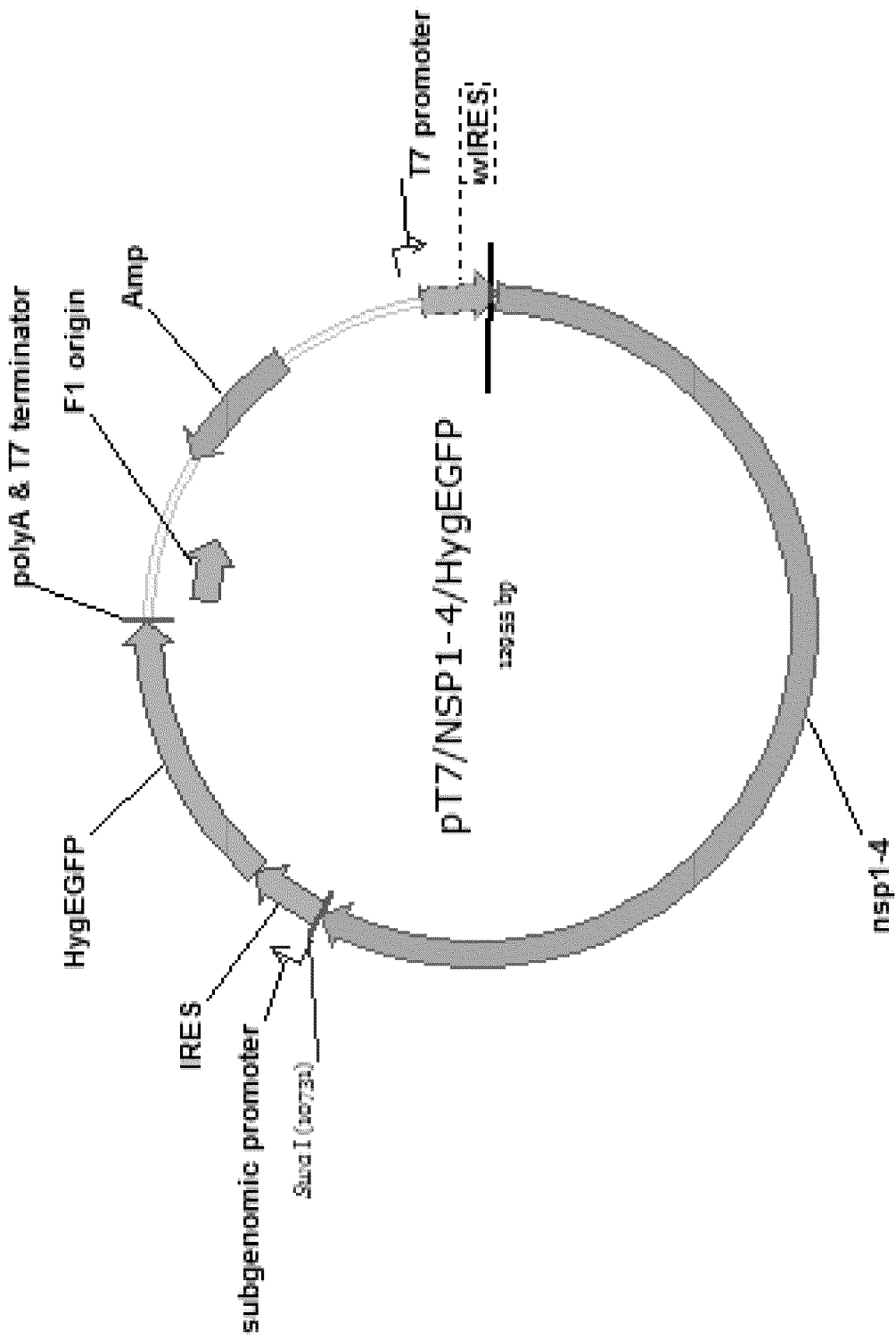

SEQUENCE LISTING

<160> NUMBER OF SEQ ID NOS: 16

<210> SEQ ID NO 1
<211> LENGTH: 12955
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gggcggccgc aaaaaaaaaa aaaaaaaaaa aaaaaaaaa ctagcataac cccttggggc      60
ctctaaacgg gtcttgaggg gttttttgga tccgggctgg cgtaatagcg aagaggcccg     120
caccgatcgc ccttcccaac agttgcgcag cctgaatggc gaatgacgc gccctgtagc     180 ggcgcattaa gcgcggcggg tgtggtggtt acgcgcagcg tgaccgctac acttgccagc     240
gccctagcgc ccgctccttt cgctttcttc ccttcctttc tcgccacgtt cgccggcttt     300
ccccgtcaag ctctaaatcg ggggctccct ttagggttcc gatttagtgc tttacggcac     360
ctcgacccca aaaaacttga ttagggtgat ggttcacgta gtgggccatc gccctgatag     420 acggttttc gccctttgac gttggagtcc acgttcttta atagtggact cttgttccaa      480

```
actggaacaa cactcaaccc tatctcggtc tattcttttg atttataagg gattttgccg    540
atttcggcct attggttaaa aaatgagctg atttaacaaa aatttaacgc gaattttaac    600
aaaatattaa cgcttacaat ttcctgatgc ggtatttcct ccttacgcat ctgtgcggta    660
tttcacaccg catatggtgc actctcagta caatctgctc tgatgccgca tagttaagcc    720
agccccgaca cccgccaaca cccgctgacg cgccctgacg ggcttgtctg ctcccggcat    780
ccgcttacag acaagctgtg accgtctccg ggagctgcat gtgtcagagg ttttcaccgt    840
catcaccgaa acgcgcgaga cgaaagggcc tcgtgatacg cctatttta taggttaatg    900 tcatgataat aatggtttct tagacgtcag gtggcacttt tcggggaaat gtgcgcggaa    960
cccctatttg tttattttc taaatacatt caaatatgta tccgctcatg agacaataac    1020
cctgataaat gcttcaataa tattgaaaaa ggaagagtat gagtattcaa catttccgtg    1080
tcgcccttat tcccttttt gcggcatttt gccttcctgt ttttgctcac ccagaaacgc    1140
tggtgaaagt aaaagatgct gaagatcagt tgggtgcacg agtgggttac atcgaactgg    1200
atctcaacag cggtaagatc cttgagagtt ttcgccccga agaacgtttt ccaatgatga    1260
gcacttttaa agttctgcta tgtggcgcgg tattatcccg tattgacgcc gggcaagagc    1320
aactcggtcg ccgcatacac tattctcaga atgacttggt tgagtactca ccagtcacag    1380
aaaagcatct tacgatggc atgacagtaa gagaattatg cagtgctgcc ataaccatga    1440
gtgataacac tgcggccaac ttacttctga caacgatcgg aggaccgaag gagctaaccg    1500
cttttttgca caacatgggg gatcatgtaa ctcgccttga tcgttgggaa ccggagctga    1560
atgaagccat accaaacgac gagcgtgaca ccacgatgcc tgtagcaatg gcaacaacgt    1620
tgcgcaaact attaactggc gaactactta ctctagcttc ccggcaacaa ttaatagact    1680
ggatggaggc ggataaagtt gcaggaccac ttctgcgctc ggcccttccg gctggctggt    1740
ttattgctga taaatctgga gccggtgagc gtgggtctcg cggtatcatt gcagcactgg    1800
ggccagatgg taagccctcc cgtatcgtag ttatctacac gacggggagt caggcaacta    1860
tggatgaacg aaatagacag atcgctgaga taggtgcctc actgattaag cattggtaac    1920
tgtcagacca agtttactca tatatacttt agattgattt aaaacttcat ttttaattta    1980
aaaggatcta ggtgaagatc ctttttgata atctcatgac caaaatccct aacgtgagt    2040 tttcgttcca ctgagcgtca gaccccgtag aaaagatcaa aggatcttct tgagatcctt    2100 ttttttctgcg cgtaatctgc tgcttgcaaa caaaaaaacc accgctacca gcggtggttt    2160
gtttgccgga tcaagagcta ccaactcttt ttccgaaggt aactggcttc agcagagcgc    2220
agataccaaa tactgttctt ctagtgtagc cgtagttagg ccaccacttc aagaactctg    2280
tagcaccgcc tacatacctc gctctgctaa tcctgttacc agtggctgct gccagtggcg    2340
ataagtcgtg tcttaccggg ttggactcaa gacgatagtt accggataag gcgcagcggt    2400
cgggctgaac ggggggttcg tgcacacagc ccagcttgga gcgaacgacc tacaccgaac    2460
tgagatacct acagcgtgag ctatgagaaa gcgccacgct tcccgaaggg agaaaggcgg    2520
acaggtatcc ggtaagcggc agggtcggaa caggagagcg cacgagggag cttccagggg    2580
gaaacgcctg gtatctttat agtcctgtcg ggtttcgcca cctctgactt gagcgtcgat    2640
ttttgtgatg ctcgtcaggg gggcggagcc tatgaaaaa cgccagcaac gcggcctttt    2700
tacggttcct ggccttttgc tggccttttg ctcacatggc tcgacagatc ttaaggctag    2760
agtacttaat acgactcact ataggctagc atttaggtga cactatagaa tacaagctac    2820
ttgttctttt tgcactcgag aattcacgcg tggtacctct agagtcgacc cgttattttc    2880
```

```
caccatattg ccgtcttttg gcaatgtgag ggcccggaaa cctggccctg tcttcttgac      2940
gagcattcct aggggtcttt ccctctcgc caaaggaatg caaggtctgt tgaatgtcgt       3000
gaaggaagca gttcctctgg aagcttcttg aagacaaaca acgtctgtag cgaccctttg      3060
caggcagcgg aaccccccac ctggcgacag gtgcctctgc ggccaaaagc cacgtgtata      3120
agatacacct gcaaaggcgg cacaaccca gtgccacgtt gtgagttgga tagttgtgga      3180
aagagtcaaa tggctctcct caagcgtatt caacaagggg ctgaaggatg cccagaaggt     3240
accccattgt atgggatctg atctggggcc tcggtgcaca tgctttacat gtgtttagtc     3300
gaggttaaaa aacgtctagg ccccccgaac cacggggacg tggttttcct ttatggcgga    3360
tgtgtgacat acacgacgcc aaaagatttt gttccagctc ctgccacctc cgctacgcga    3420
gagattaacc acccacgatg gccgccaaag tgcatgttga tattgaggct gacagcccat    3480
tcatcaagtc tttgcagaag gcatttccgt cgttcgaggt ggagtcattg caggtcacac    3540
caaatgacca tgcaaatgcc agagcatttt cgcacctggc taccaaattg atcgagcagg   3600
agactgacaa agacacactc atcttggata tcggcagtgc gccttccagg agaatgatgt   3660
ctacgcacaa ataccactgc gtatgcccta tgcgcagcgc agaagacccc gaaaggctcg   3720
atagctacgc aaagaaactg gcagcggcct ccgggaaggt gctggataga gagatcgcag   3780
gaaaaatcac cgacctgcag accgtcatgg ctacgccaga cgctgaatct cctacctttt   3840
gcctgcatac agacgtcacg tgtcgtacgg cagccgaagt ggccgtatac caggacgtgt   3900
atgctgtaca tgcaccaaca tcgctgtacc atcaggcgat gaaaggtgtc agaacggcgt   3960
attggattgg gtttgacacc accccgttta tgtttgacgc gctagcaggc gcgtatccaa    4020
cctacgccac aaactgggcc gacgagcagg tgttacaggc caggaacata ggactgtgtg    4080
cagcatcctt gactgaggga agactcggca aactgtccat tctccgcaag aagcaattga    4140
aaccttgcga cacagtcatg ttctcggtag gatctacatt gtacactgag agcagaaagc   4200
tactgaggag ctggcactta ccctccgtat tccacctgaa aggtaaacaa tcctttaccct   4260 gtaggtgcga taccatcgta tcatgtgaag ggtacgtagt taagaaaatc actatgtgcc   4320
ccggcctgta cggtaaaacg gtagggtacg ccgtgacgta tcacgcggag ggattcctag   4380
tgtgcaagac cacagacact gtcaaaggag aaagagtctc attccctgta tgcacctacg   4440 tccctcaac catctgtgat caaatgactg gcatactagc gaccgacgtc acaccggagg    4500
acgcacagaa gttgttagtg ggattgaatc agaggatagt tgtgaacgga gaacacagc    4560 gaaacactaa cacgatgaag aactatctgc ttccgattgt ggccgtcgca tttagcaagt   4620
gggcgaggga atacaaggca gaccttgatg atgaaaaacc tctgggtgtc cgagagaggt   4680
cacttacttg ctgctgcttg tgggcattta aaacgaggaa gatgcacacc atgtacaaga   4740
aaccagacac ccagacaata gtgaaggtgc cttcagagtt taactcgttc gtcatcccga   4800
gcctatggtc tacaggcctc gcaatcccag tcagatcacg cattaagatg cttttggcca   4860
agaagaccaa gcgagagtta atacctgttc tcgacgcgtc gtcagccagg gatgctgaac   4920
aagaggagaa ggagaggttg gaggccgagc tgactagaga agccttacca cccctcgtcc   4980
ccatcgcgcc ggcggagacg ggagtcgtcg acgtcgacgt tgaagaacta gagtatcacg   5040
caggtgcagg ggtcgtggaa acacctcgca gcgcgttgaa agtcaccgca cagccgaacg   5100
acgtactact aggaaattac gtagttcgt ccccgcagac cgtgctcaag agctccaagt    5160
tggcccccgt gcaccctcta gcagagcagg tgaaaataat aacacataac gggagggccg   5220
```

```
gcggttacca ggtcgacgga tatgacggca gggtcctact accatgtgga tcggccattc   5280
cggtccctga gttttcaagct ttgagcgaga gcgccactat ggtgtacaac gaaagggagt   5340
tcgtcaacag gaaactatac catattgccg ttcacggacc gtcgctgaac accgacgagg   5400
agaactacga gaaagtcaga gctgaaagaa ctgacgccga gtacgtgttc gacgtagata   5460
aaaaatgctg cgtcaagaga gaggaagcgt cgggtttggt gttggtggga gagctaacca   5520
accccccgtt ccatgaattc gcctacgaag ggctgaagat caggccgtcg gcaccatata   5580
agactacagt agtaggagtc tttggggttc cgggatcagg caagtctgct attattaaga   5640
gcctcgtgac caaacacgat ctggtcacca gcggcaagaa ggagaactgc caggaaatag   5700
ttaacgacgt gaagaagcac cgcgggaagg ggacaagtag ggaaaacagt gactccatcc   5760
tgctaaacgg gtgtcgtcgt gccgtggaca tcctatatgt ggacgaggct ttcgctagcc   5820
attccggtac tctgctggcc ctaattgctc ttgttaaacc tcggagcaaa gtggtgttat   5880
gcggagaccc caagcaatgc ggattcttca atatgatgca gcttaaggtg aacttcaacc   5940
acaacatctg cactgaagta tgtcataaaa gtatatccag acgttgcacg cgtccagtca   6000
cggccatcgt gtctacgttg cactacggag gcaagatgcg cacgaccaac ccgtgcaaca   6060
aacccataat catagacacc acaggacaga ccaagcccaa gccaggagac atcgtgttaa   6120
catgcttccg aggctgggca aagcagctgc agttggacta ccgtggacac gaagtcatga   6180
cagcagcagc atctcagggc ctcacccgca aggggtata cgccgtaagg cagaaggtga   6240
atgaaaatcc cttgtatgcc cctgcgtcgg agcacgtgaa tgtactgctg acgcgcactg   6300
aggataggct ggtgtggaaa acgctggccg gcgatccctg gattaaggtc ctatcaaaca   6360
ttccacaggg taactttacg gccacattgg aagaatggca agaagaacac gacaaaatag   6420
tgaaggtgat tgaaggaccg gctgcgcctg tggacgcgtt ccagaacaaa gcgaacgtgt   6480
gttgggcgaa aagcctggtg cctgtcctgg acactgccgg aatcagattg acagcagagg   6540
agtggagcac cataattaca gcatttaagg aggacagagc ttactctcca gtggtggcct   6600
tgaatgaaat ttgcaccaag tactatggag ttgacctgga cagtggcctg ttttctgccc   6660
cgaaggtgtc cctgtattac gagaacaacc actgggataa cagacctggt ggaaggatgt   6720
atggattcaa tgccgcaaca gctgccaggc tggaagctag acataccttc ctgaaggggc   6780
agtggcatac gggcaagcag gcagttatcg cagaaagaaa aatccaaccg ctttctgtgc   6840
tggacaatgt aattcctatc aaccgcaggc tgccgcacgc cctggtggct gagtacaaga   6900
cggttaaagg cagtagggtt gagtggctgg tcaataaagt aagagggtac cacgtcctgc   6960
tggtgagtga gtacaacctg gctttgcctc gacgcagggt cacttggttg tcaccgctga   7020
atgtcacagg cgccgatagg tgctacgacc taagtttagg actgccggct gacgccggca   7080
ggttcgactt ggtctttgtg aacattcaca cggaattcag aatccaccac taccagcagt   7140
gtgtcgacca cgccatgaag ctgcagatgc ttgggggaga tgcgctacga ctgctaaaac   7200
ccggcggcat cttgatgaga gcttacggat acgccgataa aatcagcgaa gccgttgttt   7260
cctccttaag cagaaagttc tcgtctgcaa gagtgttgcg cccggattgt gtcaccagca   7320
atacagaagt gttcttgctg ttctccaact ttgacaacgg aaagagaccc tctacgctac   7380
accagatgaa taccaagctg agtgccgtgt atgccggaga agccatgcac acggccgggt   7440
gtgcaccatc ctacagagtt aagagagcag acatagccac gtgcacagaa gcggctgtgg   7500
ttaacgcagc taacgcccgt ggaactgtag gggatgcgt atgcagggcc gtggcgaaga   7560
aatggccgtc agccttaag ggagcagcaa caccagtggg cacaattaaa acagtcatgt   7620
```

```
gcggctcgta ccccgtcatc cacgctgtag cgcctaattt ctctgccacg accagatatt    7680
cagatatttg aagcggaagg ggaccgcgaa ttggccgctg tctaccgggc agtggccgcc    7740
gaagtaaaca gactgtcact gagcagcgta gccatcccgc tgctgtccac aggagtgttc    7800
agcggcggaa gagataggct gcagcaatcc ctcaaccatc tattcacagc aatggacgcc    7860
acggacgctg acgtgaccat ctactgcaga gacaaaagtt gggagaagaa aatccaggaa    7920
gccattgaca tgaggacggc tgtggagttg ctcaatgatg acgtggagct gaccacagac    7980
ttggtgagag tgcacccgga cagcagcctg gtgggtcgta agggctacag taccactgac    8040
gggtcgctgt actcgtactt tgaaggtacg aaattcaacc aggctgctat tgatatggca    8100
gagatactga cgttgtggcc cagactgcaa gaggcaaacg aacagatatg cctatacgcg    8160
ctgggcgaaa caatggacaa catcagatcc aaatgtccgg tgaacgattc cgattcatca    8220
acacctccca ggacagtgcc ctgcctgtgc cgctacgcaa tgacagcaga acggatcgcc    8280
cgccttaggt cacaccaagt taaaagcatg gtggtttgct catcttttcc cctcccgaaa    8340
taccatgtag atggggtgca gaaggtaaag tgcgagaagg ttctcctgtt cgacccgacg    8400
gtaccttcag tggttagtcc gcggaagtat gccgcatcta cgacggacca ctcagatcgg    8460
tcgttacgag ggtttgactt ggactggacc accgactcgt cttccactgc cagcgatacc    8520
atgtcgctac ccagtttgca gtcgtgtgac atcgactcga tctacgagcc aatggctccc    8580
atagtagtga cggctgacgt acaccctgaa cccgcaggca tcgcggacct ggcggcagat    8640
gtgcaccctg aacccgcaga ccatgtggac ctcgagaacc cgattcctcc accgcgcccg    8700
aagagagctg cataccttgc ctcccgcgcg gcggagcgac cggtgccggc gccgagaaag    8760
ccgacgcctg ccccaaggac tgcgtttagg aacaagctgc ctttgacgtt cggcgacttt    8820
gacgagcacg aggtcgatgc gttggcctcc gggattactt tcggagactt cgacgacgtc    8880
ctgcgactag gccgcgcggg tgcatatatt ttctcctcgg acactggcag cggacattta    8940
caacaaaaat ccgttaggca gcacaatctc cagtgcgcac aactggatgc ggtccaggag    9000
gagaaaatgt acccgccaaa attggatact gagagggaga agctgttgct gctgaaaatg    9060
cagatgcacc catcggaggc taataagagt cgataccagt ctcgcaaagt ggagaacatg    9120
aaagccacgg tggtggacag gctcacatcg ggggccagat tgtacacggg agcggacgta    9180
ggccgcatac caacatacgc ggttcggtac ccccgccccg tgtactcccc taccgtgatc    9240
gaaagattct caagccccga tgtagcaatc gcagcgtgca acgaatacct atccagaaat    9300
tacccaacag tggcgtcgta ccagataaca gatgaatacg acgcatactt ggacatggtt    9360
gacgggtcgg atagttgctt ggacagagcg acattctgcc cggcgaagct ccggtgctac    9420
ccgaaacatc atgcgtacca ccagccgact gtacgcagtg ccgtcccgtc acccttttcag   9480 aacacactac agaacgtgct agcggccgcc accaagagaa actgcaacgt cacgcaaatg    9540
cgagaactac ccaccatgga ctcggcagtg ttcaacgtgg agtgcttcaa gcgctatgcc    9600
tgctccggag aatattggga agaatatgct aaacaaccta tccggataac cactgagaac    9660
atcactacct atgtgaccaa attgaaaggc ccgaaagctg ctgccttgtt cgctaagacc    9720
cacaacttgg ttccgctgca ggaggttccc atggacagat tcacggtcga catgaaacga    9780
gatgtcaaag tcactccagg gacgaaacac acagaggaaa gacccaaagt ccaggtaatt    9840
caagcagcgg agccattggc gaccgcttac ctgtgcggca tccacaggga attagtaagg    9900 agactaaaatg ctgtgttacg ccctaacgtg cacacattgt ttgatatgtc ggccgaagac    9960
```

-continued

```
tttgacgcga tcatcgcctc tcacttccac ccaggagacc cggttctaga gacggacatt   10020
gcatcattcg acaaaagcca ggacgactcc ttggctctta caggtttaat gatcctcgaa   10080
gatctagggg tggatcagta cctgctggac ttgatcgagg cagcctttgg ggaaatatcc   10140
agctgtcacc taccaactgg cacgcgcttc aagttcggag ctatgatgaa atcgggcatg   10200
tttctgactt tgtttattaa cactgttttg aacatcacca tagcaagcag ggtactggag   10260
cagagactca ctgactccgc ctgtgcggcc ttcatcggcg acgacaacat cgttcacgga   10320
gtgatctccg acaagctgat ggcggagagg tgcgcgtcgt gggtcaacat ggaggtgaag   10380
atcattgacg ctgtcatggg cgaaaaaccc ccatattttt gtgggggatt catagttttt   10440
gacagcgtca cacagaccgc ctgccgtgtt tcagacccac ttaagcgcct gttcaagttg   10500
ggtaagccgc taacagctga agacaagcag gacgaagaca ggcgacgagc actgagtgac   10560
gaggttagca agtggttccg gacaggcttg ggggccgaac tggaggtggc actaacatct   10620
aggtatgagg tagagggctg caaaagtatc ctcatagcca tggccacctt ggcgagggac   10680
attaaggcgt ttaagaaatt gagaggacct gttatacacc tctacgattt aaatgttatt   10740
ttccaccata ttgccgtctt ttggcaatgt gagggcccgg aaacctggcc ctgtcttctt   10800
gacgagcatt cctaggggtc tttcccctct cgccaaagga atgcaaggtc tgttgaatgt   10860
cgtgaaggaa gcagttcctc tggaagcttc ttgaagacaa acaacgtctg tagcgaccct   10920
ttgcaggcag cggaaccccc cacctggcga caggtgcctc tgcggccaaa agccacgtgt   10980
ataagataca cctgcaaagg cggcacaacc ccagtgccac gttgtgagtt ggatagttgt   11040
ggaaagagtc aaatggctct cctcaagcgt attcaacaag gggctgaagg atgcccagaa   11100
ggtaccccat tgtatgggat ctgatctggg gcctcggtgc acatgcttta catgtgttta   11160
gtcgaggtta aaaacgtct aggccccccg aaccacgggg acgtggtttt cctttatgaa   11220
aaagcctgaa ctcaccgcga cgtctgtcga aagtttctg atcgaaaagt cgacagcgt   11280 ctccgacctg atgcagctct cggagggcga agaatctcgt gctttcagct tcgatgtagg   11340
agggcgtgga tatgtcctgc gggtaaatag ctgcgccgat ggtttctaca aagatcgtta   11400
tgtttatcgg cactttgcat cggccgcgct cccgattccg gaagtgcttg acattgggga   11460
attcagcgag agcctgacct attgcatctc ccgccgtgca cagggtgtca cgttgcaaga   11520
cctgcctgaa accgaactgc cgctgttct gcagccggtc gcggaggcca tggatgcgat   11580
cgctgcggcc gatcttagcc agacgagcgg gttcggccca ttcggaccgc aaggaatcgg   11640
tcaatacact acatggcgtg atttcatatg cgcgattgct gatccccatg tgtatcactg   11700
gcaaactgtg atggacgaca ccgtcagtgc gtccgtcgcg caggctctcg atgagctgat   11760
gctttgggcc gaggactgcc ccgaagtccg gcacctcgtg cacgcggatt tcggctccaa   11820
caatgtcctg acggacaatg ccgcataac agcggtcatt gactggagcg aggcgatgtt   11880
cggggattcc caatacgagg tcgccaacat cttcttctgg aggccgtggt tggcttgtat   11940
ggagcagcag acgcgctact tcgagcggag gcatccggag cttgcaggat cgccgcggct   12000
ccgggcgtat atgctccgca ttggtcttga ccaactctat cagagcttgg ttgacggcaa   12060
tttcgatgat gcagcttggg cgcagggtcg atgcgacgca atcgtccgat ccggagccgg   12120
gactgtcggg cgtacacaaa tcgcccgcag aagcgcggcc gtctggaccg atggctgtgt   12180
agaagtactc gccgatagtg gaaaccgacg ccccagcact cgtccgaggg caaaggaaat   12240
ggtgagcaag ggcgaggagc tgttcaccgg ggtggtgccc atcctggtcg agctggacgg   12300
cgacgtaaac ggccacaagt tcagcgtgtc cggcgagggc gagggcgatg ccacctacgg   12360
```

| | |
|---|---:|
| caagctgacc ctgaagttca tctgcaccac cggcaagctg cccgtgccct ggcccaccct | 12420 |
| cgtgaccacc ctgacctacg gcgtgcagtg cttcagccgc tacccgacc acatgaagca | 12480 |
| gcacgacttc ttcaagtccg ccatgcccga aggctacgtc caggagcgca ccatcttctt | 12540 |
| caaggacgac ggcaactaca agacccgcgc cgaggtgaag ttcgagggcg acacccctggt | 12600 |
| gaaccgcatc gagctgaagg gcatcgactt caaggaggac ggcaacatcc tggggcacaa | 12660 |
| gctggagtac aactacaaca gccacaacgt ctatatcatg gccgacaagc agaagaacgg | 12720 |
| catcaaggtg aacttcaaga tccgccacaa catcgaggac ggcagcgtgc agctcgccga | 12780 |
| ccactaccag cagaacaccc ccatcggcga cggccccgtg ctgctgcccg acaaccacta | 12840 |
| cctgagcacc cagtccgccc tgagcaaaga ccccaacgag aagcgcgatc acatggtcct | 12900 |
| gctggagttc gtgaccgccg ccgggatcac tctcggcatg gacgagctgt acaag | 12955 |

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

| | |
|---|---:|
| aaaaaaaaaa aaaaaaaaaa aaaaaaaaaa ctagcataac cccttggggc ctctaaacgg | 60 |
| gtcttgaggg gttttttg | 78 |

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

| | |
|---|---:|
| taatacgact cactatagg | 19 |

<210> SEQ ID NO 4
<211> LENGTH: 481
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---:|
| gttatttccc accatattgc cgtcttttgg caatgtgagg gcccggaaac ctggccctgt | 60 |
| cttcttgacg agcattccta ggggtctttc ccctctcgcc aaaggaatgc aaggtctgtt | 120 |
| gaatgtcgtg aaggaagcag ttcctctgga agcttcttga agacaaacaa cgtctgtagc | 180 |
| gacccttttgc aggcagcgga accccccacc tggcgacagg tgcctctgcg gccaaaagcc | 240 |
| acgtgtataa gatacacctg caaaggcggc acaaccccag tgccacgttg tgagttggat | 300 |
| agttgtggaa agagtcaaat ggctctcctc aagcgtattc aacaagggc tgaaggatgc | 360 |
| ccagaaggta ccccattgta tgggatctga tctggggcct cggtgcacat gctttacatg | 420 |
| tgtttagtcg aggttaaaaa acgtctaggc ccccgaacc acgggacgt ggttttcctt | 480 |
| t | 481 |

<210> SEQ ID NO 5
<211> LENGTH: 7374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| atggcggatg | tgtgacatac | acgacgccaa | aagattttgt | tccagctcct | gccacctccg | 60 |
| ctacgcgaga | gattaaccac | ccacgatggc | cgccaaagtg | catgttgata | ttgaggctga | 120 |
| cagcccattc | atcaagtctt | tgcagaaggc | atttccgtcg | ttcgaggtgg | agtcattgca | 180 |
| ggtcacacca | aatgaccatg | caaatgccag | agcattttcg | cacctggcta | ccaaattgat | 240 |
| cgagcaggag | actgacaaag | acacactcat | cttggatatc | ggcagtgcgc | cttccaggag | 300 |
| aatgatgtct | acgcacaaat | accactgcgt | atgccctatg | cgcagcgcag | aagaccccga | 360 |
| aaggctcgat | agctacgcaa | agaaactggc | agcggcctcc | gggaaggtgc | tggatagaga | 420 |
| gatcgcagga | aaaatcaccg | acctgcagac | cgtcatggct | acgccagacg | ctgaatctcc | 480 |
| taccttttgc | ctgcatacag | acgtcacgtg | tcgtacggca | gccgaagtgg | ccgtatacca | 540 |
| ggacgtgtat | gctgtacatg | caccaacatc | gctgtaccat | caggcgatga | aaggtgtcag | 600 |
| aacggcgtat | tggattgggt | ttgacaccac | cccgtttatg | tttgacgcgc | tagcaggcgc | 660 |
| gtatccaacc | tacgccacaa | actgggccga | cgagcaggtg | ttacaggcca | ggaacatagg | 720 |
| actgtgtgca | gcatccttga | ctgagggaag | actcggcaaa | ctgtccattc | tccgcaagaa | 780 |
| gcaattgaaa | ccttgcgaca | cagtcatgtt | ctcggtagga | tctacattgt | acactgagag | 840 |
| cagaaagcta | ctgaggagct | ggcacttacc | ctccgtattc | cacctgaaag | gtaaacaatc | 900 |
| ctttacctgt | aggtgcgata | ccatcgtatc | atgtgaaggg | tacgtagtta | agaaaatcac | 960 |
| tatgtgcccc | ggcctgtacg | gtaaaacggt | agggtacgcc | gtgacgtatc | acgcggaggg | 1020 |
| attcctagtg | tgcaagacca | cagacactgt | caaaggagaa | agagtctcat | tccctgtatg | 1080 |
| cacctacgtc | ccctcaacca | tctgtgatca | aatgactggc | atactagcga | ccgacgtcac | 1140 |
| accggaggac | gcacagaagt | tgttagtggg | attgaatcag | aggatagttg | tgaacggaag | 1200 |
| aacacagcga | aacactaaca | cgatgaagaa | ctatctgctt | ccgattgtgg | ccgtcgcatt | 1260 |
| tagcaagtgg | gcgagggaat | acaaggcaga | ccttgatgat | gaaaaacctc | tgggtgtccg | 1320 |
| agagaggtca | cttacttgct | gctgcttgtg | ggcatttaaa | acgaggaaga | tgcacaccat | 1380 |
| gtacaagaaa | ccagacaccc | agacaatagt | gaaggtgcct | tcagagttta | actcgttcgt | 1440 |
| catcccgagc | ctatggtcta | caggcctcgc | aatcccagtc | agatcacgca | ttaagatgct | 1500 |
| tttggccaag | aagaccaagc | gagagttaat | acctgttctc | gacgcgtcgt | cagccaggga | 1560 |
| tgctgaacaa | gaggagaagg | agaggttgga | ggccgagctg | actagagaag | ccttaccacc | 1620 |
| cctcgtcccc | atcgcgccgg | cggagacggg | agtcgtcgac | gtcgacgttg | aagaactaga | 1680 |
| gtatcacgca | ggtgcagggg | tcgtggaaac | acctcgcagc | gcgttgaaag | tcaccgcaca | 1740 |
| gccgaacgac | gtactactag | gaaattacgt | agttctgtcc | ccgcagaccg | tgctcaagag | 1800 |
| ctccaagttg | gccccgtgc | accctctagc | agagcaggtg | aaaataataa | cacataacgg | 1860 |
| gagggccggc | ggttaccagg | tcgacggata | tgacggcagg | gtcctactac | catgtggatc | 1920 |
| ggccattccg | gtccctgagt | ttcaagcttt | gagcgagagc | gccactatgg | tgtacaacga | 1980 |
| aagggagttc | gtcaacagga | aactatacca | tattgccgtt | cacggaccgt | cgctgaacac | 2040 |
| cgacgaggag | aactacgaga | agtcagagc | tgaaagaact | gacgccgagt | acgtgttcga | 2100 |

```
cgtagataaa aaatgctgcg tcaagagaga ggaagcgtcg ggtttggtgt tggtgggaga    2160
gctaaccaac cccccgttcc atgaattcgc ctacgaaggg ctgaagatca ggccgtcggc    2220
accatataag actacagtag taggagtctt tggggttccg ggatcaggca agtctgctat    2280
tattaagagc ctcgtgacca aacacgatct ggtcaccagc ggcaagaagg agaactgcca    2340
ggaaatagtt aacgacgtga agaagcaccg cgggaagggg acaagtaggg aaaacagtga    2400
ctccatcctg ctaaacgggt gtcgtcgtgc cgtggacatc ctatatgtgg acgaggcttt    2460
cgctagccat tccggtactc tgctggccct aattgctctt gttaaacctc ggagcaaagt    2520
ggtgttatgc ggagacccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag ctgggcaaa gcagctgcag ttggactacc gtggacacga    2820
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag ataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta gtttaggac tgccggctga    3720 cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaattcct ctgccacgac    4320
cagatattca gatatttgaa gcggaagggg accgcgaatt ggccgctgtc taccgggcag    4380
tggccgccga agtaaacaga ctgtcactga gcagcgtagc catcccgctg ctgtccacag    4440
```

```
gagtgttcag cggcggaaga gataggctgc agcaatccct caaccatcta ttcacagcaa    4500
tggacgccac ggacgctgac gtgaccatct actgcagaga caaaagttgg gagaagaaaa    4560
tccaggaagc cattgacatg aggacggctg tggagttgct caatgatgac gtggagctga    4620
ccacagactt ggtgagagtg cacccggaca gcagcctggt gggtcgtaag ggctacagta    4680
ccactgacgg gtcgctgtac tcgtactttg aaggtacgaa attcaaccag gctgctattg    4740
atatggcaga gatactgacg ttgtggccca gactgcaaga ggcaaacgaa cagatatgcc    4800
tatacgcgct gggcgaaaca atggacaaca tcagatccaa atgtccggtg aacgattccg    4860
attcatcaac acctcccagg acagtgccct gcctgtgccg ctacgcaatg acagcagaac    4920
ggatcgcccg ccttaggtca caccaagtta aaagcatggt ggtttgctca tcttttcccc    4980
tcccgaaata ccatgtagat gggtgcaga aggtaaagtg cgagaaggtt ctcctgttcg      5040
acccgacggt accttcagtg gttagtccgc ggaagtatgc cgcatctacg acggaccact    5100
cagatcggtc gttacgaggg tttgacttgg actggaccac cgactcgtct tccactgcca    5160
gcgataccat gtcgctaccc agtttgcagt cgtgtgacat cgactcgatc tacgagccaa    5220
tggctcccat agtagtgacg gctgacgtac accctgaacc cgcaggcatc gcggacctgg    5280
cggcagatgt gcaccctgaa cccgcagacc atgtggacct cgagaacccg attcctccac    5340
cgcgcccgaa gagagctgca taccttgcct cccgcgcggc ggagcgaccg gtgccggcgc    5400
cgagaaagcc gacgcctgcc ccaaggactg cgtttaggaa caagctgcct ttgacgttcg    5460
gcgactttga cgagcacgag gtcgatgcgt tggcctccgg gattactttc ggagacttcg    5520
acgacgtcct gcgactaggc cgcgcgggtg catatatttt ctcctcggac actggcagcg    5580
gacatttaca acaaaaatcc gttaggcagc acaatctcca gtgcgcacaa ctggatgcgg    5640
tccaggagga gaaaatgtac ccgccaaaat tggatactga gagggagaag ctgttgctgc    5700
tgaaaatgca gatgcaccca tcggaggcta ataagagtcg ataccagtct cgcaaagtgg    5760
agaacatgaa agccacggtg gtggacaggc tcacatcggg ggccagattg tacacgggag    5820
cggacgtagg ccgcatacca acatacgcgg ttcggtaccc ccgccccgtg tactccccta    5880
ccgtgatcga aagattctca agccccgatg tagcaatcgc agcgtgcaac gaataccctat    5940 ccagaaatta cccaacagtg gcgtcgtacc agataacaga tgaatacgac gcatacttgg    6000
acatggttga cgggtcggat agttgcttgg acagagcgac attctgcccg gcgaagctcc    6060
ggtgctaccc gaaacatcat gcgtaccacc agccgactgt acgcagtgcc gtcccgtcac    6120
cctttcagaa cacactacag aacgtgctag cggccgccac caagagaaac tgcaacgtca    6180
cgcaaatgcg agaactaccc accatggact cggcagtgtt caacgtggag tgcttcaagc    6240
gctatgcctg ctccggagaa tatctgggaa gaatatgctaa caacctatc cggataacca    6300 ctgagaacat cactacctat gtgaccaaat tgaaaggccc gaaagctgct gccttgttcg    6360
ctaagaccca caacttggtt ccgctgcagg aggttcccat ggacagattc acggtcgaca    6420
tgaaacgaga tgtcaaagtc actccaggga cgaaacacac agaggaaaga cccaaagtcc    6480
aggtaattca agcagcggag ccattggcga ccgcttacct gtgcggcatc cacagggaat    6540
tagtaaggag actaaatgct gtgttacgcc ctaacgtgca cattgtttt gatatgtcgg      6600 ccgaagactt tgacgcgatc atcgcctctc acttccaccc aggagacccg gttctagaga    6660
cggacattgc atcattcgac aaaagccagg acgactcctt ggctcttaca ggtttaatga    6720
tcctcgaaga tctaggggtg gatcagtacc tgctggactt gatcgaggca gccttt gggg    6780 aaatatccag ctgtcaccta ccaactggca cgcgcttcaa gttcggagct atgatgaaat    6840
```

```
cgggcatgtt tctgactttg tttattaaca ctgttttgaa catcaccata gcaagcaggg    6900
tactggagca gagactcact gactccgcct gtgcggcctt catcggcgac gacaacatcg    6960
ttcacggagt gatctccgac aagctgatgg cggagaggtg cgcgtcgtgg gtcaacatgg    7020
aggtgaagat cattgacgct gtcatgggcg aaaaaccccc atattttgt gggggattca     7080 tagttttga cagcgtcaca cagaccgcct gccgtgtttc agacccactt aagcgcctgt     7140
tcaagttggg taagccgcta acagctgaag acaagcagga cgaagacagg cgacgagcac    7200
tgagtgacga ggttagcaag tggttccgga caggcttggg ggccgaactg gaggtggcac    7260
taacatctag gtatgaggta gagggctgca aaagtatcct catagccatg ccaccttgg     7320 cgagggacat taaggcgttt aagaaattga gaggacctgt tatacacctc tacg          7374
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

```
attgagagga cctgttatac acct                                             24
```

<210> SEQ ID NO 7
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atgaaaaagc ctgaactcac cgcgacgtct gtcgagaagt ttctgatcga aaagttcgac    60
agcgtctccg acctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag gtcgatgcgc acgcaatcgt ccgatccgga    900
gccgggactg tcgggcgtac acaaatcgcc cgcagaagcg cggccgtctg gaccgatggc    960
tgtgtagaag tactcgccga tagtggaaac gacgcccca gcactcgtcc gagggcaaag    1020
gaaatggtga gcaagggcga ggagctgttc accggggtgg tgcccatcct ggtcgagctg    1080
```

| | | |
|---|---|---|
| gacggcgacg | taaacggcca caagttcagc gtgtccggcg agggcgaggg cgatgccacc | 1140 |
| tacggcaagc | tgaccctgaa gttcatctgc accaccggca agctgcccgt gccctggccc | 1200 |
| accctcgtga | ccaccctgac ctacggcgtg cagtgcttca gccgctaccc cgaccacatg | 1260 |
| aagcagcacg | acttcttcaa gtccgccatg cccgaaggct acgtccagga gcgcaccatc | 1320 |
| ttcttcaagg | acgacggcaa ctacaagacc cgcgccgagg tgaagttcga gggcgacacc | 1380 |
| ctggtgaacc | gcatcgagct gaagggcatc gacttcaagg aggacggcaa catcctgggg | 1440 |
| cacaagctgg | agtacaacta caacagccac aacgtctata tcatggccga caagcagaag | 1500 |
| aacggcatca | aggtgaactt caagatccgc cacaacatcg aggacggcag cgtgcagctc | 1560 |
| gccgaccact | accagcagaa cacccccatc ggcgacggcc ccgtgctgct gcccgacaac | 1620 |
| cactacctga | gcacccagtc cgccctgagc aaagacccca acgagaagcg cgatcacatg | 1680 |
| gtcctgctgg | agttcgtgac cgccgccggg atcactctcg gcatggacga gctgtacaag | 1740 |

<210> SEQ ID NO 8
<211> LENGTH: 18073
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | | |
|---|---|---|
| atgaaaaagc | tgaactcac cgcgacgtct gtcgagaagt ttctgatcga aaagttcgac | 60 |
| agcgtctccg | acctgatgca gctctcggag ggcgaagaat ctcgtgcttt cagcttcgat | 120 |
| gtaggagggc | gtggatatgt cctgcgggta aatagctgcg ccgatggttt ctacaaagat | 180 |
| cgttatgttt | atcggcactt tgcatcggcc gcgctcccga ttccggaagt gcttgacatt | 240 |
| ggggaattca | gcgagagcct gacctattgc atctcccgcc gtgcacaggg tgtcacgttg | 300 |
| caagacctgc | ctgaaaccga actgcccgct gttctgcagc cggtcgcgga ggccatggat | 360 |
| gcgatcgctg | cggccgatct tagccagacg agcgggttcg gcccattcgg accgcaagga | 420 |
| atcggtcaat | acactacatg gcgtgatttc atatgcgcga ttgctgatcc ccatgtgtat | 480 |
| cactggcaaa | ctgtgatgga cgacaccgtc agtgcgtccg tcgcgcaggc tctcgatgag | 540 |
| ctgatgcttt | gggccgagga ctgccccgaa gtccggcacc tcgtgcacgc ggatttcggc | 600 |
| tccaacaatg | tcctgacgga caatggccgc ataacagcgg tcattgactg gagcgaggcg | 660 |
| atgttcgggg | attcccaata cgaggtcgcc aacatcttct tctggaggcc gtggttggct | 720 |
| tgtatggagc | agcagacgcg ctacttcgag cggaggcatc cggagcttgc aggatcgccg | 780 |
| cggctccggg | cgtatatgct ccgcattggt cttgaccaac tctatcagag cttggttgac | 840 |
| ggcaatttcg | atgatgcagc ttgggcgcag gtcgatgcg acgcaatcgt ccgatccgga | 900 |
| gccgggactg | tcgggcgtac acaaatcgcc cgcagaagcg cggccgtctg gaccgatggc | 960 |
| tgtgtagaag | tactcgccga tagtggaaac cgacgcccca gcactcgtcc gagggcaaag | 1020 |
| gaaatggtga | gcaagggcga ggagctgttc accggggtgg tgcccatcct ggtcgagctg | 1080 |
| gacggcgacg | taaacggcca caagttcagc gtgtccggcg agggcgaggg cgatgccacc | 1140 |
| tacggcaagc | tgaccctgaa gttcatctgc accaccggca agctgcccgt gccctggccc | 1200 |
| accctcgtga | ccaccctgac ctacggcgtg cagtgcttca gccgctaccc cgaccacatg | 1260 |
| aagcagcacg | acttcttcaa gtccgccatg cccgaaggct acgtccagga gcgcaccatc | 1320 |
| ttcttcaagg | acgacggcaa ctacaagacc cgcgccgagg tgaagttcga gggcgacacc | 1380 |

```
ctggtgaacc gcatcgagct gaagggcatc gacttcaagg aggacggcaa catcctgggg    1440
cacaagctgg agtacaacta caacagccac aacgtctata tcatggccga caagcagaag    1500
aacggcatca aggtgaactt caagatccgc cacaacatcg aggacggcag cgtgcagctc    1560
gccgaccact accagcagaa cacccccatc ggcgacggcc ccgtgctgct gcccgacaac    1620
cactacctga gcacccagtc cgccctgagc aaagacccca acgagaagcg cgatcacatg    1680
gtcctgctgg agttcgtgac cgccgccggg atcactctcg gcatggacga gctgtacaag    1740
gggcggccgc aaaaaaaaaa aaaaaaaaa aaaaaaaaa ctagcataac cccttggggc    1800
ctctaaacgg gtcttgaggg gttttttgga tccgggctgg cgtaatagcg aagaggcccg    1860
caccgatcgc ccttcccaac agttgcgcag cctgaatggc gaatgacgc gccctgtagc    1920 ggcgcattaa gcgcggcggg tgtggtggtt acgcgcagcg tgaccgctac acttgccagc    1980
gccctagcgc ccgctccttt cgctttcttc ccttcctttc tcgccacgtt cgccggcttt    2040
ccccgtcaag ctctaaatcg ggggctccct ttagggttcc gatttagtgc tttacggcac    2100
ctcgacccca aaaaacttga ttagggtgat ggttcacgta gtgggccatc gccctgatag    2160 acggttttc gcccttttgac gttggagtcc acgttcttta atagtggact cttgttccaa    2220 actgaacaa cactcaaccc tatctcggtc tattcttttg atttataagg gattttgccg    2280
atttcggcct attggttaaa aaatgagctg atttaacaaa aatttaacgc gaattttaac    2340
aaaatattaa cgcttacaat ttcctgatgc ggtattttct ccttacgcat ctgtgcggta    2400
tttcacaccg catatggtgc actctcagta caatctgctc tgatgccgca tagttaagcc    2460
agccccgaca cccgccaaca cccgctgacg cgccctgacg ggcttgtctg ctcccggcat    2520
ccgcttacag acaagctgtg accgtctccg ggagctgcat gtgtcagagg ttttcaccgt    2580
catcaccgaa acgcgcgaga cgaaagggcc tcgtgatacg cctatttta taggttaatg    2640 tcatgataat aatggtttct tagacgtcag gtggcacttt tcggggaaat gtgcgcggaa    2700
cccctatttg tttatttttc taaatacatt caaatatgta tccgctcatg agacaataac    2760
cctgataaat gcttcaataa tattgaaaaa ggaagagtat gagtattcaa catttccgtg    2820
tcgcccttat tcccttttttt gcggcatttt gccttcctgt ttttgctcac ccagaaacgc    2880
tggtgaaagt aaaagatgct gaagatcagt tgggtgcacg agtgggttac atcgaactgg    2940
atctcaacag cggtaagatc cttgagagtt ttcgccccga agaacgtttt ccaatgatga    3000 gcactttaa agttctgcta tgtggcgcgg tattatcccg tattgacgcc gggcaagagc    3060
aactcggtcg ccgcatacac tattctcaga atgacttggt tgagtactca ccagtcacag    3120
aaaagcatct tacggatggc atgacagtaa gagaattatg cagtgctgcc ataaccatga    3180
gtgataacac tgcggccaac ttacttctga caacgatcgg aggaccgaag gagctaaccg    3240
cttttttgca acatggggg gatcatgtaa ctcgccttga tcgttgggaa ccggagctga    3300
atgaagccat accaaacgac gagcgtgaca ccacgatgcc tgtagcaatg gcaacaacgt    3360
tgcgcaaact attaactggc gaactactta ctctagcttc ccggcaacaa ttaatagact    3420
ggatggaggc ggataaagtt gcaggaccac ttctgcgctc ggcccttccg gctggctggt    3480
ttattgctga taaatctgga gccggtgagc gtgggtctcg cggtatcatt gcagcactgg    3540
ggccagatgg taagccctcc cgtatcgtag ttatctacac gacggggagt caggcaacta    3600
tggatgaacg aaatagacag atcgctgaga taggtgcctc actgattaag cattggtaac    3660
tgtcagacca agtttactca tatatacttt agattgattt aaaacttcat ttttaattta    3720
aaaggatcta ggtgaagatc ctttttgata atctcatgac caaaatccct taacgtgagt    3780
```

```
tttcgttcca ctgagcgtca gaccccgtag aaaagatcaa aggatcttct tgagatcctt    3840
tttttctgcg cgtaatctgc tgcttgcaaa caaaaaaacc accgctacca gcggtggttt    3900
gtttgccgga tcaagagcta ccaactcttt ttccgaaggt aactggcttc agcagagcgc    3960
agataccaaa tactgttctt ctagtgtagc cgtagttagg ccaccacttc aagaactctg    4020
tagcaccgcc tacatacctc gctctgctaa tcctgttacc agtggctgct gccagtggcg    4080
ataagtcgtg tcttaccggg ttggactcaa gacgatagtt accggataag cgcagcggt    4140 cgggctgaac ggggggttcg tgcacacagc ccagcttgga gcgaacgacc tacaccgaac    4200
tgagatacct acagcgtgag ctatgagaaa gcgccacgct tcccgaaggg agaaaggcgg    4260
acaggtatcc ggtaagcggc agggtcggaa caggagagcg cacgagggag cttccagggg    4320
gaaacgcctg gtatctttat agtcctgtcg ggtttcgcca cctctgactt gagcgtcgat    4380
ttttgtgatg ctcgtcaggg gggcggagcc tatggaaaaa cgccagcaac gcggcctttt    4440
tacggttcct ggccttttgc tggccttttg ctcacatggc tcgacagatc ttaaggctag    4500
agtacttaat acgactcact ataggctagc atttaggtga cactatagaa tacaagctac    4560
ttgttctttt tgcactcgag aattcacgcg tggtacctct agagtcgacc cgttattttc    4620
caccatattg ccgtcttttg gcaatgtgag ggcccggaaa cctggccctg tcttcttgac    4680
gagcattcct aggggtcttt cccctctcgc caaggaatg caaggtctgt tgaatgtcgt    4740
gaaggaagca gttcctctgg aagcttcttg aagacaaaca acgtctgtag cgaccctttg    4800
caggcagcgg aaccccccac ctggcgacag gtgcctctgc ggccaaaagc cacgtgtata    4860
agatacacct gcaaaggcgg cacaacccca gtgccacgtt gtgagttgga tagttgtgga    4920
aagagtcaaa tggctctcct caagcgtatt caacaagggg ctgaaggatg cccagaaggt    4980
accccattgt atgggatctg atctggggcc tcggtgcaca tgctttacat gtgtttagtc    5040
gaggttaaaa aacgtctagg ccccccgaac cacggggacg tggttttcct ttatggcgga    5100
tgtgtgacat acacgacgcc aaaagatttt gttccagctc ctgccacctc cgctacgcga    5160
gagattaacc acccacgatg gccgccaaag tgcatgttga tattgaggct gacagcccat    5220
tcatcaagtc tttgcagaag gcatttccgt cgttcgaggt ggagtcattg caggtcacac    5280
caaatgacca tgcaaatgcc agagcatttt cgcacctggc taccaaattg atcgagcagg    5340
agactgacaa agacacactc atcttggata tcggcagtgc gccttccagg agaatgatgt    5400
ctacgcacaa ataccactgc gtatgcccta tgcgcagcgc agaagacccc gaaaggctcg    5460
atagctacga aaagaaactg gcagcggcct ccgggaaggt gctggataga gagatcgcag    5520
gaaaaatcac cgacctgcag accgtcatgg ctacgccaga cgctgaatct cctacctttt    5580
gcctgcatac agacgtcacg tgtcgtacgg cagccgaagt ggccgtatac caggacgtgt    5640
atgctgtaca tgcaccaaca tcgctgtacc atcaggcgat gaaaggtgtc agaacggcgt    5700
attggattgg gtttgacacc accccgttta tgtttgacgc gctagcaggc gcgtatccaa    5760
cctacgccac aaactgggcc gacgagcagg tgttacaggc caggaacata ggactgtgtg    5820
cagcatcctt gactgaggga agactcggca aactgtccat tctccgcaag aagcaattga    5880
aaccttgcga cacagtcatg ttctcggtag gatctacatt gtacactgag agcagaaagc    5940
tactgaggag ctggcactta ccctccgtat tccacctgaa aggtaaacaa tcctttacct    6000
gtaggtgcga taccatcgta tcatgtgaag ggtacgtagt taagaaaatc actatgtgcc    6060
ccggcctgta cggtaaaacg gtagggtacg ccgtgacgta tcacgcggag ggattcctag    6120
```

```
tgtgcaagac cacagacact gtcaaaggag aaagagtctc attccctgta tgcacctacg   6180 tccccctcaac catctgtgat caaatgactg gcatactagc gaccgacgtc acaccggagg   6240
acgcacagaa gttgttagtg ggattgaatc agaggatagt tgtgaacgga agaacacagc   6300
gaaacactaa cacgatgaag aactatctgc ttccgattgt ggccgtcgca tttagcaagt   6360
gggcgaggga atacaaggca gaccttgatg atgaaaaacc tctgggtgtc cgagagaggt   6420
cacttacttg ctgctgcttg tgggcattta aaacgaggaa gatgcacacc atgtacaaga   6480
aaccagacac ccagacaata gtgaaggtgc cttcagagtt taactcgttc gtcatcccga   6540
gcctatggtc tacaggcctc gcaatcccag tcagatcacg cattaagatg cttttggcca   6600
agaagaccaa gcgagagtta atacctgttc tcgacgcgtc gtcagccagg gatgctgaac   6660
aagaggagaa ggagaggttg gaggccgagc tgactagaga agccttacca cccctcgtcc   6720
ccatcgcgcc ggcggagacg ggagtcgtcg acgtcgacgt tgaagaacta gagtatcacg   6780
caggtgcagg ggtcgtggaa acacctcgca gcgcgttgaa agtcaccgca cagccgaacg   6840
acgtactact aggaaattac gtagttctgt ccccgcagac cgtgctcaag agctccaagt   6900
tggcccccgt gcaccctcta gcagagcagg tgaaaataat aacacataac gggagggccg   6960
gcggttacca ggtcgacgga tatgacggca gggtcctact accatgtgga tcggccattc   7020
cggtccctga gtttcaagct ttgagcgaga gcgccactat ggtgtacaac gaaagggagt   7080
tcgtcaacag gaaactatac catattgccg ttcacggacc gtcgctgaac accgacgagg   7140
agaactacga gaaagtcaga gctgaaagaa ctgacgccga gtacgtgttc gacgtagata   7200
aaaaatgctg cgtcaagaga gaggaagcgt cgggtttggt gttggtggga gagctaacca   7260 acccccccgtt ccatgaattc gcctacgaag ggctgaagat caggccgtcg gcaccatata   7320
agactacagt agtaggagtc tttggggttc cgggatcagg caagtctgct attattaaga   7380
gcctcgtgac caaacacgat ctggtcacca gcggcaagaa ggagaactgc caggaaatag   7440
ttaacgacgt gaagaagcac cgcgggaagg ggacaagtag ggaaaacagt gactccatcc   7500
tgctaaacgg gtgtcgtcgt gccgtggaca tcctatatgt ggacgaggct ttcgctagcc   7560
attccggtac tctgctggcc ctaattgctc ttgttaaacc tcggagcaaa gtggtgttat   7620
gcggagaccc caagcaatgc ggattcttca atatgatgca gcttaaggtg aacttcaacc   7680
acaacatctg cactgaagta tgtcataaaa gtatatccag acgttgcacg cgtccagtca   7740
cggccatcgt gtctacgttg cactacggag gcaagatgcg cacgaccaac ccgtgcaaca   7800
aacccataat catagacacc acaggacaga ccaagcccaa gccaggagac atcgtgttaa   7860
catgcttccg aggctgggca aagcagctgc agttggacta ccgtggacac gaagtcatga   7920
cagcagcagc atctcagggc ctcacccgca aaggggtata cgccgtaagg cagaaggtga   7980
atgaaaatcc cttgtatgcc cctgcgtcgg agcacgtgaa tgtactgctg acgcgcactg   8040
aggataggct ggtgtggaaa acgctggccg gcgatccctg gattaaggtc ctatcaaaca   8100
ttccacaggg taactttacg gccacattgg aagaatggca agaagaacac gacaaaatac   8160
tgaaggtgat tgaaggaccg gctgcgcctg tggacgcgtt ccagaacaaa gcgaacgtgt   8220
gttgggcgaa aagcctggtg cctgtcctgg acactgccgg aatcagattg acagcagagg   8280
agtggagcac cataattaca gcatttaagg aggacagagc ttactctcca gtggtggcct   8340
tgaatgaaat ttgcaccaag tactatggag ttgacctgga cagtggcctg ttttctgccc   8400
cgaaggtgtc cctgtattac gagaacaacc actgggataa cagacctggt ggaaggatgt   8460
atggattcaa tgccgcaaca gctgccaggc tggaagctag acatacgttc ctgaagggc   8520
```

```
agtggcatac gggcaagcag gcagttatcg cagaaagaaa aatccaaccg ctttctgtgc    8580
tggacaatgt aattcctatc aaccgcaggc tgccgcacgc cctggtggct gagtacaaga    8640
cggttaaagg cagtagggtt gagtggctgg tcaataaagt aagagggtac cacgtcctgc    8700
tggtgagtga gtacaacctg gctttgcctc gacacagggt cacttggttg tcaccgctga    8760
atgtcacagg cgccgatagg tgctacgacc taagtttagg actgccggct gacgccggca    8820
ggttcgactt ggtctttgtg aacattcaca cggaattcag aatccaccac taccagcagt    8880
gtgtcgacca cgccatgaag ctgcagatgc ttgggggaga tgcgctacga ctgctaaaaa    8940
ccggcggcat cttgatgaga gcttacggat acgccgataa aatcagcgaa gccgttgttt    9000
cctccttaag cagaaagttc tcgtctgcaa gagtgttgcg cccggattgt gtcaccagca    9060
atacagaagt gttcttgctg ttctccaact ttgacaacgg aaagagaccc tctacgctac    9120
accagatgaa taccaagctg agtgccgtgt atgccggaga agccatgcac acggccgggt    9180
gtgcaccatc ctacagagtt aagagagcag acatagccac gtgcacagaa gcggctgtgg    9240
ttaacgcagc taacgcccgt ggaactgtag gggatggcgt atgcagggcc gtggcgaaga    9300
aatggccgtc agcctttaag ggagcagcaa caccagtggg cacaattaaa acagtcatgt    9360
gcggctcgta ccccgtcatc cacgctgtag cgcctaattt ctctgccacg accagatatt    9420
cagatatttg aagcggaagg ggaccgcgaa ttggccgctg tctaccgggc agtgccgcc    9480 gaagtaaaca gactgtcact gagcagcgta gccatcccgc tgctgtccac aggagtgttc    9540
agcggcggaa gagataggct gcagcaatcc ctcaaccatc tattcacagc aatggacgcc    9600
acggacgctg acgtgaccat ctactgcaga gacaaaagtt gggagaagaa aatccaggaa    9660
gccattgaca tgaggacggc tgtggagttg ctcaatgatg acgtggagct gaccacagac    9720
ttggtgagag tgcacccgga cagcagcctg gtgggtcgta agggctacag taccactgac    9780
gggtcgctgt actcgtactt tgaaggtacg aaattcaacc aggctgctat tgatatggca    9840
gagatactga cgttgtggcc cagactgcaa gaggcaaacg aacagatatg cctatacgcg    9900
ctgggcgaaa caatgacaa catcagatcc aaatgtccgg tgaacgattc cgattcatca    9960
acacctccca ggacagtgcc ctgcctgtgc cgctacgcaa tgacagcaga acggatcgcc    10020
cgccttaggt cacaccaagt taaaagcatg gtggtttgct catcttttcc cctcccgaaa    10080
taccatgtag atggggtgca gaaggtaaag tgcgagaagg ttctcctgtt cgacccgacg    10140
gtaccttcag tggttagtcc gcggaagtat gccgcatcta cgacggacca ctcagatcgg    10200
tcgttacgag ggtttgactt ggactggacc accgactcgt cttccactgc agcgatacc    10260 atgtcgctac ccagtttgca gtcgtgtgac atcgactcga tctacgagcc aatggctccc    10320
atagtagtga cggctgacgt acaccctgaa cccgcaggca tcgcggacct ggcggcagat    10380
gtgcaccctg aacccgcaga ccatgtggac ctcgagaacc cgattcctcc accgcgcccg    10440
aagagagctg cataccttgc ctcccgcgcg cggagcgac cggtgccggc gccgagaaag    10500
ccgacgcctg ccccaaggac tgcgtttagg aacaagctgc ctttgacgtt cggcgacttt    10560
gacgagcacg aggtcgatgc gttggcctcc gggattactt tcggagactt cgacgacgtc    10620
ctgcgactag gccgcgcggg tgcatatatt ttctcctcgg acactggcag cggacattta    10680
caacaaaaat ccgttaggca gcacaatctc cagtgcgcac aactggatgc ggtccaggag    10740
gagaaaatgt acccgccaaa attggatact gagagggaga agctgttgct gctgaaaatg    10800
cagatgcacc catcggaggc taataagagt cgataccagt ctcgcaaagt ggagaacatg    10860
```

-continued

```
aaagccacgg tggtggacag gctcacatcg ggggccagat tgtacacggg agcggacgta    10920
ggccgcatac caacatacgc ggttcggtac ccccgccccg tgtactcccc taccgtgatc    10980
gaaagattct caagccccga tgtagcaatc gcagcgtgca acgaatacct atccagaaat    11040
tacccaacag tggcgtcgta ccagataaca gatgaatacg acgcatactt ggacatggtt    11100
gacgggtcgg atagttgctt ggacagagcg acattctgcc cggcgaagct ccggtgctac    11160
ccgaaacatc atgcgtacca ccagccgact gtacgcagtg ccgtcccgtc acccttcag     11220
aacacactac agaacgtgct agcggccgcc accaagagaa actgcaacgt cacgcaaatg    11280
cgagaactac ccaccatgga ctcggcagtg ttcaacgtgg agtgcttcaa gcgctatgcc    11340
tgctccggag aatattggga agaatatgct aaacaaccta tccggataac cactgagaac    11400
atcactacct atgtgaccaa attgaaaggc ccgaaagctg ctgccttgtt cgctaagacc    11460
cacaacttgg ttccgctgca ggaggttccc atggacagat tcacggtcga catgaaacga    11520
gatgtcaaag tcactccagg gacgaaacac acagaggaaa gacccaaagt ccaggtaatt    11580
caagcagcgg agccattggc gaccgcttac ctgtgcggca tccacaggga attagtaagg    11640
agactaaatg ctgtgttacg ccctaacgtg cacacattgt ttgatatgtc ggccgaagac    11700
tttgacgcga tcatcgcctc tcacttccac ccaggagacc cggttctaga cggacatt     11760
gcatcattcg acaaaagcca ggacgactcc ttggctctta caggtttaat gatcctcgaa    11820
gatctagggg tggatcagta cctgctggac ttgatcgagg cagcctttgg ggaaatatcc    11880
agctgtcacc taccaactgg cacgcgcttc aagttcggag ctatgatgaa atcgggcatg    11940
tttctgactt tgtttattaa cactgtttg aacatcacca tagcaagcag ggtactggag     12000
cagagactca ctgactccgc ctgtgcggcc ttcatcggcg acgacaacat cgttcacgga    12060
gtgatctccg acaagctgat ggcggagagg tgcgcgtcgt gggtcaacat ggaggtgaag    12120
atcattgacg ctgtcatggg cgaaaaaccc ccatatttt gtgggggatt catagttttt     12180
gacagcgtca cacagaccgc ctgccgtgtt tcagacccac ttaagcgcct gttcaagttg    12240
ggtaagccgc taacagctga agacaagcag gacgaagaca ggcgacgagc actgagtgac    12300
gaggttagca agtggttccg gacaggcttg ggggccgaac tggaggtggc actaacatct    12360
aggtatgagg tagagggctg caaaagtatc ctcatagcca tggccacctt ggcgagggac    12420
attaaggcgt ttaagaaatt gagaggacct gttatacacc tctacgaatt catgctgtc     12480
agcgacgctc tgctcccgtc cttctccacg ttcgcgtccg gccggcggg aagggagaag     12540
acactgcgtc cagcaggtgc cccgactaac cgttggcgtg aggaactctc tcacatgaag    12600
cgacttcccc cacttcccgg ccgcccctac gacctggcgg cgacggtggc cacagacctg    12660
gagagtggcg gagctggtgc agcttgcagc agtaacaacc cggccctcct agcccggagg    12720
gagaccgagg agttcaacga cctcctggac ctagacttta tcctttccaa ctcgctaacc    12780
caccaggaat cggtggccgc caccgtgacc acctcggcgt cagcttcatc ctcgtcttcc    12840
ccggcgagca gcggccctgc cagcgcgccc tccacctgca gcttcagcta tccgatccgg    12900
gccggggtg accgggcgt ggctgccagc aacacaggtg gagggctcct ctacagccga      12960
gaatctgcgc cacctcccac ggcccccttc aacctggcgg acatcaatga cgtgagcccc    13020
tcggcggct tcgtggctga gctcctgcgg ccggagttgg acccagtata cattccgcca     13080
cagcagcctc agccgccagg tggcgggctg atgggcaagt ttgtgctgaa ggcgtctctg    13140
accaccctg gcagcgagta cagcagccct tcggtcatca gtgttagcaa aggaagccca    13200
gacggcagcc accccgtggt agtggcgccc tacagcggtg gcccgccgcg catgtgcccc    13260
```

```
aagattaagc aagaggcggt cccgtcctgc acggtcagcc ggtccctaga ggcccatttg   13320
agcgctggac cccagctcag caacggccac cggcccaaca cacacgactt cccctgggg    13380 cggcagctcc ccaccaggac taccctaca ctgagtcccg aggaactgct gaacagcagg    13440
gactgtcacc ctggcctgcc tcttccccca ggattccatc cccatccggg cccaactac    13500 cctcctttcc tgccagacca gatgcagtca caagtccct ctctccatta tcaagagctc     13560
atgccaccgg gttcctgcct gccagaggag cccaagccaa agaggggaag aaggtcgtgg   13620
ccccggaaaa gaacagccac ccacacttgt gactatgcag gctgtggcaa aacctatacc   13680
aagagttctc atctcaaggc acacctgcga actcacacag gcgagaaacc ttaccactgt   13740
gactgggacg gctgtgggtg gaaattcgcc cgctccgatg aactgaccag gcactaccgc   13800
aaacacacag gcaccggcc ctttcagtgc cagaagtgtg acagggcctt ttccaggtcg     13860
gaccaccttg ccttacacat gaagaggcac tttcgcgcca gcgcggctc cggccagtgc    13920 accaactacg ccctgctgaa gctggccggc gacgtggagt ccaaccccgg ccccgctgga   13980
cacctggctt cagacttcgc cttctcaccc ccaccaggtg ggggtgatgg gtcagcaggg   14040
ctggagccgg gctgggtgga tcctcgaacc tggctaagct tccaagggcc tccaggtggg   14100
cctggaatcg gaccaggctc agaggtattg gggatctccc catgtccgcc cgcatacgag   14160
ttctgcggag ggatggcata ctgtggacct caggttggac tgggcctagt cccccaagtt   14220
ggcgtggaga ctttgcagcc tgagggccag gcaggagcac gagtggaaag caactcagag   14280
ggaacctcct ctgagccctg tgccgaccgc cccaatgccg tgaagttgga gaaggtggaa   14340
ccaactcccg aggagtccca ggacatgaaa gccctgcaga aggagctaga acagtttgcc   14400
aagctgctga agcagaagag gatcaccttg gggtacaccc aggccgacgt ggggctcacc   14460
ctgggcgttc tctttggaaa ggtgttcagc cagaccacca tctgtcgctt cgaggccttg   14520
cagctcagcc ttaagaacat gtgtaagctg cggcccctgc tggagaagtg ggtggaggaa   14580
gccgacaaca atgagaacct tcaggagata tgcaaatcgg agaccctggt gcaggcccgg   14640
aagagaaagc gaactagcat tgagaaccgt gtgaggtgga gtctggagac catgtttctg   14700
aagtgcccga agccctccct acagcagatc actcacatcg ccaatcagct tgggctagag   14760
aaggatgtgg ttcgagtatg gttctgtaac cggcgccaga agggcaaaag atcaagtatt   14820
gagtattccc aacgagaaga gtatgaggct acagggacac ctttcccagg gggggctgta   14880
tcctttcctc tgcccccagg tccccacttt ggcaccccag gctatggaag ccccacttc    14940 accacactct actcagtccc ttttcctgag ggcgaggcct ttccctctgt tcccgtcact   15000
gctctgggct ctcccatgca ttcaaaccgc gccaagcgcg gctccggcga gggcagagga   15060
agtcttctaa catgcggtga cgtggaggag aatcccggcc cttataacat gatggagacg   15120
gagctgaagc cgccgggccc gcagcaagct tcggggggcg gcggcggagg aggcaacgcc   15180
acggcggcgg cgaccggcgg caaccagaag aacagcccgg accgcgtcaa gaggcccatg   15240
aacgccttca tggtatggtc ccgggggcag cggcgtaaga tggcccagga gaaccccaag   15300
atgcacaact cggagatcag caagcgcctg ggcgcggagt ggaaactttt gtccgagacc   15360
gagaagcggc cgttcatcga cgaggccaag cggctgcgcg ctctgcacat gaaggagcac   15420
ccggattata ataccggcc gcggcgaaaa accaagacgc tcatgaagaa ggataagtac   15480
acgcttcccg gaggcttgct ggcccccggc gggaacagca tggcgagcgg ggttgggtgg   15540
ggcgccggcc tgggtgcggg cgtgaaccag cgcatggaca gctacgcgca catgaacggc   15600
```

```
tggagcaacg gcagctacag catgatgcag gagcagctgg gctacccgca gcacccgggc    15660
ctcaacgctc acggcgcggc acagatgcaa ccgatgcacc gctacgacgt cagcgccctg    15720
cagtacaact ccatgaccag ctcgcagacc tacatgaacg gctcgcccac ctacagcatg    15780
tcctactcgc agcagggcac ccccggtatg gcgctgggct ccatgggctc tgtggtcaag    15840
tccgaggcca gctccagccc ccccgtggtt acctcttcct cccactccag ggcgccctgc    15900
caggccgggg acctccggga catgatcagc atgtacctcc ccggcgccga ggtgccggag    15960
cccgctgcgc ccagtagact gcacatggcc cagcactacc agagcggccc ggtgcccggc    16020
acggccatta acggcacact gccectgtcg cacatgcgcg ccaagcgcgg ctccggcgcc    16080
accaacttct ccctgctgaa gcaggccggc gacgtggagg agaaccccgg ccccccctc    16140 aacgtgaact tcaccaacag gaactatgac ctcgactacg actccgtaca gccctatttc    16200
atctgcgacg aggaagagaa tttctatcac cagcaacagc agagcgagct gcagccgccc    16260
gcgcccagtg aggatatctg gaagaaattc gagctgcttc ccaccccgcc cctgtccccg    16320
agccgccgct ccgggctctg ctctccatcc tatgttgcgg tcgctacgtc cttctcccca    16380
agggaagacg atgacggcgg cggtggcaac ttctccaccg ccgatcagct ggagatgatg    16440
accgagttac ttgaaggaga catggtgaac cagagcttca tctgcgatcc tgacgacgag    16500
accttcatca agaacatcat catccaggac tgtatgtgga gcggtttctc agccgctgcc    16560
aagctggtct cggagaagct ggcctcctac caggctgcgc gcaaagacag caccagcctg    16620
agccccgccc gcgggcacag cgtctgctcc acctccagcc tgtacctgca ggacctcacc    16680
gccgccgcgt ccgagtgcat tgacccctca gtggtctttc cctacccgct caacgacagc    16740
agctcgccca aatcctgtac ctcgtccgat tccacggcct tctctccttc ctcggactcg    16800
ctgctgtcct ccgagtcctc cccacggggcc agccctgagc cctagtgct gcatgaggag    16860 acaccgccca ccaccagcag cgactctgaa gaagagcaag aagatgagga agaaattgat    16920
gtggtgtctg tggagaagag gcaaaccct gccaagaggt cggagtcggg ctcatctcca    16980
tcccgaggcc acagcaaacc tccgcacagc ccactggtcc tcaagaggtg ccacgtctcc    17040
actcaccagc acaactacgc cgcacccccc tccacaagga aggactatcc agctgccaag    17100
agggccaagt tggacagtgg cagggtcctg aagcagatca gcaacaaccg caagtgctcc    17160
agccccaggt cctcagacac ggaggaaaac gacaagaggc ggacacacaa cgtcttggaa    17220
cgtcagagga ggaacgagct gaagcgcagc ttttttgccc tgcgtgacca gatccctgaa    17280
ttggaaaaca cgaaaaggc ccccaaggta gtgatcctca aaaaagccac cgcctacatc    17340
ctgtccattc aagcagacga gcacaagctc acctctgaaa aggacttatt gaggaaacga    17400
cgagaacagt tgaaacacaa actcgaacag cttcgaaact ctggtgcata agaattctgc    17460
agtcgacggt accgcgggcc cgggatccgc ccctctccct cccccccccc taacgttact    17520
ggccgaagcc gcttggaata aggccggtgt gcgtttgtct atatgttatt ttccaccata    17580
ttgccgtctt ttggcaatgt gagggcccgg aaacctggcc ctgtcttctt gacgagcatt    17640
cctaggggtc tttcccctct cgccaaagga atgcaaggtc tgttgaatgt cgtgaaggaa    17700
gcagttcctc tggaagcttc ttgaagacaa acaacgtctg tagcgaccct ttgcaggcag    17760
cggaaccccc cacctggcga caggtgcctc tgcggccaaa agccacgtgt ataagataca    17820
cctgcaaagg cggcacaacc ccagtgccac gttgtgagtt ggatagttgt ggaaagagtc    17880
aaatggctct cctcaagcgt attcaacaag gggctgaagg atgcccagaa ggtaccccat    17940
tgtatgggat ctgatctggg gcctcggtgc acatgcttta catgtgttta gtcgaggtta    18000
```
aaaaaacgtc taggcccccc gaaccacggg gacgtggttt tcctttgaaa aacacgatga    18060
taatatggcc aca                                                      18073

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctctagagtc gacccgttat tttccaccat attgcc                             36

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcacacatcc gccataaagg aaaaccacgt cccc                               34

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atggcggatg tgtgacata                                                19

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaataacatt taaatcgtag aggtgtataa cagg                               34

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atttaaatgt tattttccac catattgccg tcttttggc                          39

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
ttcaggcttt ttcataaagg aaaaccacgt cccc                                34

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgaaaaagc ctgaactcac                                                20

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tttttgcggc cgccccttgt acagctcgtc catg                                34
```

T7 ALPHA VIRAL VECTOR SYSTEM

CROSS REFERENCE TO RELATED APPLICATIONS

This application is the U.S. National Stage of PCT/US2016/062703, filed Nov. 18, 2016, which claims the benefit of U.S. Provisional Appl. No. 62/256,788, filed Nov. 18, 2015, the entire disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 15, 2018, is named sequence.txt and is 56 KB in size.

BACKGROUND

Alphaviruses are single-stranded RNA viruses with an envelope structure belonging to the family of Togaviridae. Alphavirus-based vectors are attractive candidates for vaccine development because they express high levels of recombinant proteins in mammalian cells, can elicit neutralizing antibodies and protection against challenges with tumor cells or lethal doses of viruses in animal models. Lundstrom et al. *Gene Ther. Mol. Biol.* 3:15-23 (1999). Alphavirus vectors are usually based on RNA replicons in which the viral structural genes have been deleted and substituted by a heterologous gene. The alphavirus replicon contains an ORF coding for a viral replicase at its 5' end, which is translated upon transfection of the RNA into eukaryotic cells. See Casales et al., *Virology* 376: 242-251 (2008). These vectors have been developed from different viruses, which include Sindbis virus (SIN), Semliki Forest virus (SFV), and Venezuelan equine encephalitis virus (VEE). See Xiong et al., *Science* 243: 1188-1191 (1989), Liljestrom et al., *Biotechnology* 9:1356-1361 (1991), Pushko et al., *Virology* 239:389-401(1997), and Casales et al., *Virology* 376: 242-251 (2008). A major problem associated with alphavirus-based vectors, however, is that an unmodified alphavirus vector is cytopathic in most mammalian cells due to mechanisms not yet fully understood. But a number of mutations in the alphavirus replicase that are capable of rendering theses vectors noncytopathic have been discovered, and most of these mutations have been detected in the nsp2 subunit of the RNA replicase. See Frolove et al., *J. Virol.* 73:3854-3865 (1999); Perri et al., *J. Virol.* 74:9802-9807 (2000), Lundstrom et al., *Expert Rev. Vaccines* 2:447-459 (2003), and Petrakova et al., *J. Virol.* 79:7597-7608 (2005).

Several types of alphavirus vector systems have been engineered, including naked RNA, recombinant virus particles, and layered DNA vectors. Naked RNA has the problem of low stability, leading to the variability of gene products due to degradation. Recombinant virus particles have the risk of generating replication-proficient viral particles through non-homologous recombination. The layered DNA/RNA vector consists of delivery of a DNA vector providing foreign gene expression from a CMV promoter, but transfection efficiencies can be reduced because the DNA must go into the nucleus for expression due to the type of promoter used, and DNA can insert into the host chromosome. Therefore, a need for efficient gene expression system based on alphavirus vectors still exists. The present invention satisfies this need.

SUMMARY OF THE INVENTION

In one aspect, the present invention provides a gene expression system in eukaryotic cells for gene expression in the cytoplasm. In some embodiments, the gene expression system comprises a vector which has the following components: a bacteriophage promoter, an alphavirus replicon operatively linked to the bacteriophage promoter, a first capping sequence, a subgenomic promoter, a second capping sequence, and a gene of interest. The gene expression system also comprises an exogenous RNA polymerase co-delivered with the vector into a cell, which transcribes the alphavirus replicon by recognizing the bacteriophage promoter.

In some embodiments, the alphavirus replicon is derived from an alpha virus selected from the group consisting of Sindbis virus (SIN), Semliki Forest virus (SFV), and Venezuelan equine encephalitis virus (VEE). In a preferred embodiment, the alphavirus replicon is noncytopathic, wherein the alphavirus replicon contains one or more mutations in the nsp2 subunit.

In some embodiments, the bacteriophage promoter is selected from the group consisting of T7, T3, and SP6 promoter. In some other embodiments, both the first and second capping sequences are the internal ribosome entry site sequence derived from encephalomyocarditis virus. In some embodiments, the gene of interest encodes for an antigen, which can be a viral antigen, a bacterial antigen, or a cancer antigen. In some embodiments, the subgenomic promoter is derived from an alphavirus. In a preferred embodiment, the bacteriophage promoter is T7 promoter, and the exogenous RNA polymerase is T7 polymerase.

In another aspect, the present invention provides a vector comprising a bacteriophage promoter, an alphavirus replicon operatively linked to the bacteriophage promoter, a first capping sequence, a subgenomic promoter, a second capping sequence, and a gene of interest. In some embodiments, the bacteriophage promoter is T7 promoter. In some embodiments, both the first and second capping sequences are the internal ribosome entry site sequence derived from encephalomyocarditis virus. In some embodiments, the gene of interest encodes for an antigen, which can be a viral antigen, a bacterial antigen, or a cancer antigen.

In yet another aspect, the present invention provides a method for producing an induced pluripotent stem cell, comprising (a) introducing into a mammalian somatic cell a gene expression system comprising a vector, wherein the vector comprises a sequence encodes one or more mammal-derived reprogramming factor, and an exogenous RNA polymerase co-delivered with the vector, and (b) culturing the transduced somatic cell in the presence of a cytokine on a fibroblast feeder layer or extracellular matrix under conditions for maintaining pluripotency and self-renewal. In some embodiments, the reprogramming factor is selected from the group consisting of Oct 3/4, Sox2, Klf4, and c-Myc. In a preferred embodiment, the combination of reprogramming factor Oct 4, Sox2, Klf4, and c-Myc are expressed. In some other embodiments, the method is carried out in the presence of a substance for improving the efficiency of establishment of the pluripotent stem cell. In some embodiments, the substance for improving an efficiency of establishment is a histone deacetylase (HDAC)

inhibitor, a histone methyltransferase (G9a) inhibitor, or a DNA methylase (Dnmt) inhibitor.

In another aspect, the present invention provides a vaccine comprising the gene expression system, wherein the gene of interest encodes an antigen, which can be a viral antigen, a bacterial antigen, and a cancer antigen. In a preferred embodiment, the vaccine comprises influenza hemagglutin, and is capable of eliciting an immune response against influenza virus.

In another aspect, the present invention provides a method for eliciting an immune response to an antigen in a subject, wherein the method comprises delivering into the subject the gene expression system, wherein the gene of interest encodes for an antigen; and inducing in the subject an immune response to the antigen in the subject. The present invention contemplates both prophylactic and therapeutic uses of the compositions and methods disclosed herein.

In another aspect, the present invention provides a therapeutic composition, comprising a dendritic cell transfected with the gene expression system, wherein the gene of interest encodes for an antigen capable of being displayed on the surface of the dendritic cell, wherein the therapeutic composition is capable of activating T cells to produce an immune response. In some embodiments, the antigen is a tumor antigen. In a preferred embodiment, the tumor antigen is a melanoma antigen selected from the group consisting of tyrosinase, tyrosinase related protein 1 (TRP-1), and tyrosinase related protein 2 (TRP-2).

In yet another aspect, the present invention provides a method for treating cancer, comprising administering to a patient in need thereof the therapeutic composition. In a preferred embodiment, cancer being treated is melanoma.

BRIEF DESCRIPTION OF THE DRAWINGS

FIG. 1 illustrates the alphavirus vector of the present invention. The alphavirus replicase gene is cloned under the T7 promoter. The gene of interest is inserted after the replicase region, and under the control of a subgenomic promoter of SFV. Two copies of the IREs sequence are present in the vector, one is inserted between the T7 promoter and the replicase, and the other is inserted between the SFV subgenomic promoter and the gene of interest. The poly A and T7 terminator sequence are placed after the gene of interest. An additional selection marker such as GFP and hygromycin can be inserted between the gene of interest and the T7 terminator sequence.

DETAILED DESCRIPTION

Definition

The following terms are used throughout the application. Unless otherwise indicated, the terms are defined as follows.

A "polynucleotide" is a nucleic acid polymer. A "polynucleotide" can include both double- and single-stranded sequences, and can include naturally derived and synthetic DNA sequences. The term also includes sequences that include any of the known base analogs of DNA and RNA, and includes modifications, such as deletions, additions and substitutions (generally conservative in nature) to native sequences.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to native sequence.

The term "antigen" refers to a molecule that contains one or more epitopes capable of stimulating an immunological response. Normally, an epitope will include between about 3-15, generally about 5-15, amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. *Proc. Natl. Acad. Sci. USA* 81:3998-4002(1984); Geysen et al. *Molec. Immunol.* 23:709-715 (1986), all incorporated herein by reference in their entireties. Similarly, conformational epitopes are readily identified by determining spatial conformation of amino acids such as by x-ray crystallography and 2-dimensional nuclear magnetic resonance. See, e.g., Epitope Mapping Protocols, supra.

For purposes of the present invention, antigens can be derived from any of several known viruses, bacteria, parasites and fungi, as well as any of the various tumors. Furthermore, for purposes of the present invention, an "antigen" refers to a protein, which includes modifications, such as deletions, additions and substitutions (generally conservative in nature), to the native sequence, so long as the ability to elicit an immunological response is maintained. These modifications may be deliberate, as through site-directed mutagenesis, or may be accidental, such as through mutations of hosts that produce the antigens.

An "immunological response" or "immune response" is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. Thus, an immunological response as used herein may be one which stimulates the production of cytotoxic T cells, and/or the production or activation of helper T-cells. Such responses can be determined using standard immunoassays and neutralization assays, well known in the art.

As used herein, the term "alphavirus" means a genus of viruses, all of which are members of the Togaviridae family. Known alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African arbovirus 86 (S.A.AR86) Semliki Forest virus, Middleburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus.

As used herein, the term "alphavirus RNA replicon" or "alphavirus replicon" is used to refer to an alphavirus RNA molecule expressing nonstructural protein genes such that it can direct its own replication (amplification) and comprises the 5' and 3' alphavirus replication recognition sequences, coding sequences for alphavirus nonstructural proteins, and a polyadenosine tract. It may additionally contain a regulatory cassette and a heterologous nucleic acid of interest that is expressed from the regulatory cassette. It may also be engineered to express one but not all alphavirus structural proteins.

"Vector" as used herein relates to genetically manipulated, cyclic, usually double-stranded nucleic acid molecules which allow specific selection and the directed introduction of genetic material of interest. Such vectors are mammalian expression vectors, bacterial plasmids, bacteriophage vectors, yeast episomal vectors, artificial chromosomal vectors or viral vectors.

The term "3' end" or "3' hydroxyl end" as interchangeably used herein relates to the termination at the hydroxyl group of the third carbon in the sugar-ring of a nucleic acid molecule, and is also known as the tail end. The term "5' end" or "5' phosphate end" as interchangeably used herein designates the end of the DNA or RNA strand that has a phosphate group at the fifth carbon in the sugar-ring of the deoxyribose or ribose at its terminus.

The term "host cell" or "host" as interchangeably used herein means an organism that harbors the isolated nucleic acid molecule or vector according to the present invention. Such host cell can be a mammalian cell, a plant, a bacterium, an insect cell or a nematode. Preferably, the host is a eukaryotic cell and, more preferably, said host is a mammalian cell.

As used herein, the term "promoter" refers to a polynucleotide molecule that is involved in recognition and binding of RNA polymerase and other proteins (trans-acting transcription factors) to initiate transcription.

The term "operatively linked" means that a regulatory sequence such as a promoter controls the expression of a gene.

The term "bacteriophage promoter" means a polynucleotide molecule derived from a bacteriophage, and is involved in recognition and binding of RNA polymerase and other proteins (trans-acting transcription factors) to initiate transcription. In preferred embodiments, the bacteriophage promoters are SP6, T7 and T3 promoters.

As used herein, the term "subgenomic promoter" refers to those sequences within an RNA molecule and at the 5' end of a structural gene, which direct messenger RNA synthesis using said RNA molecule as the template. A subgenomic promoter is necessary to drive expression of genes using RNA as template; the subgenomic promoter is recognized by an RNA-dependent RNA polymerase, which may be a viral RNA replicase. The promoter itself may be a composite of segments derived from more than one source, naturally occurring or synthetic. A preferred embodiment is the subgenomic promoter from Semliki Forest Virus.

The term "capping sequence" refers to a sequence capable for forming a cap structure found on the 5'-end of an mRNA molecule and generally consists of a guanosine nucleotide connected to the mRNA via an unusual 5' to 5' triphosphate linkage. In a preferred embodiment, the capping sequence is IRES sequence.

As used herein, the term "IRES" means an internal ribosome entry site. IRES sequences have been found in numerous transcripts from viruses that infect vertebrate and invertebrate cells as well as in transcripts from vertebrate and invertebrate genes. Examples of IRES elements suitable for use in this invention include: viral IRES elements from Picornaviruses e.g., polio virus (PV), encephalomyocarditis virus (EMCV), foot-and-mouth disease virus (FMDV), from Flaviviruses e.g. hepatitis C virus (HCV), from Pestiviruses e.g., classical swine fever virus (CSFV), from Retroviruses e.g., murine leukemia virus (MLV), from Lentiviruses e.g., simian immunodeficiency virus (SIV), or cellular mRNA IRES elements such as those from translation initiation factors e.g., eIF4G or DAP5, from Transcription factors e.g., c-Myc (Yang and Sarnow, *Nucleic Acids Research* 25:2800-2807 (1997)) or NF-κB-repressing factor (NRF), from growth factors e.g., vascular endothelial growth factor (VEGF), fibroblast growth factor (FGF-2), platelet-derived growth factor B (PDGF B), from homeotic genes e.g., Antennapedia, from survival proteins e.g. X-Linked inhibitor of apoptosis (XIAP) or Apaf-1, or chaperones e.g. the immunoglobulin heavy-chain binding protein BiP (Martinez-Salas et al., *Journal of General Virology* 82:973-984 (2001)). In a preferred embodiment, the IRES sequence is derived from encephalomyocarditis virus (EMCV, ATCC accession # NC001479).

The term "exogenous" in the context of the present invention means that the gene or enzyme is not normally present in the host organism in nature. The term "exogenous RNA polymerase" in the context of the present invention means that the RNA polymerase is not normally present in the host organism in nature. The skilled artisan will appreciate that the exogenous RNA polymerase may be delivered to the cells using methods well known in the art. In a preferred embodiment, the exogenous RNA polymerase is prebound to a vector, or co-deliver with a vector into the cell.

The term "dendritic cells" is used herein to refer to antigen presenting cells characterized by their peculiar dendritic morphology and multiple thin-membrane projections, and by their high density of class II MHC molecules. Dendritic cells include Langerhans cells of the skin, "veiled cells" of afferent lymphatics, follicular dendritic cells, dendritic cells of the spleen, and interdigitating cells of lymphoid organs. Dendritic cells can be obtained from the skin, spleen, bone marrow, lymph nodes, other lymphoid organs, and peripheral blood cord blood. Preferably, dendritic cells are obtained from blood or bone marrow for use in the invention.

Alphavirus Vector

In one aspect, the present invention provides an alphavirus vector for expressing a gene of interest in an animal or human cell. In the alphavirus vector, the alphavirus replicon is placed under the control of a promoter sequence, which initiates transcription of the alphavirus replicon, the alphavirus replicon then recognizes a subgenomic promoter and initiate transcription of the gene of interest, which is operatively linked to the subgenomic promoter. The present invention takes the advantage of the alphavirus replicon's high level transient heterologous gene expression, which makes it attractive for vaccine development.

In some embodiments, the alphavirus vector of the present invention includes the following components in the following 5' to 3' orientation: a bacteriophage promoter, a first capping sequence, a sequence encoding the alphavirus replicon, a subgenomic promoter, a second capping sequence, a gene of interest, a transcription terminator and polyA sequence. These components are operatively linked so that transcription initiates from the 5' end, proceed through the sequence encoding the alphavirus replicon, the gene of interest, and terminate at the 3' end. In addition, the alphavirus vector used herein may further contain the sequence of a multicloning site having a plurality of restriction enzyme recognition sites to facilitate insertion of a gene of interest, the sequence of IRES (internal ribosomal entry site), and the like.

Sequences encoding wild-type alphaviruses suitable for use in preparing the above-described vector can be readily obtained given the disclosure provided herein from naturally-occurring sources, or from depositories (e.g., the American Type Culture Collection, Rockville, Md.).

Representative examples of suitable alphaviruses include Aura virus (ATCC VR-368), Bebaru virus (ATCC VR-600, ATCC VR-1240), Cabassou virus (ATCC VR-922), Chikungunya virus (ATCC VR-64, ATCC VR-1241), Eastern equine encephalomyelitis virus (ATCC VR-65, ATCC VR-1242), Fort Morgan virus (ATCC VR-924), Getah virus (ATCC VR-369, ATCC VR-1243), Kyzylagach virus (ATCC VR-927), Mayaro virus (ATCC VR-66, ATCC VR-1277), Middleburg virus (ATCC VR-370), Mucambo virus (ATCC VR-580, ATCC VR-1244), Ndumu virus (ATCC VR-371), Pixuna virus (ATCC VR-372, ATCC VR-1245), Ross River virus (ATCC VR-373, ATCC VR-1246), Semliki Forest virus (ATCC VR-67, ATCC VR-1247), Sindbis virus (ATCC VR-68, ATCC VR-1248; see also CMCC #4640, described below), Tonate virus (ATCC VR-925), Triniti virus (ATCC VR-469), Una virus (ATCC VR-374), Venezuelan equine encephalomyelitis virus (ATCC VR-69, ATCC VR-923, ATCC VR-1250 ATCC VR-1249, ATCC VR-532), Western equine encephalomyelitis virus (ATCC VR-70, ATCC VR-1251, ATCC VR-622, ATCC VR-1252), Whataroa virus (ATCC VR-926), and Y-62-33 virus (ATCC VR-375).

Alphavirus cytopathic vectors are useful in various applications, such as in vitro protein production and characterization, vaccination, and cancer gene therapy studies. However, cytopathic vectors cannot be used where long term gene expression is required, such as IPS induction. In some embodiments, the alphavirus replicon in the present invention may contain one or more mutations that make the alphavirus replicon noncytopathic. A mutation can be a nucleotide deletion, addition, or substitution of one or more nucleotide(s), or a mutation that comprises rearrangement or chimeric construction which results in a loss of cytopathic effect of a live virus containing the mutation as compared to the appropriate wild-type alphavirus. Such mutations can be present in the alphavirus non-structural proteins, nsp1-nsp4 subunit. In some preferred embodiments, the mutation is present in the alphavirus nsp-2. Exemplary mutations in nsp-2 include, but are not limited to, a deletion or a substitution of an amino acid at any one or more of the following: nsp2 amino acid position 1, nsp2 amino acid position 10, nsp2 amino acid position 469, nsp2 amino acid position 472; nsp2 amino acid position 694; nsp2 amino acid position 713; nsp2 amino acid position 718; nsp2 amino acid position 721. In some embodiments, the non-cytopathic alphavirus replicon has mutation P718T in nsp2. In some embodiments, the non-cytopathic alphavirus replicon has mutation R649H in nsp2. In some embodiments, the non-cytopathic alphavirus replicon has both mutations P718T and R649H in nsp2. Sequences encoding non-cytopathic alphavirus replicon and method for making the non-cytopathic alphavirus replicon are known in the art, for example, described in Belli et al. US2003/0170871; Frolova et al., *J. Virol.*, 76:11254-11264 (2002); Perri et al., *J. Virol.*, 74:9802-9807 (2000); Lundstrom et al., *Expert Rev. Vaccines* 2:447-459 (2003); Lundstrom et al., *Cell Biol.*, 115:83-91 (2001); Petrakova et al., *J. Virol.*, 79:7597-7608 (2005); Casales et al., *Virology*, 376(1):242-251 (2008). All of these references are incorporated herein by reference in their entirety.

In some embodiments, the bacteriophage promoter of the alphavirus vector is selected from the group consisting of T7, T3, or SP6 promoter. In a preferred embodiment, the bacteriophage promoter is T7 promoter. In another preferred embodiment, the transcription terminator is T7 terminator. The sequences of the T7 promoter and terminator are known in the art. See Reim et al. U.S. Pat. No. 5,122,457.

In some embodiments, the first and second capping sequences are the sequence of an internal ribosome entry site (IBES). Examples of IRES suitable for use in this invention include: viral IRES elements from Picornaviruses e.g., poliovirus (PV), encephalomyocarditis virus (EMCV), foot-and-mouth disease virus (FMDV), from Flaviviruses e.g. hepatitis C virus (HCV), from Pestiviruses e.g., classical swine fever virus (CSFV), from Retroviruses e.g., murine leukemia virus (MLV), from Lentiviruses e.g., simian immunodeficiency virus (SIV), or cellular mRNA IRES elements such as those from translation initiation factors e.g., eIF4G or DAP5, from Transcription factors e.g., c-Myc (Yang and Sarnow, *Nucleic Acids Research* 25:2800-2807 (1997)) or NF-κB-repressing factor (NRF), from growth factors e.g., vascular endothelial growth factor (VEGF), fibroblast growth factor (FGF-2), platelet-derived growth factor B (PDGF B), from homeotic genes e.g., *Antennapedia*, from survival proteins e.g. X-Linked inhibitor of apoptosis (XIAP) or Apaf-1, or chaperones e.g. the immunoglobulin heavy-chain binding protein BiP (reviewed in Martinez-Salas et al., *Journal of General Virology* 82:973-984 (2001)). In a preferred embodiment, the first and second capping sequences are the sequence of IRES from encephalomyocarditis virus (EMCV, ATCC accession # NC001479).

General procedures for the constructing the above alphavirus vector are described in Sambrook, J. et al., Molecular Cloning: A Laboratory Manual, 2nd edition, Cold Spring Harbor Laboratory Press (1989); Ausubel, F. M. et al., Short protocols in Molecular Biology: A Compendium Methods from Current Protocols in Molecular Biology, John Wiley & Sons (1999); and the like.

Co-Delivery of Exogenous RNA Polymerase

In another aspect, the present invention provides a gene expression system comprising an alphavirus vector and an exogenous RNA polymerase, which is pre-bound to the alphavirus vector, and co-delivered into a cell. A unique feature of the gene expression system is that the initiation of gene expression depends upon the binding of the exogenous RNA polymerase to the vector prior to entering into host cells. The complex of pre-bound RNA polymerase to the vector is stable without detachment during entry into cells. Once the RNA polymerase and bound vector enters the cytoplasm of the cells, transcription is initiated immediately by the pre-bound RNA polymerase, via the bacteriophage promotor in the vector. The gene expression system is designed in such a manner that the expression of the gene of interest occurs only in the cytoplasm and does not require integration into the genome of the host cells in the nucleus since the bacteriophage T7 RNA polymerases do not contain nuclear localization signals and stay in the cytoplasm. See Dunn et al. Gene 68, 259-266 (1988). In a preferred embodiment, the exogenous RNA polymerase is T7 RNA polymerase, the sequence of which is known in the art. See Reim et al. U.S. Pat. No. 5,122,457.

The gene expression system of the present invention provides several advantages compared to other alphavirus based expression methods. First, gene expression is rapid because it does not require the DNA to enter into the cell nucleus for the initiation of transcription. The cytoplasmic location of its site of action also provides for a safety feature which reduces the possibility of its integration into the host cell genome at a site adjacent to and thereby activating a dormant gene such as an oncogene. Furthermore, unlike retroviral vectors, even if DNA integration occurred, the exogenous promoter used would not be activated by eukaryotic transcription proteins. The RNA polymerase is synthesized in the cell cytoplasm, and would not be able to gain access to the nucleus for binding to its cognate promoter because it lacks any nuclear translocation signal. This gene expression system encompasses a variety of applications. For example, it is useful for rapid production of high amounts of proteins for use in immunization of animals for the generation of specific antibodies. In this regard, the present invention may be used to introduce exogenous genes into cells and tissues in vivo for transient expression of the gene product to elicit an antigen-specific host immune response. The short-term nature of gene expression may be ideal for its use as a vehicle for in vivo immunization of a host to an antigen.

Stem Cell Therapy

In one aspect, the present invention provides a method for preparing an induced pluripotent stem cell by reprogramming a mammalian somatic cell. Because the gene expression system of the present invention takes the advantage of the high transfection efficiency of the alphavirus replicon, it provides efficient transfection of somatic cells to prepare induced pluripotent stem cells. The term "induced pluripotent stem cells" or "iPS cells" as used herein refers to artificially produced cells having pluripotency, which are not so-called embryonic stem (ES) cells, but have properties analogous to those of ES cells. The iPS cells have been established from mouse somatic cells, and human somatic cells. See Takahashi and Yamanaka et. al., *Cell* 126: 663-676 (2006); Takahashi et. al., *Cell* 13 1: 861-872 (2007); Yu et al., *Science* 318: 1917-1920 (2007); Nakagawa et al., *Nat. Biotechnol.* 26: 101-106 (2008). The iPS cells have the following characteristics: they are capable of differentiating into various cells that compose an animal body (that is, a pluripotency); they are capable of maintaining semipermanent proliferation while also retaining the karyotype; and a group of genes that are generally expressed by ES cells is similarly expressed, for example. Hence, the iPS cells are cells artificially induced by reprogramming of somatic cells, having properties clearly differing from those of differentiated somatic cells.

In some embodiments, the gene expression system can be used to express one or more iPS cell reprogramming factors. In some embodiments, the gene expression system comprises a vector comprising a non-cytopathic alphavirus replicon which has one or more mutations in nsp2. Exemplary mutations in nsp-2 include, but are not limited to, a deletion or a substitution of an amino acid at any one or more of the following: nsp2 amino acid position 1, nsp2 amino acid position 10, nsp2 amino acid position 469, nsp2 amino acid position 472; nsp2 amino acid position 694; nsp2 amino acid position 713; nsp2 amino acid position 718; nsp2 amino acid position 721. In some embodiments, the non-cytopathic alphavirus replicon has mutation P718T in nsp2. In some embodiments, the non-cytopathic alphavirus replicon has mutation R649H in nsp2. In some embodiments, the non-cytopathic alphavirus replicon has both mutations P718T and R649H in nsp2. In some embodiments, the mutations in nsp2 are P718T and R649 H.

The term "reprogramming" as used herein refers to a process or means during which differentiated cells are induced and converted into undifferentiated cells, particularly pluripotent cells. According to the present invention, the reprogramming of somatic cells into iPS cells can occur independently of germ-line cells such as ova (or eggs), oocytes, and ES cells. Reprogramming factors as used herein include proteins, nucleic acids, or combinations thereof. Examples of reprogramming factors reported to date include: Oct3/4, Sox2, and Klf4; Oct3/4, Klf4, and c-Myc; Oct3/4, Sox2, Klf4, and c-Myc; Oct3/4 and Sox2; Oct3/4, Sox2, and Nanog; Oct3/4, Sox2, and Lin28; and Oct3/4 and Klf4. The sequences of the above mentioned reprogramming factors are also available via access to the GenBank (NCBI, U.S.A.). See US 2011/0250692.

Amino acid and nucleotide sequences of the above reprogramming factors Oct3/4, Nanog, and Lin28, respectively, are available via access to the GenBank (NCBI, U.S.A.). Regarding Oct3/4, for example, the sequences of human Oct3/4, mouse Oct3/4, and rat Oct3/4 are registered as NM_203289 or NM_002701, NM 013633, and NM OO 1009178, respectively. Regarding Nanog, for example, the sequences of human Nanog, mouse Nanog, and rat Nanog are registered as NM_024865, NM_028016, and NM OO 1100781, respectively. Regarding Lin28, for example, the sequences of human Lin28, mouse Lin28, and rat Lin28 are registered as NM_024674, NM 145833, and NM OOl 109269, respectively. As a factor analogous to Lin28, Lin28b belonging to the same Lin family is known. Hence, in addition to Lin28 or instead of Lin28, Lin28b can be used. Regarding Lin28b, for example, the sequences of human Lin28b and mouse Lin28b are registered as NM OO 1004317 and NM_001031772, respectively.

In a preferred embodiment, the reprogramming factors for inducing iPS cells from somatic cells according to the present invention are the combination of reprogramming factors Oct 3/4, Sox 2, Klf 4, and c-Myc. In another preferred embodiment, a combination of the above reprogramming factors can be expressed simultaneously.

Examples of reprogramming factors other than the above factors include, but are not limited to, one or more reprogramming factors (or a group of reprogramming factors) selected from among ECAT1, and ECAT2 (also referred to as ESG1), ECAT3 (also referred to as Fbx15), ECATS (also referred to as Eras), ECAT7, ECAT8, and ECAT9 (also referred to as Gdf3), ECAT lO (also referred to as Sox15), ECAT15-1 (also referred to as Dppa4), ECAT 15-2 (also referred to as Dppa2), Fthl 17, Sall4, and Rex1 (also referred to as Zfp42), Utfl, Tell, and Stella (also referred to as Dppa3), β-catenin (also referred to as Ctnnb1), Stat3, Grb2, c-Myc, Sox1, Sox3, N-Myc, L-Myc, Klf1, Klf2, Klf4, and Klf5 (International Publication WO2007/069666), and, FoxD3, ZNF206, Myb12, and Otx2 (International Publication WO2008/118820). The sequences of the above mentioned reprogramming factors are also available via access to the GenBank (NCBI, U.S.A.). See US 2011/0250692.

Types of mammals from which each reprogramming factor is derived, are not limited and any mammals can be used. Examples of preferred mammals include primates (e.g., humans, monkeys, and chimpanzees), rodents (e.g., mice, rats, guinea pigs, and hamsters), Ungulata (e.g., cattle, horses, sheep, goats, and pigs), and pet animals (e.g., dogs and cats). In general, when somatic cells from a specific mammal are reprogrammed, reprogramming factors from the same mammal are preferably used. For example, when iPS cells are induced from somatic cells from a human, reprogramming factors from a human are used.

In a preferred embodiment, the nucleotide sequences encoding one or more of the reprogramming factors can be cloned into the alphavirus vector, preferably between the subgenomic sequence and the T7 terminator sequence. The alphavirus vector may further comprise a selection marker. Examples of a selection marker include drug resistance genes (e.g., a hygromycin resistance gene, a neomycin resistance gene, and a puromycin resistance gene), reporter genes (e.g., GFP (green fluorescence protein), GUS (β-gluclonidase), and FLAG), and negative selection markers (e.g., a thymidine kinase (TK) gene and a diphtheria toxin (DT) gene).

In a preferred embodiment, a plurality of reprogramming factors are tandemly ligated so that expression is possible, thereby preparing a cassette containing them. This cassette is incorporated into a vector, preferably between the subgenomic promoter and the terminator sequence. A linker sequence may be placed between reprogramming factors. For ligation of two or more reprogramming factors (or genes), any sequences which enable polycistronic expression can be employed, such as foot and mouse disease virus-derived 2A sequence (PLoS 0NE3, e2532, 2008, Stem Cells 25, 1707, 2007), IRES sequence (U.S. Pat. No. 4,937, 190).

In some embodiments, additional agents may be added to further improve or accelerate the establishment of iPS cells. Such agents may include, but are not limited to, cytokines such as a basic fibroblast growth factor (bFGF) and a stem cell factor (SCF). Furthermore, the agents may also include low-molecular-weight compounds such as: histone deacetylase (FIDAC) inhibitors, e.g., valproic acid (VPA), histone methyltransferase (G9a) inhibitors, e.g., BIX-01294 (BIX), and DNA methylase (Dnmt) inhibitors, e.g., 5'-azacytidine. See Huangfu, et al., *Nat. Biotechnol.*, 26 (7): 795-797 (2008); Shi, et al., *Cell Stem Cell*, 2: 525-528 (2008); Kubicek, et al., *Mol. Cell* 25: 473-481 (2007); Shi, et al., *Cell Stem Cell*, 3: 568-574 (2008). Also, a p53 inhibitor such as shRNA or siRNA against p53 or UTF1 may be introduced into cells. See Yang et al., *Cell Stem Cell*, 3: 475-479 (2008). Furthermore, concerning signal transduction, activation of the Wnt signal, inhibition of mitogen-activated protein kinase and glycogen synthase kinase-3 signal transduction, ES cell specific miRNAs can also improve an efficiency for establishment of iPS cells. See Marson et al., *Cell Stem Cell*, 3: 32-135, (2008), Silva et al., *PLoS Biology*, 6, pp2237-2247 2008), and Judson et al., *Nat. Biotechnol.* 27:459-461 (2009)).

Examples of somatic cells used herein include, but are not limited to, any of fetal somatic cells, neonate somatic cells, and mature somatic cells, primary cultured cells, passaged cells, and established cell lines. Examples of somatic cells further include tissue stem cells and tissue precursor cells. Specific examples of somatic cells include, but are not limited to, (1) tissue stem cells (somatic stem cells) such as neural stem cells, hematopoietic stem cells, mesenchymal stem cells, and dental pulp stem cells, (2) tissue precursor cells, and (3) differentiated cells such as lymphocytes, epithelial cells, endothelial cells, muscle cells, fibroblasts (e.g., skin cells), hair follicle cells, hepatocytes, gastric mucosal cells, enterocytes, splenocytes, pancreatic cells (e.g., pancreatic exocrine cells), brain cells, pneumocytes, renal cells, and skin cells.

Mammalian individuals, which are suitable as origins to obtain somatic cells, are, but are not limited to, preferably patients themselves or other persons who have an identical or substantially identical HLA type from the viewpoints that when iPS cells obtained are used for regenerative medicine, no rejection occurs. As used herein, the term "substantially identical" with respect to HLA types means that when cells produced by inducing differentiation of iPS cells derived from somatic cells are transplanted to a patient, the HLA type matches between donor and recipient to the extent that the transplanted cells are survivable, such as the case where major HLAs (e.g., three gene loci of HLA-A, HLA-B and HLA-DR) are identical. This is applied similarly below. When iPS cells are not administered or transplanted, for example when iPS cells are used as a cell source for screening to evaluate the presence or absence of a drug sensitivity or adverse effect in patients, it is desirable to obtain somatic cells from patients themselves or other persons who have an identical gene polymorphism correlating with drug sensitivity or adverse effect.

Somatic cells can be cultured on a basal medium, such as DMEM (Dulbecco's modified Eagle medium), MEM (minimum essential medium), α-MEM (minimum essential medium alpha modification), Ham's F 12, RPMI 1640, or a mixture thereof, supplemented with appropriately selected substances such as serum (e.g., 10% FBS), an antibiotic(s) (e.g., penicillin and/or streptomycin), Na pyruvate, glutamine, nonessential amino acids, and L-dextrose at a temperature of about 37° C. in the presence of 5% $CO_2$. The culture procedures are known to persons skilled in the art, for example, see US 2011/0250692.

Methods for introducing reprogramming factors encoding nucleic acids into cultured somatic cells from a mammal include conventional methods, such as an electroporation method, a microinjection method, a calcium phosphate method, a viral infection method, a lipofection method, and a liposome method.

For induction of iPS cells, cultured somatic cells are brought into contact with the above reprogramming factors in an appropriate medium for animal cell culture, to introduce the reprogramming factors into somatic cells, whereby the cells are transformed or transduced. Examples of culture medium include, but are not limited to, a DMEM, DMEM/F12 or DME medium containing 10-15% FBS, which medium may further optionally contain LIF (leukemia inhibiting factor), penicillin/streptomycin, puromycin, L-glutamine, nonessential amino acids, β-mercaptoethanol, and the like), a medium for ES cell culture containing bFGF or SCF, such as medium for mouse ES cell culture (e.g., TX-WES™, COSMO BIO) or medium for primate ES cell culture (e.g., ReproCELL™, COSMO BIO). The culture procedures are known to persons skilled in the art, for example, see US 2011/0250692.

Pluripotency (or the formation of three germ layers) can be confirmed based on teratoma formation and identification of each tissue (or cells) of three germ layers (endoderm, mesoderm, and ectoderm) within teratoma tissues, for example. Specifically, in the case of mouse iPS cells, cells are injected subcutaneously into a nude mouse, or in the case of human iPS cells, cells are injected into the testis of a Scid mouse, and then tumorigenesis is confirmed. Pluripotency can be confirmed by the result that tumor tissues are composed of, for example, a cartilage tissue (or cells), a neural tube tissue (or cells), a muscle tissue (or cells), an adipose tissue (or cells), an intestine-like tissue (or cells), or the like. Furthermore, pluripotency can also be confirmed by histological staining that the thus generated teratomas contained neural tube tissues (ectoderm), cartilage tissues (mesoderm), intestine-like tissues (endoderm).

The iPS cells can be induced to form various differentiated cells, precursor cells, and tissues. Specifically, various differentiated cells such as nerve cells and cardiac muscle cells can be induced from iPS cells in the presence of a factor(s) such as activin A/BMP4 (bone morphogenetic protein 4) or VEGF (vascular endothelial growth factor). The obtained differentiated cells can be used as regenerative medicine to treat a patient by transplanting the cells into a patient, such as patients with defective tissues.

Vaccines Against Viruses And Other Pathogens

In one aspect, the present invention provides a method for delivering vaccines. In some embodiments, the gene expression system of the present invention allows expression of a target gene, which may encode immunogenic proteins from various pathogens. In some embodiments, the pathogens are viruses. For example, the immunogenic proteins may be derived from bovine viral diarrhea virus (BVDV), cytomegalovirus (CMV), classical swine fever virus CSFV, Dengue, Ebola, Hepatitis B, Hepatitis C, Hendra virus (HeV), human immunodeficiency virus (HIV-1), human papillomavirus (HPV), herpes simplex virus (HSV-1), infectious bursal disease virus (IBDV), Influenza, infectious salmon anemia virus (ISAV), Japanese encephalitis virus (JEV), Lassa, Louping-ill virus (LIV), Marburg virus (MBGV), Measles, Murray Valley encephalitis virus (MVE), Nipah virus (NiV), Norwalk-like virus (NLV), Rabies, respiratory syncytial virus (RSV), Rift Valley fever virus (RVFV), severe acute respiratory syndrome corona virus (SARS-CoV), Seoul virus (SEOV), simian-human immunodeficiency virus (SHIV), Sudan virus (SUDV), Vaccinia. The representative immunogenic proteins or peptides are shown in Table 1.

TABLE 1

Viral Immunogenic Proteins

| Virus | Target |
| --- | --- |
| Bovine viral diarrhea virus (BVDV) | E2, NS3 (p80) |
| Cytomegalovirus (CMV) | gB/pp65-1E1 |
| Classical swine fever virus (CSFV) | E2 |
| Dengue | PrME, E85 |
| Ebola | NP, GP, VP24, VP30, VP35, VP30 |
| Hepatitis B | cAg, sAg |
| Hepatitis C | cAg, NS3, nsPs |
| Hendra virus (HeV) | Glycoprotein |
| Human immunodeficiency virus (HIV-1) | Env, gp41, MA/CA |
| Human papillomavirus (HPV) | 16E7, VP22 |
| Herpes simplex virus (HSV-1) | gpB |
| Infectious bursal disease virus (IBDV) | VP2 |
| Influenza | HA, NP |
| Infectious salmon anemia virus (ISAV) | HE |
| Japanese encephalitis virus (JEV) | prM-E, NS1-2A |
| Lassa | N |
| Louping-ill virus (LIV) | prME, NS1 |
| Marburg virus (MBGV) | GP, NP, VP35 |
| Measles | HA, FUd |
| Murray Valley encephalitis virus (MVE) | prME, E |
| Nipah virus (NiV) | Glycoproteins |
| Norwalk-like virus (NLV) | VLP |
| Rabies | G |
| Respiratory syncytial virus (RSV) | F, G |
| Rift Valley fever virus (RVFV) | Gn |
| Severe acute respiratory syndrome corona virus (SARS-CoV) | Glycoprotein |
| Seoul virus (SEOV) | M, S |
| Simian-human immunodeficiency virus (SHIV) | Env |
| Sudan virus (SUDV) | GP |
| Vaccinia | A33R, B5R |

In some embodiments, the immunogenic proteins or peptides may be derived from non-viral pathogens. For example, the immunogenic proteins may be derived from *B. anthracis, B. abortus, C. Botulinum, Malaria, M tuberculosis, P. falciparum*, Prion, *Staphylococcus*. The exemplary immunogenic proteins are shown in Table 2.

TABLE 2

Non-viral pathogenic immunogens

| Agent | Target |
| --- | --- |
| B. anthracis | PA |
| B. abortus | IF3 |
| C. botulinum | BoNTA-Hc |
| Malaria | CS |
| M. tuberculosis | Ag85A |
| P. falciparum | Ag Pf332 |
| Prion | NP |
| Staphylococcus | enterotoxin B |

Any suitable vaccine and method of vaccination (i.e., immunization) known in the art may be employed in carrying out the present invention, as long as an active immune response against the antigen is elicited.

In a preferred embodiment, the vaccine method is naked DNA vaccines. DNA vaccination involves administering a polynucleotide that encodes an antigen in vivo to induce the production of an antigen within the target cells. The introduction of the DNA vaccine will cause the antigen to be displayed on the cellular surface of the transfected cells in conjunction with the Major Histocompatibility Complex (HMC) of the normal cell. Furthermore, the antigens expressed by the transfected cells can also be picked up by antigen-presenting cells to trigger systemic humoral antibody responses.

In some embodiments, the gene expression system can be incorporated into a vaccine composition, which may further comprises an adjuvant. As used herein, "adjuvant" describes a substance, which can be any immunomodulating substance capable of being combined with the polypeptide or nucleic acid vaccine to enhance, improve or otherwise modulate an immune response in a subject without deleterious effect on the subject. For example, an adjuvant of this invention can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules). Suitable adjuvants also include oil-in-water, saponin, an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes. Vaccines may also be formulated with a pharmaceutically acceptable excipient. Such excipients are well known in the art, and typically should be physiologically tolerable and inert or enhancing with respect to the vaccine properties of the inventive compositions. Examples include liquid vehicles such as sterile, physiological saline. When using an excipient, it may be added at any point in formulating the vaccine or it may be admixed with the completed vaccine composition.

In some embodiments, the vaccine administered may be in an amount of about 1-5 ug of DNA per dose and will depend on the subject to be treated, capacity of the subject's immune system to develop the desired immune response, and the degree of protection desired. Precise amounts of the vaccine to be administered may depend on the judgment of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

Preferably, the DNA for vaccine preparation is frozen or lyophilized, to form a dry powder. If a solution is used in formulation, the dry ingredients for the solution may be premixed and premeasured and contained in a container such as a vial or sealed envelope.

Vaccines may be formulated for multiple routes of administration. Specifically preferred routes include intramuscular, percutaneous, subcutaneous, or intradermal injection, aerosol, oral or by a combination of these routes, at one time, or in a plurality of unit dosages. Administration of vaccines is well known and ultimately will depend upon the particular formulation and the judgment of the attending physician.

Cancer Vaccine

One aspect of the present invention provides a method for treating cancer by administering to a mammal suffering from cancer an alphavirus vector that comprises a gene encoding a cancer antigen or an anti-cancer gene. In some embodiments, the cancer being treated can be, but is not limited to, brain tumor, cervical cancer, colon cancer, endothelial cancer, malignancies (such as neuroblastoma, gliblastoma, glioma, medulloblastoma, astrocytoma, acoustic neuroma, oligodendroglioma, and meiningioma), kidney cancer, melanoma, metastatic cancer, prostate cancer, breast cancer, bladder cancer, pancreatic cancer, lung cancer (such as small cell lung and non-small cell lung cancer).

In some embodiments, the cancer antigen is a protein or peptide capable of eliciting an immune response against cancer. For example, such a protein or peptide includes but is not limited to melanosornal antigens (such as a melanocytic tissue-specific protein, gp100, MART-1, and tyrosinase), cancer markers (such as HER2-near, CEA and PSA). The sequence of these cancer antigens are known to persons skilled in the art, for example, they are described in Rosenberg et al., *Immunity*, 10: 281-287 (1999). Exemplary cancer antigens are shown in Table 3.

TABLE 3

Cancer Vaccine Gene Target

| Antigen Category | Gene |
| --- | --- |
| Melanocyte differentiation | MART-1/MelanA gp100, Tyrosinase, TRP-1, TRP-2 |
| Cancer testis | MAGE-1, MAGE-3, GAGE-1/2, BAGE, RAGE, NY-ESO-1 |
| Tumor specific | CDK-4, β-catenin, MUM-1, Caspase-8, KIAA0205, HPVE7, |
| Widely expressed | SART-1, PRAME, p15 |

In some embodiments, the anti-cancer gene can be a suicide gene, an apoptosis-inducing gene, a tumor suppressor gene, an oncogene antagonist gene, a tumore suppressor effector gene, an antisense oligonucleotide-encoding sequence, a ribozyme-encoding sequence. In a preferred embodiment, such anti-tumor gene is an apoptosis-inducing gene. The representative anti-cancer genes are shown in Table 4.

TABLE 4

Anti-cancer genes

| Target | Gene |
| --- | --- |
| Brain tumor | IL-12, Endostatin, gp100, IL-18, HER2/neu |
| Cervical cancer | HPVE6-E7, HPV-CRT (carcinoembryonic antigen), HPVE7, IL2, HPVE7-VP22, |
| Endothelial | VEGFR-2 |
| Glioma | B16, 203 |
| Kidney cancer | IL-12 |
| Melanoma | MDA/trp-2 (melanoma differentiation antigen), IL-12, MUC18/MCAM melanoma cell adhesion molecule) |
| Metastatic | carcinoembryonic antigen (CEA), prostate-specific membrane antigen (PSMA) |
| Prostate cancer | prostate-specific membrane antigen (PSMA), six-transmembrane epithelial antigen of the prostate (STEAP), prostate stem cell antigen (PSCA) |
| Tumor | β-galactosidase, IL-12, MHC class II, P815, trp-1 |

In some embodiments, the gene expression system of the present invention can be administered to a patient prior to or following the detection of cancer in a subject, via suitable method known to persons skilled in the art, and as described above. Additionally, when administered according to the present invention, the artificial cancer cell antigen should be able to induce an active and protective immune response against unmodified cancer cells.

Vaccines comprising the gene expression system may be formulated for multiple routes of administration. Specifically preferred routes include intramuscular, percutaneous, subcutaneous, or intradermal injection, aerosol, oral or by a combination of these routes, at one time, or in a plurality of unit dosages. Administration of vaccines is well known and ultimately will depend upon the particular formulation and the judgment of the attending physician. The vaccines may further comprise an adjuvant or excipient known to persons skilled in the art, and as described above.

Dendritic Cell Vaccine

In another aspect, the present invention provides a method for immune cell stimulation, such as a dendritic cell stimulation to generate a strong anti-tumor immune response. In some embodiments, the present invention provides a methods for transfecting antigens with dendritic cells so that the antigens are displayed at the surface of dendritic cells to elicit an immune response against the antigen of interest.

In some embodiments, the antigens for use in dendritic cell stimulation by the present invention are tumor antigens that include, but are not limited to melanoma tumor antigens (Kawakami et al., *Proc. Natl. Acad, Sci. USA* 91:3515-3519 (1994); Kawakami et al., *J. Exp. Med.*, 180:347-352 (1994); Kawakami et al. *Cancer Res.* 54:3124-3126 (1994), including MART-1 (Coulie et al., *J. Exp. Med.* 180:35-42 (1991), gp100 (Wick et al., *J. Cutan. Pathol.* 15:201-207 (1988) and MAGE antigen, MAGE-1, MAGE-2 and MAGE-3 (Van der Bruggen et al., *Science,* 254:1643-1647 (1991)); CEA, TRP-1, P-15 and tyrosinase (Brichard et al., *J. Exp. Med.* 178:489 (1993)); HER-2/neu gene product (U.S. Pat. No. 4,968,603); estrogen receptor, milk fat globulin, p53 tumor suppressor protein (Levine, Ann. Rev. Biochem. 62:623 (1993)); mucin antigens (Taylor-Papdimitriou, International Pub. WO90/05142)); telomerases; nuclear matrix proteins; prostatic acid phosphatase; papilloma virus antigens; and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (e.g., Rosenberg, *Ann. Rev. Med.* 47:481-91 (1996)).

In a preferred embodiment, the tumor antigen for use in the dendritic cell vaccine of the present invention is tyrosinase, tyrosinase related protein 1 (TRP-1), or tyrosinase related protein 2 (TRP-2). Tyrosinase, TRP-1 and TRP-2 are members of the tyrosinase related gene family.

One aspect of the invention relates to gene expression of cancer peptides encoded by the tyrosinase, TRP-1 gene, TRP-2 gene or variants thereof, in the dendritic cell. Tyrosinase gene, TRP-1 antigen, TRP-2 antigen, a fragment thereof, alone or in combination with one or more co-immunostimulatory molecules can be used. In one aspect, the present invention contemplates both preventing and treating melanoma by expressing tyrosinase gene, TRP-1 antigen, TRP-2 antigen in dendritic cells.

In some embodiments, the gene expression system expressing the tumor antigens stated above are inserted ex vivo into dendritic cells, such that one or more selected antigens are presented in effective amounts on the surface of the dendritic cells. By "effective amount" it is meant that presentation is sufficient to enable the dendritic cells to provoke an immune response. Techniques for nucleic acid manipulation are well known. Reagents useful in applying such techniques, such as restriction enzymes and the like, are widely known in the art and commercially available from a number of vendors.

The alphavirus vectors may also contain polynucleotide sequences encoding selected class I and class II MHC molecules, costimulation and other immunoregulatory molecules, ABC transporter proteins, including the TAP1 and TAP2 proteins. Thus, various combinations of polynucleotide sequences may be inserted the alphavirus vector of the present invention. The alphavirus vectors may further contain at least one positive marker that enables the selection of dendritic cells carrying the vector.

In a preferred embodiment, dendritic cells are obtained from a patient to be treated. The dendritic cells are used to activate T cells of the patient, either in vitro or in vivo, for immunotherapy.

In another embodiment, dendritic cells are obtained from a healthy individual. The relevant HLA antigens (both class I and II, e.g., HLA-A, B, C and DR), for example, on the individual's peripheral blood mononuclear cells (PBMC's), are identified and dendritic cells that match the patient, in terms of HLA antigens, are isolated and expanded as described above. For example, in certain instances, a late stage cancer patient who has been treated with radiation and/or chemotherapy agents is not able to provide sufficient or efficient dendritic cells. Thus, dendritic cells from healthy HLA-matched individuals, such as siblings, can be obtained and expanded using any of the methods described above.

The procedures for isolating dendritic cells are known to the person skilled in the art. For example, dendritic cells can be obtained from any tissue where they reside, including non-lymphoid tissues such as the epidermis of the skin (Langerhans cells) and lymphoid tissues such as the spleen, bone marrow, lymph nodes and thymus as well as the circulatory system including blood (blood dendritic cells), for example peripheral blood and cord blood, and lymph (veiled cells). For example, explants of mouse or human skin placed in organ culture permit selective migration of dendritic cells into the medium surrounding the explant. See Larsen et al., *J. Exp. Med.* 172:1483-1493 (1990), and Richters et al., *J. Invest. Dermatol.* (1994).

Recent studies have described methods for the isolation and expansion of human dendritic cells, including from human peripheral blood. See Macatonia et al., *Immunol.* 74: 399-406 (1991); O'Doherty et al., *J. Exp. Med.* 178: 1067-1078 (1993); and Markowicz et al., *J. Clin. Invest.* 85: 955-961(1990); Romani et al., *J. Exp. Med.* 180: 83-93 (1994); Sallusto et al., *J. Exp. Med.* 179: 1109-1118 (1994); Bernhard et al., *Cancer Research* 55: 1099-1104 (1995). Techniques for deriving dendritic cells (including Langerhans' cells) from CD34+ progenitor cells obtained from bone marrow and cord blood and from mononuclear cells from peripheral blood have also been disclosed. See Van Tendeloo et al., *Gene Ther.* 5: 700-707 (1998).

Dendritic cells may also be treated to induce maturation or activation, e.g., by culturing, preferably in the presence of a specific growth or stimulatory factor or factors. In the examples below, dendritic cells are modified by culturing with GM-CSF. Additional techniques relating to the preparation of dendritic cells can be found, for example, in U.S. Pat. Nos. 5,788,963, 5,962,318, and 5,851,756, the disclosures of which are herein incorporated by reference.

The procedures for transfecting dendritic cells with polynucleotides are known to persons skilled in the art. For example, a dendritic cell may be transfected by incubating with the polynucleotide in a solution for a time and at a temperature sufficient for transfection to occur. In some embodiments, dendritic cells and polynucleotides are incubated for 24 hours at 37° C. in a humidified $CO_2$ incubator. Expression of the polynucleotide of interest after transfection into dendritic cells may be confirmed by immunoassays or biological assays. For example, expression of introduced polynucleotides into cells may be confirmed by detecting the binding to the cells of labeled antibodies specific for the antigens of interest using assays well known in the art such as FACS (Fluorescent Activated Cell Sorting) or ELISA (enzyme-linked immunoabsorbent assay) or by simply by staining (e.g., with (β-gal) and determining cell counts. T cell activation may be detected by various known methods, including measuring changes in the proliferation of T cells, killing of target cells and secretion of certain regulatory factors, such as lymphokines, expression of mRNA of certain immunoregulatory molecules, or a combination of these.

In some embodiments, dendritic cells isolated from a patient are cultured, transfected in vitro and administered back to the patient to stimulate an immune response, including T cell activation. As such, the dendritic cells constitute a vaccine and/or immunotherapeutic agent. As an example, dendritic cells presenting antigen are administered, via intravenous infusion, at a dose of, for example, about $10^6$ to $10^8$ cells. The immune response of the patient can be monitored. Infusion can be repeated at desired intervals based upon the patient's immune response.

Below are examples of specific embodiments for carrying out the present invention. The examples are offered for illustrative purposes only, and are not intended to limit the scope of the present invention in any way.

EXAMPLES

Example 1 Construction of the Alphavirus Expression Vector

Construction of vector.

For construction of the expression vector pT7/NSP1-4/HygEGFP, an in-fusion cloning kit was used to clone different fragments into vector pTNT. Briefly, pTNT was first cut with SmaI and gel purified. Fragments for IRES, NSP1-4, HygEGFP were PCR amplified using phusion enzyme from plasmids pCITE-2a, pSmart2a and pHy-gEGFP. Primers used for PCR amplifications were designed using the online tool from Clontech and contain 15 bp overlaps either with vector or with the adjacent fragments. Purified vector and fragments were mixed together and co-incubated with infusion enzyme mix for 15 minutes at 50° C. The resultant reaction was used for transformation.

Primer sequences for PCR amplification:
1. Primers for first IRES fragment which is for 5'-cap independent invivo expression:

```
TNT-IRES FW Primer (F1_FW)
                                    (SEQ ID NO: 9)
CTCTAGAGTCGACCCgttattttccaccatattgcc IRES-NSP RV Primer (F1_RV)
                                    (SEQ ID NO: 10)
TCACACATCCGCCATaaaggaaaaccacgtcccc
```

2. Primers for NSP1-4:

```
NSP FW Primer (F2_FW)
                                    (SEQ ID NO: 11)
ATGGCGGATGTGTGACATA NSP-IRES RV Primer (F2_RV)
                                    (SEQ ID NO: 12)
AAATAACATTTAAATcgtagaggtgtataacagg
```

3. Primers for second IRES fragment which is used as an internal ribosomal entry site so the target gene and HygEGFP can both be expressed under the subgenomic promoter:

```
IRES FW Primer (F3_FW)
                                     (SEQ ID NO: 13)
ATTTAAATgttattttccaccatattgccgtatttggc IRES-Hyg RV Primer (F3_RV)
                                     (SEQ ID NO: 14)
TTCAGGCTTTTTCAtaaaggaaaaccacgtcccc
```

4. Primers for HygEGFP:

```
Hyg FW Primer (F4_FW)
(SEQ ID NO: 15)
ATGAAAAAGCCTGAACTCAC

Hyg-TNT RV Primer (F4_RV)
(SEQ ID NO: 16)
TTTTTGCGGCCGCCCcttgtacagctcgtccatg
```

Note: Upper case letters in the primer sequence indicate overlap sequence.

T7 RNA polymerase prebound to DNA for efficient gene expression

The vector pT7/NSP1-4/HygEGFP is complexed with T7 RNA polymerase in a buffer solution, such as saline, PBS or DMEM. The solution is injected into mouse tail, liver, leg muscles, cerebrospinal fluids or intravenously. After a certain time, gene expression is assessed by sacrificing the animal, and removing a portion of a specific tissue. The EGFP is used as a marker for indicating the gene expression level. The same procedure is performed with a solution containing the vector only as a control.

It is expected that the sample from mouse injected with solution containing the vector and prebound T7 RNA polymerase shows a high level of fluorescence intensity due to high level expression of the EGFP. It is also expected that the EGFP expression is detectable for an extended period of time, for example, at least one week. On the other hand, the control sample is expected to exhibit no fluorescence, due to no EGFP expression.

Example 3 Establishment of Human iPS Cells Using the Gene Expression System

Four human genes encoding reprograming factors Klf4, Oct 3/4, Sox2, and c-Myc are cloned into the vector, and introduced into the cells with a prebound RNA polymerase. On day 7 after infection, cells are collected and then are reseeded on feeder cells, for example, $5\times10^5$ cells/100-mm dish. As feeder cells, SNL cells (McMahon, A. P. & Bradley, A. *Cell* 62, 1073-1085 (1990)) treated with mitomycin C to cease cell division are used. From day 10 after infection, cells are cultured in medium prepared by adding recombinant human bFGF (WAKO, Japan) to medium for primate ES cell culture (ReproCELL, Japan). The transfection is further confirmed by using a marker gene.

The clones are inserted into the testis of a Scid mouse to examine its pluripotency. Specifically, human iPS cell clone is cultured in a medium for primate ES cell culture (ReproCELL, COSMO BIO, both Japan) containing recombinant human bFGF and an Rho kinase inhibitor Y-27632. One hour later, cells are treated with collagen IV and then collected. Cells are then centrifuged, collected, and suspended in DMEM/F12 containing Y-27632. Confluent cells (100-mm dish) are injected into the testis of a Scid mouse. Two to three months later, tumors are cut into pieces and then fixed with a PBS buffer containing 4% formaldehyde. Paraffin-embedded tissues are sliced and then stained with hematoxylin-eosin. The tumor is expected to be composed of a plurality of types of cells and show differentiation into multiple germ layers, for example neural tube tissue, cartilage tissue, and intestine-like epithelial structure. Thus, the pluripotency of iPS cells is expected to be observed.

Example 4 Influenza Virus Vaccine Activity In Vitro

DNA encoding influenza virus antigen hemagglutinin (HA) is cloned into the vector pT7/NSP1-4/Hyg vector. The influenza virus genes may be generated in a similar manner by one of skill in the art.

To demonstrate stimulation of flu antigen-specific immune response, a solution containing the vector with influenza antigen HA prebound with T7 RNA polymerase is used to immunize BALB/c mice in parallel with commercial subunit FLU vaccine antigen. The solution is administered intramuscularly twice and HA specific serum antibody responses are determined by standard ELISA assay following each immunization. An example ELISA assay is as follows: flat-bottom plates are coated overnight at 4° C. with a PBS solution containing 2.5 μg/ml monovalent subunit influenza vaccine preparation or the solution containing the vector and prebound T7 RNA polymerase. Plates are then washed three times with PBS (pH7.2) supplemented with 0.05% Tween-20 (PBS-T). After washing wells are blocked against non-specific binding using 5% (w/v) dry milk in PBS-T for 1 hour at 37° C. Sample sera are serially diluted in PBS-T by three fold starting from 1:50. After incubation with diluted sera at for 90 minutes at 37° C., plates are rinsed three times with PBS-T.

Plates are further incubated with alkaline phosphatase conjugated goat anti-mouse Ig, IgG1, or IgG2a diluted in PBS-T for 1 hour at 37° C., After extensive washing with PBS-T, 100 μl of a chromogen-substrate solution, paranitrophenylphosphate 1 mg/ml in diethanolamine, are added to each well. Then, the plate is read after 20 min at 405 nm using SpectraMax® (Molecular Devices, CA). For calculation of titers, a crit-off value is defined as the optical density (OD) value of average of PBS controls plus 3x their standard deviation. Antibody titers are then calculated as dilutions of which the samples generate OD of the cut-off value. It is expected that the sample with the vector and prebound T7 RNA polymerase is highly potent at both doses tested and of greater immunogenicity than the commercial subunit influenza vaccine.

Example 5 Influenza Virus Vaccine Activity In Vivo

Protection from influenza virus is tested in animal models challenged with the vector expressing influenza antigen HA, and prebound to T7 RNA polymerase. Balb/c mice are divided into two groups with 10 mice in each group. Either a solution containing the vector expressing influenza antigen HA prebound with T7 RNA polymerase or commercially available subunit influenza vaccine is used to challenge the mice of each group. Mice are immunized twice with an interval of 3 weeks. Two weeks after the second immunization, mice are challenged with live influenza viruses by administration intranasally in the upper respiratory tract.

Animals are monitored for mortality for 2 weeks from the day of challenge. The mice injected with the solution contain the vector with prebound T7 RNA polymerase are expected to exhibit higher degree of protection from intransal influenza challenge compared to mice immunized with commercially available subunit vaccine.

Example 6 Immunization of Mice with the Gene Expression System Elicits T Cell Immune Response The DNA with sequence encoding tyrosinase, tyrosinase-related protein 1(TRP-1), or tyrosinase-related protein 2 (TRP-2) is cloned into the vector, and expression of the gene of interest is confirmed by in vitro expression assays, such as ELISA. Dendritic cells can be prepared according to suitable procedures known in the art. An example is included here for demonstration. Peripheral blood is obtained from volunteer donors by venipuncture and diluted 1:2 with phosphate buffered saline (PBS). Peripheral blood mononuclear cells (PBMCs) are isolated by centrifugation over lymphocyte separation medium (ICN Biomedicals, Aurora, Ohio), washed twice with PBS, and resuspended in serum-free AIM-V media (Invitrogen, Carlsbad, Calif.). Monocytes are enriched by culturing $10^7$ PBMCs/well in 6-well tissue culture plates for 2 hours. Nonadherent PBMCs are removed and cryopreserved in 90% fetal bovine serum/10% DMSO The vectors encoding tyrosinase, TRP-1, or TRP-2 is used to transfect dendritic cells. The ability of transfected dendritic cells activate specific CD4 and CD8 T cells is tested. It is expected that the transfected dendritic cells show a strong T cell activation.

Murine Bone Marrow DC Culture and Transfection

The tibias and femurs of C57BL/6 mice were flushed with ice cold PBS through a 70 μm-wide cut-off cell strainer. RBCs were lysed with ammonium chloride Tris buffer for 3 min at 37° C. Cells were centrifuged for 5 minutes at 1400 rpm and the cells were suspended in DC-media (RPMI supplemented with 5% FCS, 1x nonessential amino acids, 2 mM L glutamine, 500 nM 2-ME, 100 U/ml penicillin/streptomycin, 20 μg/ml gentamycin), 150 U/ml GM-CSF and 75 U/ml IL-4. $3\times10^6$ cells were placed in 6-well plates containing 5 ml DC-media and cultured for 6 days. At day7, the nonadherent cells were harvested (immature day 7 DCs), washed, and transfected with plasmids using lipofectamine or nucleofection. Transfected cells were suspended in DC medium supplemented with 10 ng/mL tumor necrosis factor-α (TNF-α) and cultured for 2-3 day for further maturation.

CTL Priming in Mice

Naive, C57BL/6 mice were immunized i.v. with $5\times105$ transfected DC/mouse in 200 μl of PBS, two times at 14-day intervals. Splenocytes were harvested 12-14 days after the final immunization and depleted of RBCs with ammonium chloride Tris buffer. Splenocytes ($10^7$) were cultured with $5\times10^5$ stimulator B16/F0 cells pretreated with IFN-Y and irradiated at 7500 rads in 5 ml of Iscove's modified Dulbecco's medium with 10% FCS, 1 mM sodium pyruvate, 100 IU/ml penicillin, 100 mg/ml streptomycin, and $5\times10^{-5}$M β-mercaptoethanol/well in a six-well tissue culture plate. Cells were cultured for 5 days at 37° C. and 5% CO2. Effector splenocytes were harvested on day 5 on Histopaque 1083 gradient prior to use in a CTL assay.

In Vitro Cytotoxicity Assay (CD8)

Target cells ($5\text{-}10\times10^6$ B16 F0) were labeled with europium for 20 min at 4° C. Europium-labeled targets ($10^4$) and serial dilutions of effector cells at varying E:T were incubated in 200 μl of complete RPMI 1640. The plates were centrifuged at 500 g for 3 min and incubated at 37° C. for 4 h. Fifty μl of the supernatant were harvested, and europium release was measured by time resolved fluorescence. Specific cytotoxic activity was determined using the formula:

% specific release=Experimental release−spontaneous release/Total release−spontaneous release Spontaneous release of the target cells was <25% of total release by detergent in all assays.

For comparison, splenocytes from mice primed with non-transfected DC were used. CD4+ T-cell purification and bioassay for IL-2/IL-4 production. For CD4+ T-cell purification, nylon wool-enriched spleen T cells were further treated by incubating with ascites containing MAbs against B cells (B220) and CD8+ T cells (2.43) plus complement at 37° C. for 90 min and then washed 3 times. Phenotypic analysis with flow cytometry was used to analyze the purity of isolated CD4+ T cells. Purified CD4+ T cells were stimulated in vitro with irradiated (3,000 rad) transfected DC or non-transfected DC cells at a T cell/DC cell ratio of 20:1 for 24 hr and the supernatants collected at the end of incubation. To limit non-specific cytokine release, CD4+ T cells were purified in FBS-free medium and APC cells prepared in serum-free medium or in the presence of 2% murine serum. Induction of cytokine was performed in FBS-free AIM-V medium. IL-2/IL-4 activity was determined by the ability to support the growth of the CTLL cell line. Because both IL-2 and IL-4 support the growth of CTLL cells, cytokine activity in the supernatants was not distinguished and, thus, was designated IL-2/IL-4. Alternatively, the quantities of IL-2 and IL-4 can be measured by ELISA.

SEQUENCE LISTING

SEQ ID NO: 1: Sequence of the plasmid pT7/NSP1-4/HygEGFP
gggcggccgcaaaaaaaaaaaaaaaaaaaaaaaaaaaaactagcataaccccttggggcctctaaacgggtcttgagggqttt
tttggatccgggctggcgtaatagcgaagaggcccgcaccgatcgcccttcccaacagttgcgcagcctgaatggcgaatggac
gcgccctgtagcggcgcattaagcgcggcgggtgtggtggttacgcgcagcgtgaccgctacacttgccagcgccctagcgccc
gctcctttcgctttcttcccttcctttctcgccacgttcgccggctttccccgtcaagctctaaatcggggctcccttaggg
ttccgatttagtgctttacggcacctcgaccccaaaaaacttgattagggtgatggttcacgtagtgggccatcgccctgatag
acggttttcgccctttgacgttggagtccacgttctttaatagtggactcttgttccaaactggaacaacactcaaccctatc
tcggtctattcttttgatttataagggattttgccgatttcggcctattggttaaaaaatgagctgatttaacaaaaatttaac
gcgaattttaacaaaatattaacgcttacaatttcctgatgcggtatttctccttacgcatctgtgcggtatttcacaccgca
tatggtgcactctcagtacaatctgctctgatgccgcatagttaagccagccccgacacccgccaacacccgctgacgcgccct
gacgggcttgtctgctcccggcatccgcttacagacaagctgtgaccgtctccgggagctgcatgtgtcagaggttttcaccgt
catcaccgaaacgcgcgagacgaaagggcctcgtgatacgcctatttttataggttaatgtcatgataataatggtttcttaga
cgtcaggtggcacttttcggggaaatgtgcgcggaacccctatttgtttattttctaaatacattcaaatatgtatccgctca
tgagacaataaccctgataaatgcttcaataatattgaaaaaggaagagtatgagtattcaacatttccgtgtcgcccttattc
cctttttgcggcattttgccttcctgtttttgctcacccagaaacgctggtgaaagtaaaagatgctgaagatcagttgggtg
cacgagtgggttacatcgaactggatctcaacagcggtaagatccttgagagtttttcgccccgaagaacgttttccaatgatga
gcacttttaaagttctgctatgtggcgcggtattatcccgtattgacgccgggcaagagcaactcggtcgccgcatacactatt
ctcagaatgacttggttgagtactcaccagtcacagaaaagcatcttacggatggcatgacagtaagagaattatgcagtgctg
ccataaccatgagtgataacactgcggccaacttacttctgacaacgatcggaggaccgaaggagctaaccgcttttttgcaca
acatggggatcatgtaactcgccttgatcgttgggaaccggagctgaatgaagccataccaaacgacgagcgtgacaccacga
tgcctgtagcaatggcaacaacgttgcgcaaactattaactggcgaactacttactctagctcccggcaacaattaatagact
ggatggaggcggataaagttgcaggaccacttctgcgctcggcccttccggctggctggtttattgctgataaatctggagccg
gtgagcgtgggtctcgcggtatcattgcagcactggggccagatggtaagccctcccgtatcgtagttatctacacgacgggga
gtcaggcaactatggatgaacgaaatagacagatcgctgagataggtgcctcactgattaagcattggtaactgtcagaccaag
tttactcatatatactttagattgatttaaaacttcatttttaatttaaaaggatctaggtgaagatcctttttgataatctca
tgaccaaaatcccttaacgtgagttttcgttccactgagcgtcagaccccgtagaaaagatcaaaggatcttcttgagatcctt
tttttctgcgcgtaatctgctgcttgcaaacaaaaaaaccaccgctaccagcggtggtttgtttgccggatcaagagctaccaa
ctcttttccgaaggtaactggcttcagcagagcgcagataccaaatactgttcttctagtgtagccgtagttaggccaccact
tcaagaactctgtagcaccgcctacatacctcgctctgctaatcctgttaccagtggctgctgccagtggcgataagtcgtgtc
ttaccgggttggactcaagacgatagttaccggataaggcgcagcggtcgggctgaacggggggttcgtgcacacagcccagct
tggagcgaacgacctacaccgaactgagatacctacagcgtgagctatgagaaagcgccacgcttcccgaagggagaaaggcgg
acaggtatccggtaagcggcagggtcggaacaggagagcgcacgagggagcttccaggggaaacgcctggtatctttatagtc
ctgtcgggtttcgccacctctgacttgagcgtcgatttttgtgatgctcgtcaggggggcggagccatggaaaaacgccagca
acgcggcctttttacggttcctggccttttgctggccttttgctcacatggctcgacagattcttaaggctagagtacttaatac
gactcactatagggctagcatttaggtgacactatagaatacaagctacttgttcttttgcactcgagaattcacgcgtggtac
ctctagagtcgacccgttatttttccaccatattgccgtcttttggcaatgtgagggcccggaaacctggccctgtcttcttgac
gagcattcctaggggtctttccctctcgccaaaggaatgcaaggtctgttgaatgtcgtgaaggaagcagttcctctgtgaagc
ttcttgaagacaaacaacgtctgtagcgaccctttcaggcagcggaaccccccacctggcgacaggtgcctctgcggcaaaa
gccacgtgtataagatacacctgcaaaggcggcacaacccagtgccacgttgtgagttggatagttgtggaaagagtcaaatg
gctctcctcaagcgtattcaacaagggctgaaggatgcccagaaggtacccccattgtatggatctgatctggggcctcggtg
cacatgctttacatgtgtttagtcgaggttaaaaaacgtctaggccccccgaaccacggggacgtggttttcctttatggcgga
tgtgtgacatacacgacgccaaaagattttgttccagctcctgccacctccgctacgcgagagattaaccacccacgatgccg
ccaaagtgcatgttgatattgaggctgacagcccattcatcaagtctttgcagaaggcatttccgtcgttcgaggtggagtcat
tgcaggtcacaccaaatgaccatgcaaatgccagagcattttcgcacctggctaccaaattgatcgagcaggagactgacaaag
acacactcatcttggatatcggcagtgcgccttccaggagaatgatgtctacgcacaaataccactgcgtatgccccatgcgca
gcgcagaagaccccgaaaggctcgatagctacgcaaagaaactggcagcggcctccgggaaggtgctgatagagagatcgcag
gaaaaatcaccgacctgcagaccgtcatggctacgccagacgctgaatcctctaccttttgcctgcatacagacgtcacgtgtc
gtacggcagccgaagtggccgtataccaggacgtgtatgctgtacatgcaccaacatcgctgtaccatcaggcgatgaaggtg
tcagaacggcgtattggattgggtttgacaccaccccgtttatgtttgacgcgctagcaggcgcgtatccaaacctacgccacaa
actgggcgacgagcaggtgttacaggccaggaacataggactgtgtgcagcatcctgactgagggaagactcggcaaactgt
ccattctccgcaagaagcaattgaaaccttgcgcacacagtcatgtctcggtaggatctacattgtacactgagagcagaaagc
tactgaggagctggcacttaccctccgtattccacctgaaaggtaaacaatcctttacctgtaggtgcgataccatcgtatcat
gtgaagggtacgtagttaagaaaatcactatgtgccccggcctgtacggtaaaacggtagggtacgccgtgacgtatcacgcgg
agggattcctagtgtgcaagaccacacactgtcaaaggagaaagagtctcattccctgtatgcacctacctgcccctcaacca
tctgtgatcaaatgactggcatactagcgaccgacgtcacaccgggagacgcacagaagttgttagtgggattgaatcagagga
tagttgtgaacggaagaacacagcgaaacactaacacgatgaagaactatctgcttccgattgtggccgtcgcatttagcaagt
gggcgagggaatacaaggcagaccttgatgatgaaaaacctctgggtgtccgagagaggtcacttacttgctgctgcttgtggg
catttaaaacgaggaagatgcacaccatgtacaagaacacccagaacaatagtgaaggtgaaggtgcctttcagattaactcgt
tcgtcatcccgagcctatggtctacaggcctcgcaatcccagtcagtacacgcattaagtgctttttggccaagaagaccaagc
gagagttaatacctgttctcgacgcgtcgtcagccagggatgctgaacaagaggagaaggagaggttggaggccgagctgacta
gagaagccttaccaccctcgtccccatcgcgccggcggagacgggagtcgtcgacgtcgacgttgaagaactagagtatcacg
caggtgcaggggtcgtggaaacacctcgcagcgcgtttgaaagtccgcacagccgaacgacgtactactaggaaattacgtag
ttctgtccccgcagaccgtgctcaagagctccaagttggccccgtgcaccctctagagcaggtgaaataataacacata
acgggagggccggcggttaccaggtcgacggatatgacggcagggtcctactaccatgtggatcggccattccggtccctgagt
ttcaagctttgagcgagagcgccactatggtgtacaacgaaagggagttcgtcaacaggaaactataccatattgccgttcacg
gaccgtcgctgaacaccgacgaggagatcagcacgcgcaaggaaactgaaggcgccgagtacgtgttcgacgtagata
aaaaatgctgcgtcaagagaggaagcgtcgggtttggtgttggtgggagagctaaccaaccccccgttccatgaattcgcct
acgaagggctgaagatcaggccgtcggcaccataaagactacgtagtaggagtctttggggttccgggatcaggcaagtctg
ctattattaagagcctcgtgaccaaacacgatctggtcaccagcggcaagaaggagaactgccaggaaatagttaacgacgtga
agaagaccgcgggggaagggacaagtagggaaaacagtgactccatcctgctaaacgggtgtcgtcgtccgtggacatcctat
atgtggacgaggctttcgctagccattccggtactctgctgccctaattgctcttgttaaacctcggagcaaatggttctat
gcggagacccaagcaatgcggattcttcaatatgatgcagcttaaggtgaacttcaaccacaacatctgcactgaagtatgtc
ataaaagtatatccagacgttgcacgcgtccagtcacggccatcgtgtctacgttgcactacggaggcaagatgcgcacgacca
acccgtcaacaaacccataatcatagacaccaggagacaagccagtgcaggatgcgacgtgttaactgttcgtccgag
gctgggcaaagcagctgcagttggactaccgtggacacgaagtcatgcacagcagcatctcagggccctcacccgcaaaggg
tatacgccgtaaggcagaaggtgaatgaaaatcccttgtatgccctgctgtcggagcacgtgaattactactgctgacgcgcactg
aggataggctggtgtggaaaacgctggccggcgatccctggattaaggtcctatcaaacattccacagggtaactttacggcca
cattggaagaatggcaagaagaacacgacaaaataatgaaggtgattgaaggaccggctgcgcctgtggacgcgttccagaaca
aagcgaacgtgtgttgggcgaaaagcctggtgcctgtcctggacactgccggaatcagattgacagcagaggagtggagcacca

SEQUENCE LISTING

```
taattacagcatttaaggaggacagagcttactctccagtggtggccttgaatgaaatttgcaccaagtactatggagttgacc
tggacagtggcctgttttctgccccgaaggtgtccctgtattacgagaacaaccactgggataacagacctggtggaaggatgt
atggattcaatgccgcaacagctgccaggctggaagctagacataccttcctgaaggggcagtggcatacgggcaagcaggcag
ttatcgcagaaagaaaaatccaaccgctttctgtgctggacaatgtaattcctatcaaccgcaggctgccgcacgccctggtgg
ctgagtacaagacggttaaaggcagtagggttgagtggctggtcaataaagtaagagggtaccacgtcctgctggtgagtgagt
acaacctggctttgcctcgacgcagggtcacttggttgtcaccgctgaatgtcacaggcgccgataggtgctacgacctaagtt
taggactgccggctgacgccggcaggttcgacttggtctttgtgaacattcacacggaattcagaatccaccactaccagcagt
gtgtcgaccacgccatgaagctgcagatgcttgggggagatgcgctacgactgctaaaacccggcggcatcttgatgagagctt
acggatacgccgataaaatcagcgaagccgttgtttcctccttaagcagaaagttctcgtctgcaagagtgttgcgcccggatt
gtgtcaccagcaatacagaagtgttcttgctgttctccaactttgacaacggaaagagaccctctacgctacaccagatgaata
ccaagctgagtgccgtatgccgagaagccatgcacacggccgggtgtgcaccatcctacagagttaagagagcagacatag
ccacgtgcacagaagcggctgtggttaacgcagctaacgcccgtgaactgtaggggatggcgtatgcaggggccgtggcgaaga
aatggccgtcagcctttaagggagcagcaacaccagtgggcacaattaaaacagtcatgtgcggctcgtaccccgtcatccacg
ctgtagcgcctaatttctctgccacgaccagatattcagatatttgaagcggaaggggaccgcgaattggccgctgtctaccgg
gcagtggccgccgaagtaaacagactgtcactgagcagcgtagccatcccgctgctgtccacaggagtgttcagcggcggaaga
gataggctgcagcaatccctcaaccatctattcacagcaatggacgccacggacgctgacgtgaccatctactgcagagacaaa
agttgggagaagaaaatccaggaagccattgacatgaggacggctgtggagttgctcaatgatgacgtggagctgaccacagac
ttggtgagagtgcaccggacagcagcctggtgggtcgtaagggctacagtaccactgacgggtcgctgtactcgtactttgaa
ggtacgaaattcaaccaggctgctattgatatggcagagatactgacgttgtggcccagactgcaagaggcaaacgaacagata
tgcctatacgcgctgggcgaaacaatggacaacatcagatccaaatgtccggtgaacgattccgattcatcaacacctcccagg
acagtgccctgcctgtgccgctacgcaatgacagcagaacggatcgcccgccttaggtcacaccaagttaaaagcatggtggtt
tgctcatcttttcccctcccgaaatccatgtagatggggtgcagaaggtaaagtgcgagaaggttctcctgttcgacccgacg
gtaccttcagtggttagtccgcggaagtatgccgcatctacgacggaccactcagatcggtcgttacgagggtttgacttggac
tggaccaccgactcgtcttccactgccagcgataccatgtccgctaccccagtttgcagtcgtgtgacatcgactcgatctacgag
ccaatggctcccatagtagtgacggctgacgtacaccctgaaccgccaggcatcgcggacctggcggcagatgtgcaccctgaa
cccgcagaccatgtggacctcgagaacccgattcctccaccgcgcccgaagagagctgcataccttgcctcccgcgcggcggag
cgaccggtgccggcgccgagaaagccgacgcctgcccaaggactgcgtttaggaacaagctgcctttgacgttcggcgacttt
gacgagcacgaggtcgatgcgttggcctccgggattactttcggagactttcgacgacgtcctgcgactaggccgcgcgggtgca
tatattttctcctcggacactggcagcggacatttacaacaaaaatccgttaggcagcacaatctccagtgcgcacaactggat
gcggtccaggaggagaaaatgtaccgcaaaattggatactgagagggagaagctgttgctgctgaaaatgcagatgcaccca
tcggaggctaataagagtcgataccagtctcgcaaagtggagaacatgaaagccacggtggtggacaggctcacatcggggcc
agattgtacacgggagcggacgtaggccgcataccaacatacgcggttcggtaccccccgccccgtgtactccccctaccgtgatc
gaaagattctcaagccccgatgtagcaatcgcagcgtgcaacgaatacctatccagaaattaccaacagtggcgtcgtaccag
ataacagatgaatacgacgcatacttggacatggttgacgggtcggatagttgcttggacagagcgacattctgcccggcgaag
ctccggtgctacccgaaacatcatgcgtaccaccagccgactgtacgcagtgccgtcccgtcacccttcagaacacactacag
aacgtgctagcggccgccaccaagagaaactgcaacgtcacgcaaatgcgagaactacccaccatggactcggcagtgttcaac
gtggagtgcttcaagcgctatgcctgctccggagaatattgggaagaatatgctaaacaacctatcccggataaccactgagaac
atcactacctatgtgaccaaattgaaaggcccgaaagtgctgccttgttcgctaagacccacaacttggttccgctgcaggag
gttcccatggacagattcacggtcgacatgaaacgagatgtcaaagtcactccagggacgaaacacacagaggaaagacccaaa
gtccaggtaattcaagcagcggagccattggcgaccgcttacctgtgcggcatccacaggaattagtaaggagactaaatgct
gtgttacgccctaacgtgcacacattgtttgatatgtcggccgaagactttgacgcgatcgccctctcacttccaccagga
gacccggttctagagacggacattgcatcattcgacaaaagccaggacgactccttggctcttacaggtttaatgatcctcgaa
gatctaggggtggatcagtacctgctggacttgatcgaggcagcctttggggaaatatccagctgtcacctaccaactggcacg
cgcttcaagttcggagctatgatgaaatcgggcatgtttctgactttgtttattaacactgttttgaacatcaccatagcaagc
agggtactggagcagagactcactgactccgcctgtgcggccttcatcggcgacgaacatcgttcacggagtgatctcacgag
aagctgatggcggagaggtgcgcgtcgtgggcaacatggaggtgaagatcattgacgctgtcatgggcgaaaaaccccccatat
ttttgtggggattcatagtttttgacagcgtcacacagaccgcctgccgtgtttcagacccacttaagcgcctgttcaagttg
ggtaagccgctaacagctgaagacaagcaggacgaagacaggcgacgagcactgagtgacgaggttagcaagtggttccggaca
ggcttggggcgaactggaggtggcactaacatctaggtatgaggtagagggctgcaaaagtatcctcatagccatggccacc
ttggcgagggacattaaggcgtttaagaaATTGAGAGGACCTGTTATACACCTctacgatttaaatgttattttccaccatatt
gccgtcttttggcaatgtgagggcccggaaacctggccctgtcttcttgacgagcattcctagggggtcttcccctctcgccaa
aggaatgcaaggtctgttgaatgtcgtgaaggaagcagttcctctgaagcttcttgaagacaaacaacgtctgtagcgaccat
tgcaggcagcggaacccccccacctggcgacaggtgcctctgcggccaaaaggccacgtgtataagatacacctgcaaaggcggca
caacccccagtgccacgttgtgagttggatagttgtgaaagagtcaaatggctctcctcaagcgtattcaacaaggggctgaag
gatgcccagaaggtacccattgtatgggatctgatctggggcctcggtcgcacatgattacatgtgtttagtcgaggttaaaaa
acgtctaggcccccgaaccacggggacgtggttttccttatgaaaaagcctgaactcaccgcgacgtctgtcgagaagtttc
tgatcgaaaagttcgacagcgtctccgacctgatgcagctctcggagggcgaagaatctcgtgcttcagcttcgatgtaggag
ggcgtggatatgtcctgcgggtaaatagctgcgccgatggtttctacaaagatcgttatttcggcgacttttgcatcggccg
cgctcccgattccggaagtgcttgacattggggaattcagcgagagcctgacctattgcatctcccgccgtgcacagggtgtca
cgttgcaagacctgcctgaaaccgaactgcccgctgttctgcagccggtcgcggaggccatggatgcgatcgctgcggccgatc
ttagccagacgagcgggttcggcccattcggaccgcaaggaatcggtcaatacactacatggcgtgatttcatatgcgcgattg
ctgatccccatgtgtatcactggcaaactgtgatggacgacaccgtcagtgcgtccgtcgcgcaggctctcgatgagctgatgc
tttgggccgaggactgccccgaagtccggcacctcgtgcacggatttcggctccaacaatgtcctgacggacaatggccgca
taacagcggtcattgactggagcgaggcgatgttcggggattcccaatacgaggtcgccaacatcttcttctggaggccgtggt
tggcttgtatggagcagcagacgcgctacttcgagcggaggcatccggagcttgcaggatcgccgcggctccgggcgtatatgc
tccgcattggtatgaccaactctatcagagatggttgacggcaatttcgatgatgcagatgggcgcagggtcgatgcgacgcaa
tcgtccgatccggagccggactgcggcgtacacaaatcgcccgcagaagcgcggccgtctggaccgatggctgtgtagaag
tactcgccgatagtggaaaccgacgccccagcactcgtccgagggcaaaggaatagtgagcaaggcgaggagctgttcaccg
gggtggtgcccatcctggtcgagctggacggcgacgtaaacggccacaagttcagcgtgtccggcgagggcgagggcgatgcca
cctacggcaagctgaccctgaagttcatctgcaccaccggcaagctgcccgtgccctggcccaccctcgtgaccaccctgacct
acggcgtgcagtgcttcagccgctaccccgaccacatgaagcagcacgacttcttcaagtccgccatgcccgaaggctacgtcc
aggagcgcaccatcttcttcaaggacgacggcaactacaagacccgcgctgaagtcaagtttgagggcgacaccctggtgaacc
gcatcgagctgaagggcatcgacttcaaggaggacggcaacatcctggggcacaagctggagtacaactacaacagccacaacg
tctatatcatggccgacaagcagaagaacggcatcaaggtgaacttcaagatccgccacaacatcgaggacggcagcgtgcagc
tcgccgaccactaccagcagaacacccccatcggcgacggccccgtgctgctgcccgacaaccactacctgagcacccagtccg
ccctgagcaaagaccccaacgagaagcgcgatcacatggtcctgctggagttcgtgaccgccgccgggatcactctcggcatgg
acgagctgtacaag
```

SEQUENCE LISTING

SEQ ID NO: 2: Poly A and T7 terminator
aaaaaaaaaaaaaaaaaaaaaaaaaaaaaaaactagcataacccatgggcctctaaacgggtcttgagggttttttg SEQ ID NO: 3 T7 promoter
Taatacgactcactatagg SEQ ID NO: 4: IRES Sequence
Gttattttccaccatattgccgtatttggcaatgtgagggcccggaaacctggcctgtatcttgacgagcattcctaggggta
ttcccctctcgccaaaggaatgcaaggtctgttgaatgtcgtgaaggaagcagttcctctggaagatcttgaagacaaacaacg
tctgtagcgaccctttgcaggcagcggaaccccccacctggcgacaggtgcctctgcggccaaaagccacgtgtataagataca
cctgcaaaggcggcacaacccagtgccacgttgtgagttggatagttgtgggaaagagtcaaatggctctcctcaagcgtattc
aacaaggggctgaaggatgcccagaaggtaccccattgtatgggatctgatctggggcctcggtgcacatgattacatgtgttt
agtcgaggttaaaaaacgtctaggccccccgaaccacggggacgtggttttcctttt SEQ ID NO: 5: Alphavirus RNA replicase nsp 1-4
atggcggatgtgtgacatacacgacgccaaaagattttgttccagctcctgccacctccgctacgcgagagattaaccacccac
gatggccgccaaagtgcatgttgatattgaggctgacagcccattcatcaagtctttgcagaaggcatttccgtcgttcgaggt
ggagtcattgcaggtcacaccaaatgaccatgcaaatgccagagcattttcgcacctggctaccaaattgatcgagcaggagac
tgacaaagacacactcatcttggatatcggcagtgcgccttccaggagaatgatgtctatgcgcacaaataccactgcgtatgcc
tatgcgcagcgcagaagaccccgaaaggctcgatagctacgcaaagaaactggcagcggcctccgggaaggtgctggatagaga
gatcgcaggaaaaatcaccgacctgcagaccgtcatggctacgcgcagacgctgaatctcctacctttgcctgcatacagacgt
cacgtgtcgtacggcagccgaagtggccgtataccaggacgtgtatgctgtacatgcaccaacatcgctgtaccatcaggcgat
gaaaggtgtcagaacggcgtattgattggttgacaccaccccgtttatgtttgacgcgctagcaggcgcgctatccaaccta
cgccacaaactgggccgacgagcaggtgttacaggccaggaacataggacgtgtgtgcagcatccttgactgagggaagactcgg
caaactgtccattctcccgcaagaagcaattgaaaccttgcgacacagtcatgttctcggtaggatctacattgtacactgagag
cagaaagctactgaggagctggcacttaccctccgtattccacctgaaaggtaaacaatcctttacctgtaggtgcgataccat
cgtatcatgtgaaggtacgtagttaagaaaatcactatgtgccccggcctgtacggtaaacggtagggtacgccgtgacgta
tcacgcggagggattcctagtgtgcaagaccacagacactgtcaaaggagaaagagtctcattccctgtatgcacctacgtccc
ctcaaccatctgtgatcaaatgactggcatactagcgaccgacgtcacaccggaggacgcacagaagttgttagtgggattgaa
tcagaggatagttgtgaacggaagaacacagcgaaacactaacacgatgaagaactatctgatccgattgtggccgtcgcattt
agcaagtgggcgagggaatacaaggcagaccttgatgatgaaaaaacctctgggtgtccgagagaggtcacttacttgctgctgc
ttgtgggcatttaaaacggaagaagatgcacaccatgtacaagaaaccagacaccccagacaatagtgaaggtgccttcagagtt
aactcgttcgtcatcccgagcctatggtctacaggcctcgcaatcccagtcagatcacgcattaagatgcttttggccaagaag
accaagcgagagttaatacctgttctcgacgcgtcgtcagccagggatgctgaacaagaggagaaggagaggttggaggccgag
ctgactagagaagccttaccacccctcgtcccatcgcgccggcggagacggagtcgtcgacgtcgacgttgaagaactagag
tatcacgcaggtgcaggggtcgtggaaacacctcgcagcgcgttgaaagtcaccgcaacggcgaacgacgtactactaggaaat
tacgtagttctgtccccgcagaccgtgctcaagagctccaagttggcccccgtgcaccctctagcaggcaggtgaaaataata
acacataacggggagggccggcggttaccaggtcgacggatatgacggcagggtcctactaccatgtggatcggccattccggtc
cctgagtttcaagctttgagcgagagcgccactatggtgtacaacgaaagggagttcgtcaacaggaaactataccatattgcc
gttcacggaccgtcgctgaacacctgacgaggagaactacgagaaagtcagagctgaaagaactgacgccgagtacgtgttcgac
gtagataaaaaatgctgcgtcaagagagaggaagcgtcgggtttggtgttggtgggagagctaaccaaccccccgttccatgaa
ttcgcctacgaagggctgaagatcaggccgtcggcaccatataagactacagtagtaggagtctttggggttccgggatcaggc
aagtctgctattattaagagcctcgtgaccaaacacgatctggtcaccagcggcaagaaggagaactgccaggaaatagttaac
gacgtgaagaagcaccgcgggaagggagacaagtagggaaaacagtgactcctcctgctaaacgggtgtcgtcgtgccgtggac
atcctatatgtggacgaggcttcgctagccattccggtactctgctggccctaattgctcttgttaaacctcggagcaaagtg
gtgttatgcggagaccccaagcaatgcggattcttcaatatgatgcagcttaaggtgaacttcaaccacaacatctgcactgaa
gtatgtcataaaagtatatccagacgttgcacgcgtccagtcacggccatcgtgtctacgttgcactacggaggcaagatgcgc
acgaccaacccgtgcaacaaacccataatcatagacaccacaggacagaccaagcccaagcaggagacatcgtgttaacatgc
ttccgaggctgggcaaagcagctgcagttggactaccgtggacacgaagtcatgacagcagcagcatctcaggggctcacccgc
aaaggggtatacgccgtaaggcagaaggtgaatgaaaatcccttgtatgcccctgcgtcggagcacgtgaatgtactgctgacg
cgcactgaggataggctggtgtggaaaacgctggccggcgatcctggattaaggtcctatcaaacattccacagggtaacttt
acggccacattggaagaatggcaagaagaacacgacaaaataatgaaggtgattgaaggaccggctgcgcctgtggacggttc
cagaacaaagcgaacgtgtgttgggcgaaaagctggtgcctgtcctggacactgccggaatcagattgacagcagaggagtgg
agcaccataattacagcatttaaggaggacagagctgactctccagtggtggccttgaatgaaattgcaccaagtactatgga
gttgacctggacagtggcctgtttctgccccgaaggtgtccctgtattacgagaacaaccactgggataacagaccgtggtga
aggatgtatggattcaatgccgcaacagctgccaggctggaagctagacataaccttcctgaaggggcagtggcatacgggcaag
caggcagttatcgcagaaagaaaaatccaaccgctttctgtgctgacaatgtaattcctatcaaccgcaggctgccgcacgcc
ctggtggctgagtacaagacggttaaaggcagtaggggttgagtggctggtcaataaagtaagaggtaccacgtcctgctggta
agtgagtacaacctggctttgcctcgacgcagggtcacttggttgtcaccgctgaatgtcacaggcgccgataggtgctacgac
ctaagtttaggactgccggctgacgccggcaggttcgacttggtctttgtgaacattcacggaattcagaatcaccactac
cagcagtgtgtcgaccacgccataaatgccggatgcttgggggacagctatgactgtcaaaaccccggcggcatcttgatg
agagcttacggatacgccgataaaatcagcgaagccgttgttctccttaagcgaaagttctctcgtctgcaagagtgttgcgc
ccggattgtgtcaccagcaatacagaagtgttcttgctgttctccaactttgacaacggaaagagaccctctacgctacaccag
atgaataccaagctgagtgccgtgtatgccggagaagccatgcacacggccgggtgtgcaccatcctacagagttaagagagca
gacatagccacgtgcacagaagcggctgtggttaacgcagctaacgcccgtggaactgtaggggatggcgtatgcagggccgtg
gcgaagaaatggccgtcagccttaaggagcagcaacaccagtggtgcattaaaaaacgtcatgtgcggcgtctaccccgcctc
atccacgctgtagcgcctaatttctctgccacgaccagatattcagatatttgaagcggaagggagaccgcgaattggccgctgt
ctaccgggcagtggccgccgaagtaaacagactgtcactgagcagcgctagccatcccgctgctgtccacaggagtgttcagcgg
cggaagagataggctgcagcaatccctcaaccatctattcacagcaatggacgccacggacgctgacgtgaccatctactgcag
agacaaagtggggagaagaaatccaggaagccattgacatgaggacggctgtggagttgctcaatgatgacgtggagctgac
cacagactggtgagagtgcaccccggacagcagcctggtgggtcgtaaggcgtactaccaccgagtgggtcgctgtactcgta
ctttgaaggtacgaaattcaaccaggctgctattgatatgcagaagatactgacgtgtgccccagactgcaagaggcaaacga
acagatatgcctatacgcgctgggcgaaacaatggacaacatcagatccaaatgtccggtgaacgattccgattcatcaacacc
tcccaggacagtgccctgcctgtgccgctacgcaatgacagcagaacggatcgcccgccttaggtcacaccaagttaaaagcat
ggtggtttgctcatctttttcccctcccgaaataccatgtagatggggtgcagaaggtaaagtgcgagaaggttctcctgttcga
cccgacggtaccttcagtggttagtccgcggaagtatgccgcatctacgacggaccactcagatcggtcgttacgagggtttga cttggactggaccaccgactcgtcttccactgccagcgataccatgtcgctacccagtttgcagtcgtgtgacatcgactcgat
ctacgagccaatggctcccatagtagtgacggctgacgtacaccctgaacccgcaggcatcgcggacctggcggcagatgtgca
ccctgaaccgcagaccatgtggacctcgagaacccgattcctccaccgcgcccgaagagagctgcataccttgcctcccgcgc
ggcggagcgaccggtgccggcgccgagaaagccgacgcctgcccaaggactgcgtttaggaacaagctgcctttgacgttcgg
cgactttgacgagcacgaggtcgatgcgttggcctccgggattactttcggagacttcgacgacgtcctgcgactaggccgcgc
gggtgcatatattttctcctcggacactggcagcggacatttacaacaaaaatccgttaggcagcacaatctccagtgcgcaca
actggatgcggtccaggaggagaaaatgtacccgccaaaattggatactgagagggagaagctgttgctgctgaaaatgcagat
gcacccatcggaggctaataagagtcgataccagtctcgcaaagtggagaacatgaaagccacggtggtggacaggctcacatc
gggggcagattgtacacgggagcggacgtaggccgcataccaacatacgcggttcggtaccccgccccgtgtactccctac
cgtgatcgaaagattctcaagcccgatgtagcaatcgcagcgtgcaacgaatacctatccagaaattacccaacagtggcgtc
gtaccagataacagatgaatacgacgcatacttggacatggttgacgggtcggatagttgcttggacagagcgacattctgccc
ggcgaagctccggtgctacccgaaacatcatgcgtaccaccagccgactgtacgcagtgccgtcccgtcacccttccagaacac
actacagaacgtgctagcggccgccaccaagagaaactgcaacgtcacgcaaatgcgagaactacccaccatggactcggcagt
gttcaacgtggagtgcttcaagcgctatgcctgctccggagaatattgggaagaatatgctaaacaacctatccggataaccac
tgagaacatcactacctatgtgaccaaattgaaaggcccgaaagctgctgccttgttcgctaagacccacaacttggttccgct
gcaggaggttcccatggacagattcacggtcgacatgaaacggagtgtcaaagtcactccagggacgaaacacacaggaagaag
acccaaagtccaggtaattcaagcagcggagccattggcgaccgcttacctgtgcggcatccacagggaattagtaaggagact
aaatgctgtgttacgccctaacgtgcacacattgtttgatatgtcggccgaagactttgacgcgatcatcgcctctcacttcca
cccaggagacccggttctagagacggacattgcatcattcgacaaaagccaggacgactccttggctcttacaggtttaatgat
cctcgaagatctaggggtggatcagtacctgctggacttgatcggaggcgccctttggggaaatatccagctgtcacctaccaac
tggcacgcgcttcaagttcggagctatgatgaaatcgggcatgtttctgactttgtttattaacactgtttgaacatcaccat
agcaagcagggtactggagcagagactcactgactccgcctgtgcggccttcatcggcgacgacaacatcgttcacggagtgat
ctccgacaagctgatggcgagaggtgcgcgtcgtgggtcaacatggaggtgaagatcattgacgctgtcatgggcgaaaaacc
cccatattttgtggggggattcatagttttttgacagcgtcacacagaccgcctgccgtgtttcagaccccacttaagcgcctgtt
caagttgggtaagccgctaacagctgaagacaagcaggacgaagacaggcgacgagcactgagtgacgaggttagcaagtggtt
ccggacaggcttgggggccgaactggaggtggcactaacatctaggtatgaggtagagggctgcaaaagtatcctcatagccat
ggccaccttggcgagggacattaaggcgtttaagaaattgagaggacctgttatacacctctacg SEQ ID NO: 6: Subgenomic promoter sequence from SFV
ATTGAGAGGACCTGTTATACACCT SEQ ID NO: 7: Hygromycin/EGFP fusion gene
atgaaaaagcctgaactcaccgcgacgtctgtcgagaagtttctgatcgaaaagttcgacagcgtctccgacctgatgcagctc
tcggagggcgaagaatctcgtgctttcagcttcgatgtaggagggcgtggatatgtcctgcgggtaaatagctgcgccgatggt
ttctacaaagatcgttatgtttatcggcactttgcatcggccgcgctcccgattccggaagtgcttgacattggggaattcagc
gagagcctgacctattgcatctcccgccgtgcacagggtgtcacgttgcaagacctgcctgaaaccgaactgcccgctgttctg
cagccggtcgcggaggccatggatgcgatcgctgcggccgatcttagccagacggacgggttcggcccattcggaccgcaagga
atcggtcaatacactacatggcgtgatttcatatgcgcgattgctgatcccatgtgtatcactggcaaactgtgatggacgac
accgtcagtgcgtccgtcgcgcaggctctcgatgagctgatgctttgggccgaggactgccccgaagtccggcacctcgtgcac
gcggatttcggctccaacaatgtcctgacggacaatggccgcataacagcggtcattgactggagcgaggcgatgttcggggat
tcccaatacgaggtcgccaacatcttcttctggaggccgtggttggcttgtatggagcagcagacgcgctacttcgagcggagg
catccggagcttgcaggatcgccgcggctccgggcgtatatgctccgcattggtcttgaccaactctatcagagcttggttgac
ggcaatttcgatgatgcagcttgggcgcagggtcgatgcgacgcaatcgtccgatccggagccgggactgtcgggcgtacacaa
atcgcccgcagaagcgcggccgtctggaccgatggctgtgtagaagtactcgccgatagtggaaaccgacgccccagcactcgt
ccgagggcaaaggaaatggtgagcaagggcgaggagctgttcaccggggtggtgcccatcctggtcgagctggacggcgacgta
aacggccacaagttcagcgtgtccggcgagggcgagggcgatgccacctacggcaagctgaccctgaagttcatctgcaccacc
ggcaagctgcccgtgccctggcccaccctcgtgaccaccctgacctacggcgtgcagtgcttcagccgctaccccgaccacatg
aagcagcacgacttcttcaagtccgccatgcccgaaggctacgtccaggagcgcaccatcttcttcaaggacgacggcaactac
aagacccgcgccgaggtgaagttcgagggcgacaccctggtgaaccgcatcgagctgaagggcatcgactttaaggaggacggc
aacatcctggggcacaagctggagtacaactacaacagccacaacgtctatatcatggccgacaagcagaagaacggcatcaag
gtgaacttcaagatccgccacaacatcgaggacggcagcgtgcagctcgccgaccactaccagcagaacacccccatcggcgac
ggccccgtgctgctgcccgacaaccactacctgagcacccagtccgccctgagcaaagaccccaacgagaagcgcgatcacatg
gtcctgctggagttcgtgaccgccgccgggatcactctcggcatggacgagctgtacaag SEQ ID NO: 8: Sequence of the non-cytopathic plasmid pT7/NSP1-4/HygEGFP
(Underlined letters at 8734 and 8940 indicate mutated nucleotides for mutation P718T
and R649H respectively)
atgaaaaagcctgaactcaccgcgacgtctgtcgagaagtttctgatcgaaaagttcgacagcgtctccgacctgatgcagctc
tcggagggcgaagaatctcgtgctttcagcttcgatgtaggagggcgtggatatgtcctgcgggtaaatagctgcgccgatggt
ttctacaaagatcgttatgtttatcggcactttgcatcggccgcgctcccgattccggaagtgcttgacattggggaattcagc
gagagcctgacctattgcatctcccgccgtgcacagggtgtcacgttgcaagacctgcctgaaaccgaactgcccgctgttctg
cagccggtcgcggaggccatggatgcgatcgctgcggccgatcttagccagacggacgggttcggcccattcggaccgcaagga
atcggtcaatacactacatggcgtgatttcatatgcgcgattgctgatcccatgtgtatcactggcaaactgtgatggacgac
accgtcagtgcgtccgtcgcgcaggctctcgatgagctgatgctttgggccgaggactgccccgaagtccggcacctcgtgcac
gcggatttcggctccaacaatgtcctgacggacaatggccgcataacagcggtcattgactggagcgaggcgatgttcggggat
tcccaatacgaggtcgccaacatcttcttctggaggccgtggttggcttgtatggagcagcagacgcgctacttcgagcggagg
catccggagcttgcaggatcgccgcggctccgggcgtatatgctccgcattggtcttgaccaactctatcagagcttggttgac
ggcaatttcgatgatgcagcttgggcgcagggtcgatgcgacgcaatcgtccgatccggagccgggactgtcgggcgtacacaa
atcgcccgcagaagcgcggccgtctggaccgatggctgtgtagaagtactcgccgatagtggaaaccgacgccccagcactcgt
ccgagggcaaaggaaatggtgagcaagggcgaggagctgttcaccggggtggtgcccatcctggtcgagctggacggcgacgta
aacggccacaagttcagcgtgtccggcgagggcgagggcgatgccacctacggcaagctgaccctgaagttcatctgcaccacc
ggcaagctgcccgtgccctggcccaccctcgtgaccaccctgacctacggcgtgcagtgcttcagccgctaccccgaccacatg
aagcagcacgacttcttcaagtccgccatgcccgaaggctacgtccaggagcgcaccatcttcttcaaggacgacggcaactac
aagacccgcgccgaggtgaagttcgagggcgacaccctggtgaaccgcatcgagctgaagggcatcgactttaaggaggacggc
aacatcctggggcacaagctggagtacaactacaacagccacaacgtctatatcatggccgacaagcagaagaacggcatcaag
gtgaacttcaagatccgccacaacatcgaggacggcagcgtgcagctcgccgaccactaccagcagaacacccccatcggcgac
ggccccgtgctgctgcccgacaaccactacctgagcacccagtccgccctgagcaaagaccccaacgagaagcgcgatcacatg

SEQUENCE LISTING

```
gtcctgctggagttcgtgaccgccgccgggatcactctcggcatggacgagctgtacaaggggcggccgcaaaaaaaaaaaaa
aaaaaaaaaaaaaaaactagcataaccccttggggcctctaaacgggtcttgaggggttttttggatccgggctggcgtaatag
cgaagaggcccgcaccgatcgcccttcccaacagttgcgcagcctgaatggcgaatggacgcgccctgtagcggcgcattaagc
gcggcgggtgtggtggttacgcgcagcgtgaccgctacacttgccagcgccctagcgcccgctcctttcgctttcttcccttcc
tttctcgccacgttcgccggctttccccgtcaagctctaaatcgggggctcccttagggttccgatttagtgctttacggcac
ctcgaccccaaaaaacttgattagggtgatggttcacgtagtgggccatcgcccgatagacggtttttcgccctttgacgttg
gagtccacgttcttttaatagtggactcttgttccaaactggaacaacactcaaccctatctcggtctattcttttgatttataa
gggatttccgatttcggcctattggttaaaaaatgagctgatttaacaaaaatttaacgcgaattttaacaaaatattaacgct
tacaatttcctgatgcggtattttctccttacgcatctgtgcggtatttcacaccgcatatggtgcactctcagtacaatctgc
tctgatgccgcatagttaagccagccccgacacccgccaacaccgctgacgcgccctgacgggcttgtctgctcccggcatcc
gcttacagacaagctgtgaccgtctccgggagctgcatgtgtcagaggttttcaccgtcatcaccgaaacgcgcgagacgaaag
ggcctcgtgatacgcctatttttataggttaatgtcatgataataagtgtttcttagacgtcaggtggcacttttcggggaaat
gtgcgcggaacccctatttgtttatttttctaaatacattcaaatatgtatccgctcatgagacaataaccctgataaatgctt
caataatattgaaaaaggaagagtatgagtattcaacatttccgtgtcgcccttattcctttttttgcggcattttgccttcctg
ttttgctcacccagaaacgctggtgaaagtaaaagatgctgaagatcagttgggtgcacgagtgggttacatcgaactggatc
tcaacagcggtaagatccttgagagttttcgccccgaagaacgttttccaatgatgagcacttttaaagttctgctatgtgcg
cggtattatcccgtattgacgccgggcaagagcaactcggtcgccgcatacactattctcagaatgacttggttgagtactcac
cagtcacagaaaagcatcttacggatggcatgacagtaagagaattatgcagtgctgccataaccatgagtgataacactgcgg
ccaacttacttctgacaacgatcggaggaccgaaggagctaaccgcttttttgcacaacatgggggatcatgtaactcgccttg
atcgttgggaaccgagcgtgaatgaagccataccaaacgacgagcgtgacaccacgatgcctgtagcaatggcaacaacgttgc
gcaaactattaactggcgaactacttactctagcttcccggcaacaattaatagactggatggaggcggataaagttgcaggac
cacttctgcgctcggcccttccggctggctggtttattgctgataaatctggagccggtgagcgtgggtctcgcggtatcattg
cagcactggggccagatggtaagccctcccgtatcgtagttatctacacgacggggagtcaggcaactatggatgaacgaaata
gacagatcgctgagataggtgcctcactgattaagcattggtaactgtcagaccaagtttactcatatatactttagattgatt
taaaacttcatttttaattttaaaaggatctaggtgaagatcctttttgataatctcatgaccaaaatcccttaacgtgagtttt
cgttccactgagcgtcagaccccgtagaaaagatcaaaggatcttcttgagatcctttttttctgcgcgtaatctgctgcttgc
aaacaaaaaaaccaccgctaccagcggtggtttgtttgccggatcaagagctaccaactctttttccgaaggtaactggcttca
gcagagcgcagataccaaatactgttcttctagtgtagccgtagttaggccaccacttcaagaactctgtagcaccgcctacat
acctcgctctgctaatcctgttaccagtggctgctgccagtggcgataagtcgtgtcttaccgggttggactcaagacgatagt
taccggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcagggtcg
gaacaggagagcgcacgagggagcttccaggggggaaacgcctggtatctttatagtcctgtcgggtttcgccacctctgacttg
agcgtcgatttttgtgatgctcgtcaggggggcggagcctatggaaaaacgccagcaacgcggcctttttacggttcctggcct
tttgctggccttttgctcacatggctcgacagatcttaaggctagagtacttaatacgactcactataggctagcatttaggtg
acactatagaatacaagctacttgttcttttttgcactcgagaattcacgcgtggtacctctagagtcgacccgttatttccac
catattgccgtcttttggcaatgtgagggcccggaaacctggccctgtcttcttgacgagcattcctaggggtcttttcccctct
cgccaaaggaatgcaaggtctgttgaatgtcgtgaaggaagcagttcctctggaagcttcttgaagacaaacaacgtctgtagc
gaccctttgcaggcagcggaaccccccacctggcgacaggtgcctctgcggccaaaagccacgtgtataagatacacctgcaaa
ggcggcacaaccccagtgccacgttgtgagttggatagttgtggaaagagtcaaatggctctcctcaagcgtattcaacaaggg
gctgaaggatgcccagaaggtaccccattgtatgggatctgatctggggcctcggtgcacatgctttacatgtgtttagtcgag
gttaaaaaacgtctaggccccccgaaccacggggacgtggttttccttatggcggatgtgtgacatacacgacgccaaaagat
tttgttccagctcctgccacctccgctacgcgagagattaaccacccacgatgccgccaaagtgcatgttgatattgaggctg
acagcccattcatcaagtctttgcagaaggcatttccgtcgttcgaggtggagtcattgcaggtcacaccaaatgaccatgcaa
atgccagagcattttcgcacctggctaccaaattgatcgagcaggagactgacaaagacacactcatcttggatatcggcagtg
cgccttccaggagaatgatgtctacgcacaaataccactgcgtatgccctatgcgcagcgcagaagacccccgaaaggctcgata
gctacgcaaagaaactggcagcggcctccgggaaggtgctggatagagatcgcaggaaaaatcaccgacctgcagaccgtca
tggctacgccagacgctgaatctcctaccttttgcctgcatacagacgtcacgtgtcgtacggcagccaagtggccgtatacc
aggacgtgtatgctgtacatgcaccaacatcgctgtaccatcaggcgatgaaggtgtcagaacggcgtattggattgggtttg
acaccaccccgtttatgtttgacgcgctagcaggcgcgcataccgcacaaactacgccacaaactacgccgacgagcaggtgttacagg
ccaggaacataggactgtgtgcagcatccttgactgagggaagactcggcaaactgtccattctccgcaagaagcaattgaaac
cttgcgacacagtcatgttctcggtaggatctacattgtacactgagagcagaaagctactgaggagctggcacttaccctccg
tattccacctgaaaggtaaacaatcctttacctgtaggtgcgataccatcgtatcatgtgaagggtacgtagttaagaaaatca
ctatgtgcccggcctgtacggtaaaacggtagggtacgccgtgacgtatcacgcggaggattcctagtgtgcaagaccacag
acactgtcaaaggagaaagagtctcattccctgtatgcacctacgtcccctcaaccatctgtgatcaaatgactggcatactag
cgaccgacgtcacaccggaggacgcacagaagttgttagtgggattgaatcagaggatagttgtgaacggaagaacacagcgaa
acactaacacgatgaagaactatctgcttccgattgtggccgtcgcatttagcaagtgggcgagggaatacaaggcagaccttg
atgatgaaaaacctctgggtgtccgagagaggtcacttacttgctgctgcttgtgggcatttaaaaacgaggaagatgcaacca
tgtacaagaaaccagacacccagacaatagtgaaggtgccttcagagtttaactcgttcatcccgacctatggtctacag
gcctcgcaatcccagtcagatcacgcattaagatgctttccaagaagaccaagcgagagttaatacctgttctcgacgcgt
cgtcagccagggatgctgaacaagaggagaaggagaggttggaggccgagctgactagagaagccttaccacccctcgtcccca
tcgcgccggcggagacgggagtcgtcgacgtcgacgttgaagaactagagtatcacgcaggtgcaggggtcgtggaaacacctc
gcagccgcgttgaaagtcaccgcacagccgaacgacgtactactaggaaattacgtagttctgtccccgcagaccgtgctcaaga
gctcaagttggcccccgtgcaccctctagcagacaggtgaaaataataacacataacgggagggccggcggttaccaggtcg
acggatatgacggcagggtcctactaccatgtggatcggccattccggtccctgagtttcaagctttgagcgagagcgcacta
tggtgtacaacgaaagggagttcgtcaacaggaaactataccatattgccgttcacggaccgtcgctgaacaccgacgaggaga
actacgagaaagtcagagctgaaagaactgacgccgagtacgttgttcgactagtaaaaagctgcgtcaagagagagat
cgtcgggtttggtgttggtggggagagctaaccaaccccccgttccatgaattcgcctacgaagggctgaagatcaggcccgtcgg
caccatataagactacagtagtaggagtctttggggttccgggatcaggcaagtctgctattattaagagcctcgtgaccaaac
acgatctggtcaccagcggcaagaaggagaactgccaggaaatagttaacgacgtgaagaagcaccgcgggaaggggacaagta
gggaaaacagtgactccatcctgctaaacgggtgtcgtcgtgccgtggacatcctatatgtggacgaggctttcgctagccatt
ccggtactctgctgccctaattgctcttgttaaacctcggagcaaagtggtgttatgcggagaccccaagcaatgcggattct
tcaatatgatgcagcttaaggtgaacttcaaccacaacatctgcaccaagatgtgctataaaagtatatccagacgttgcacgc
gtccagtcacggccatcgtgtctacgttgcactacgaggcaagatgcgcacgaccaacccgtgcaacaaacccataatcatag
acaccacaggacagaccaagcccaagcaggagacatcgtgttaacatgcttccgaggctgggcaaagcagctcagttggact
accgtggacacgaagtcatgacagcagcagcatctcagggcctcacccgcaaagggggtatacgccgtaaggcagaaggtgaatg
aaaatcccttgtatgccctgcgtcggagcacgtaatgtactgctgacgcgcactgaggataggctggtgtggaaaacgctgg
ccggcgatccctggattaaggtcctatcaaacattccacagggtaactttacggccacattggaagaatggcaagaagaacacg
```

```
                                SEQUENCE LISTING acaaaataatgaaggtgattgaaggaccggctgcgcctgtggacgcgttccagaacaaagcgaacgtgtgttgggcgaaaagcc
tggtgcctgtcctggacactgccggaatcagattgacagcagaggagtggagcaccataattacagcatttaaggaggacagag
cttactctccagtggtggccttgaatgaaatttgcaccaagtactatggagttgacctggacagtggcctgttttctgccccga
aggtgtccctgtattacgagaacaaccactgggataacagacctggtggaaggatgtatggattcaatgccgcaacagctgcca
ggctggaagctagacataccttcctgaaggggcagtggcatacgggcaagcaggcagttatcgcagaaagaaaaatccaaccgc
tttctgtgctggacaatgtaattcctatcaaccgcaggctgccgcacgcccctggtggctgagtacaagacggttaaaggcagta
gggttgagtggctggtcaataaagtaagagggtaccacgtcctgctggtgagtgagtacaacctggctttgcctcgacAcaggg
tcacttggttgtcaccgctgaatgtcacaggcgccgataggtgctacgacctaagtttaggactgccggctgacgccggcaggt
tcgacttggtctttgtgaacattcacacggaattcagaatccaccactaccagcagtgtgtcgaccacgccatgaagctgcaga
tgcttggggagatgcgctacgactgctaaaaAccggcggcatcttgatgagagcttacggatacgccgataaaatcagcgaag
ccgttgtttcctccttaagcagaaagttctcgtctgcaagagtgttgcgcccggattgtgtcaccagcaatacagaagtgttct
tgctgttctcaactttgacaacggaaagaaccctctacgctacaccagtgatgaataccaagctgagtgccgtgtatgccggag
aagccatgcacacggccgggtgtgcaccatcctacagagttaaggagagcagacatagccacgtgcacagaagcggctgtggta
acgcagctaacgcccgtggaactgtagggatggcgtatgcagggccgtggcgaagaaatggccgtcagcctttaagggagcag
caacaccagtgggcacaattaaaacagtcatgtgcggctcgtaccccgtcatccacgctgtagcgcctaattctctgccacga
ccagatattcagatatttgaagcggaaggggaccgcgaattggccgctgtctaccgggcagtggccgccgaagtaaacagactg
tcactgagcagcgtagccatcccgctgctgtccacaggagtgttcaggcggcggaagagataggctgcagcaatccctcaaccat
ctattcacagcaatggacgccacgacgctgacgtgaccatctactgcagagacaaaagttgggagaagaaaatccaggaagcc
attgacatgaggacggctgtggagtgctcaatgatgacgtggagctgaccacagacttggtgagagtgcacccggacagcagc
ctggtgggtcgtaagggctacagtaccactgacgggtcgctgtactcgtactttgaaggtacgaaattcaaccaggctgctatt
gatatggcagagatactgacgttgtggcccagactgcaagaggcaaacgaacagatatgcctatacgcgctgggcgaaacaatg
gacaacatcagatccaaatgtccggtgaacgattccgattcatcaacaccctccaggacagtgccctgcctgtgccgctacgca
atgacagcagaacggatcgcccgccttaggtcacaccaagttaaaagcatggtggtttgctcatcttttccctcccgaaatac
catgtagatggggtgcagaaggtaaagtgcgagaaggttctcctgttcgacccgacggtacctcagtggttagtccgcggagag
tatgccgcatctacgacggaccactcagatcggtcgttacgagggtttgacttggactggaccaccgactcgtcttccactgcc
agcgataccatgtcgctacccagtttgcagtcgtgtgacatcgactcgatctacgagccaatggctcccatagtagtgacggct
gacgtacaccctgaacccgcaggcatcgcggacctggcggcagatgtgcaccctgaacccgcagaccatgtggacctcgagaac
ccgattcctccaccgcgcccgaagagagctgcatacctgcctcccgcgcgggcgacggtgctagcggccgccaccaagaga
acgcctgccccaaggactgcgtttaggaacaagctgcctttgacgttcggcgactttgacgagcacgaggtcgatgcgttggcc
tccgggattactttcggagacttcgacgacgtcctgcgactaggccgcgcgggtgcatatattttctcctcggacactggcagc
ggacatttacaacaaaaatccgttaggcagcacaatctccagtgcgcacaactggatgcggtccaggaggagaaaatgtacccg
ccaaaattggatactgagagggagaagctgttgctgctgaaaatgcagatgcacccatcggaggctaataagagtcgataccag
tctcgcaaagtggagaacatgaaagccacggtggtggacaggctcacatcggggggccagattgtacacgggagcggacgtaggc
cgcataccaacatacgcggttcggtaccccgccccgtgtactccctaccgtgatcgaaagattctcaagcccccgatgtagca
atcgcagcgtgcaacgaatacctatccagaaatacccaacagtggcgtcgtaccagataacagatgaatacgacgcatacttg
gacatggttgacgggtcggatagttgcttggacagagcgacattctgcccggcgaagctccggtgctaccgaaacatcatgcg
taccaccagccgactgtacgcagtgccgtccccgtcacccttcagaacacactacagaacgtgctagcggccgccaccaagaga
aactgcaacgtcacgcaaatgcgagaactacccaccatggactcggcagtgttcaacgtggagtgcttcaagcgctatgcctgc
tccggagaatattgggaagaatatgctaaacaacctatccggataacaactgagaacatcactacctatgtgaccaaattgaaa
ggcccgaaagctgctgccttgttcgctaagacccacaacttggttccgctgcaggaggttcccatggacagattcacggtcgac
atgaaacgagatgtcaaagtcactccagggacgaaacacacagaggagaaacccaggtaattcaagcagcggagcca
ttggcgaccgcttacctgtgcggcatccacagggaattagtaaggagactaaatgctgtgttacgccctaacgtgcacacattg
tttgatatgtcggccgaagactttgacgcgatcatcgcctctcacttccacccaggagaccggttctagagacggacattgca
tcattcgacaaaagccaggacgactccttggctcttacaggtttaatgatcctcgaagatctaggggtggatcagtacctgctg
gacttgatcgaggcagcctttggggaaatatccagctgtcacctaccaactggcacggcttcaagttcggagctatgatgaaa
tcgggcatgttctgactttgtttattaacactgttttgaacatcaccatagcaagcaggtactggagcagagactcactgac
tccgcctgtgcggccttcatcggcgacgacaaacatcgttcacggagtgatctccgacaagctgatggcgagaggtgcgcgtcg
tgggtcaacatggaggtgaagatcattgacgctgtcatgggcgaaaaaccccatatttttgtgggggattcatagttttgac
agcgtcacacagaccgcctgccgtgtttcagaaccccacttaagcgcctgttcaagttggctaagccgctaacagctgaagacaag
caggacgaagacaggcgacgagcactgagtgacgaggttagcaagtggttccggacaggcttgggggccgaactggaggtggca
ctaacatctaggtatgaggtagagggctgcaaaagtatcctcatagccatggccaccttggcgggggacattaaggcgtttaag
aaattgagaggacctgttatacacctctacgaattcatggctgtcagcgacgctctgctcccgtccttctccacgttcgcgtcc
ggcccggcgggaagggagaagacactgcgtccagcaggtgcccgactaaccgttggcgtgaggaactctctcacatgaagcga
cttcccccacttcccggccgccctacgacctggcggcgacggtggccacagacctggagagtggcggagctggtgcagcttgc
agcagtaacaacccggccctcctagcccggagggagaccgaggagttcaacgacctcctggacctagactttatcctttccaac
tcgctaacccaccaggaatcggtggccgccaccgtgaccacctcggcgtcagcttcatcctcgtcttcccggcgagcagcggc
cctgccagcgcgccctccacctgcagcttcagctatccgatccgggccgggggtgacccgggcgtggctgccagcaacacaggt
ggagggctcctctacagccgagaatctgcgccacctcccacggccccccttcaacctggcggacatcaatgacgtgagcccctcg
ggcggcttcgtggctgagctcctgcggccggagttggacccagtatacattccgccacagcagcctcagccgccaggtggcggg
ctgatgggcaagtttgtgctgaaggcgtctctgaccaccccctggcagcgagtacagcagcccttcggtcatcagtgttagcaaa
ggaagcccagacggcagccaccccgtggtagtggcgccctacagcggtggcccgccgcgcatgtgccccaagattaagcaagag
gcggtcccgtcctgcacggtcagccggtccctagagggcccatttgagcgctggaccccagctcagcaacggccaccggccaac
acacacgactteccccctggggcggcagctccccaccaggactaccoctacactgagtcccggaactgctgaacagcagggac
tgtcaccctggcctgcctcttccccaggattccatccccatccggggcccaactaccctecttetgccagaccagatgcag
tcacaagtcccctctctccattatcaagagctcatgccaccgggttcctgcctgccagaggagcccaagccaaagaggggaaga
aggtcgtggcccgaaaagaacagccaccacacttgtgactatgcaggctgtggcaaaacctataccaagagttctcatcc
aaggcacacctgcgaactcacacaggcgagaaacttaccactgtgactgggacgctgtgggtggaaattcgcccgctccgat
gaactgaccaggcactaccgcaaacacacagggcaccggcctttcagtgccagaagtgtgacagggccttttccaggtcggacc
accttgccttacacatgaagaggcactttcgcgcaagcgcggctccggccagtgcaccaactacgccctgctgaagctggccg
gcgacgtggagtccaacccggccccgctggacacctggcttcagacttcgccttctcaccccaccaggtggggtgatggt
cagcagggctggagccgggctgggtggatcctcgaacctggctaagcttccaagggcctccaggtgggcctggaatcggaccag
gctcagaggtattggggatctccccgatctaccgagttctgcggagggatggcatactgtgacctcaggttggac
tgggcctagtccccaagttggcgtggagactttgcagcctgagggccaggcaggagcacgagtggaaagcaactcagaggaa
cctcctctgagccctgtgccgaccgcccaatgccgtgaagttggagaaggtggaaccaactccgaggagtcccaggacatga
aagccctgcagaaggagctagaacagtttgccaagctgctgaagcagaagaggatcaccttggggtacacccaggccgacgtgg
ggctcaccctgggcgttctctttggaaaggtgttcagccagaccaccatctgtcgcttcgaggccttgcagctcagccttaaga
acatgtgtaagctgcggcccctgctggagaagtgggtggaggaagccgacaacaatgagaaccttcaggagatatgcaaatcgg
```

```
agaccctggtgcaggcccggaagagaaagcgaactagcattgagaaccgtgtgaggtggagtctggagaccatgtttctgaagt
gcccgaagccctccctacagcagatcactcacatcgccaatcagcttgggctagagaaggatgtggttcgagtatggttctgta
accggcgccagaagggcaaaagatcaagtattgagtattcccaacggaagatgtgaggctacagggacacctttcccagggg
gggctgtatcctttcctctgccccaggtccccactttggcaccccaggctatggaagcccccacttcaccacactctactcag
tcctttcctgagggcgaggcctttcctctgttcccgtcactgctctgggctctcccatgcattcaaaccgcgccaagcgcgg
ctccggcgagggcagaggaagtcttctaacatgcggtgacgtggaggagaatcccggcccttataacatgatggagacggagct
gaagccgccgggcccgcagcaagcttcgggggcggcggcggaggaggcaacgccacggcggcggcgaccggcggcaaccagaa
gaacagcccggaccgcgtcaagaggcccatgaacgccttcatggtatggtcccgggggcagcggcgtaagatggcccaggagaa
ccccaagatgcacaactcggagatcagcaagcgcctgggcgcggagtggaaactttgtccgagaccgagaagcggccgttcat
cgacgaggccaagcggctgcgcgctctgcacatgaaggagcaccggattatataaccggccgcggcggaaaaccaagacgct
catgaagaaggataagtacacgcttcccggaggcttgctggccccggcgggaacagcatggcgagcggggttggggtgggcgc
cggcctgggtgcgggcgtgaaccagcgcatggacagcatgatcacggctacgcgcacatgaacggcagcggcagctacagcatgatgca
ggagcagctgggctacccgcagcacccgggcctcaacgctcacggcgcggcacagatgcaaccgatgcaccgctacgacgtcag
cgccctgcagtacaactccatgaccagctcgcagacctcatgaacggctcgcccacctacagcatgtcctactcgcagcaggg
cacccccggtatggcgctgggctccatgggctctgtggtcaagtccgaggccagctccagccccccgtggttacctcttcctc
ccactccagggcgccctgccaggccgggacctccgggacatgatgtacctcgggggaccagtgaggatatctggaagaaattcgagctgctgttcc
tgcgcccagtagactgcacatggcccagcactaccagagcggcccggtgcccggcacggccattaacggcacactgcccctgtc
gcacatgcgcgccaagcgcggctccggcgccaccaacttctccctgctgaagcaggccggcgacgtggaggagaaccccggccc
ccccctcaacgtgaacttcaccaacaggaactatgacctcgactacgactccgtacagccctatttcatctgcgacgaggaaga
gaatttctatcaccagcaacagcagagcgagcgtgaccgcgccagtgaggatatctggaagaaattcgagctgctgttcc
caccccgcccctgtccccgagccgccgctccgggctctgctctccatcctatgttgcggtcgctcgtccttctccccaaggga
agacgatgacggcggcggtggcaacttctccaccgccgatcagctggagatgatgaccgagttacttggaggagacatggtgaa
ccagagcttcatctgcgatcctgacgacgagaccttcatcaagaacatcatcatccaggactgtatgtggagcggtttctcagc
cgctgccaagctggtctcggagaagctggcctcctaccaggctggcgaagaaggcaaacccctgccaagaggtcggagtcgggctc
cagcgtctgctccacctccagcctgtacctgcaggacctcaccgccgccgcgtccgagtgcattgaccccctcagtggtctttcc
ctacccgctcaacgacagcagctcgcccaaatcctgtacctcgtccgattccacggccttctctccttcctcggactcgctgct
gtcctccgagtcctccccacgggcagccctgagccctagtgctgcatgaggagacaccgcccaccaccagcagcgactctga
agaagagcaagaagatgaggaagaaattgatgtggtgtctgtggagaagaggcaaacccctgccaagaggtcggagtcgggctc
atctccatcccgaggccacagcaaacctccgcacagccactggtcctcaagaggtgccacgtctccactcaccagcacaacta
cgccgcacccccctccacaaggaaggactatccagctgccaagagggccaagttggacagtggcagggtcctgaagcagatcag
caacaaccgcaagtgctccagccccaggtcctcagacacggaggaaaacgacaagaggcggacacacaacgtcttggaacgtca
gaggaggaacgagctgaagcgcagcttttttgccctgcgtgaccagatccctgaattggaaaaacaacgaaaaggcccccaaggt
agtgatcctcaaaaaagccaccgcctacatcctgtccattcaagcagacagacacaagctcacctctgaaaaggacttattgag
gaaacgacgagaacagttgaaacacaaactcgaacagcttcgaaactctggtgcataagaattctgcagtcgacggtaccgcgg
gcccgggatccgcccctctcctccccccccctaacgttactggccgaagccgcttggaataaggccggtgtgcgtttgtcta
tatgttattttccaccatattgccgtcttttggcaatgtgagggcccggaaacctggccctgtcttcttgacgagcattcctag
gggtctttccctctcgccaaaggaatgcaaggtctgttgaatgtcgtgaaggaagcagttcctctggaagcttcttgaagaca
aacaacgtctgtagcgaccctttgcaggcagcggaaccccccaccctggcgacaggtgcctctgcggccaaaagccacgtgtata
agatacacctgcaaaggcggcacaaccccagtgccacgttgtgagttggatagttgtgaaagagtcaaatggctctcctcaag
cgtattcaacaaggggctgaaggatgcccagaaggtaccccattgtatgggatctgatctggggcctcggtgcacatgctttac
atgtgtttagtcgaggttaaaaaaacgtctaggccccccgaaccacggggacgtggttttcctttgaaaaacacgatgataata
tggccaca
```

What is claimed is:

1. A gene expression system comprising
   (a) a vector that comprises in a 5' to 3' orientation a bacteriophage promoter, a first capping sequence, an alphavirus replicon operatively linked to the bacteriophage promoter, a subgenomic promoter, a second capping sequence, and a gene of interest, and
   (b) a protein that comprises an exogenous RNA polymerase which transcribes the alphavirus replicon, wherein the exogenous RNA polymerase is co-delivered with the alphavirus vector into a cell,
   and wherein the gene of interest is expressed in the cytoplasm of the cell.

2. The gene expression system of claim 1, wherein the alphavirus replicon is derived from an alphavirus, wherein the alphavirus is selected from the group consisting of Sindbis virus (SIN), Semliki Forest virus (SFV), and Venezuelan equine encephalitis virus (VEE).

3. The gene expression system of claim 1, wherein the alphavirus replicon is noncytopathic.

4. The gene expression system of claim 3, wherein the alphavirus replicon has one or more mutations in the nsp2 subunit.

5. The gene expression system of claim 1, wherein the bacteriophage promoter is selected from the group consisting of T7, T3, and SP6 promoters.

6. The gene expression system of claim 1, wherein both the first and second capping sequences are the internal ribosome entry site sequence derived from encephalomyocarditis virus.

7. The gene expression system of claim 1, wherein the gene of interest encodes for an antigen.

8. The gene expression system of claim 7, wherein the antigen is selected from the group consisting of a viral antigen, a bacterial antigen, and a cancer antigen.

9. The gene expression system of claim 1, wherein the subgenomic promoter is derived from an alphavirus.

10. The gene expression system of claim 1, wherein the bacteriophage promoter is T7 promoter and the exogenous RNA polymerase is T7 RNA polymerase.

11. A method for producing an induced pluripotent stem cell, comprising
    (a) introducing into a mammalian somatic cell a gene expression system comprising a vector, wherein the vector comprises a sequence that encodes one or more mammal-derived reprogramming factors, and an exogenous RNA polymerase co-delivered with the vector, and
    (b) culturing the transduced somatic cell in the presence of a cytokine on a fibroblast feeder layer or an extracellular matrix under a condition for maintaining pluripotency and self-renewal, wherein the cytokine is basic fibroblast growth factor (bFGF) or stem cell factor (SCF).

12. The method of claim 11, wherein the sequence encodes reprogramming factors Oct 3/4, Sox2, Klf4, and c-Myc, wherein the four reprogramming factors are expressed simultaneously.

13. A method for eliciting an immune response in a subject, comprising:
    (a) delivering into the subject the gene expression system of claim 1, wherein the gene of interest encodes an antigen; and
    (b) inducing in the subject an immune response to the antigen in the subject.

14. A therapeutic composition, comprising a dendritic cell transfected with the gene expression system of claim 1, wherein the gene of interest encodes an antigen capable of being displayed on the surface of the dendritic cell, wherein the therapeutic composition is capable of producing an immune response in a subject.

15. The therapeutic composition of claim 14, wherein the antigen is a tumor antigen.

16. The therapeutic composition of claim 15, wherein the tumor antigen is one or more proteins selected from the group consisting of tyrosinase, tyrosine-related protein 1 (TRP-1), and tyrosine-related protein 2 (TRP-2).

17. A method for treating melanoma, comprising administering to a patient in need thereof a therapeutic composition of claim 14, wherein the antigen is tyrosinase, tyrosine-related protein 1 (TRP-1), or tyrosine-related protein 2 (TRP-2).

18. The method of claim 17, wherein the antigen is tyrosinase.

19. The method of claim 17, wherein the antigen is tyrosine-related protein 1 (TRP-1).

20. The method of claim 17, wherein the antigen is tyrosine-related protein 2 (TRP-2).

* * * * *